(12) United States Patent
Jensen et al.

(10) Patent No.: US 6,514,735 B1
(45) Date of Patent: Feb. 4, 2003

(54) DNA SEQUENCE ENCODING ENZYMES OF CLAVULANIC ACID BIOSYNTHESIS

(75) Inventors: Susan E. Jensen, Edmonton (CA); Kwamena A. Aidoo, Timberlea (CA); Ashish S. Paradkar, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/726,614

(22) Filed: Dec. 1, 2000

Related U.S. Application Data

(63) Continuation of application No. 09/385,028, filed on Aug. 30, 1999, now Pat. No. 6,232,106, which is a division of application No. 08/790,462, filed on Jan. 29, 1997, now abandoned, which is a continuation-in-part of application No. 08/567,801, filed on Dec. 6, 1995, now abandoned, which is a continuation of application No. 08/134,018, filed on Oct. 8, 1993, now abandoned.

(51) Int. Cl.$^7$ .............................. C12N 9/06; C12N 9/02; C07K 14/36
(52) U.S. Cl. ....................... 435/191; 435/189; 530/350
(58) Field of Search ................................ 435/189, 886, 435/191; 530/350

(56) References Cited

FOREIGN PATENT DOCUMENTS

EP 0 349 121 A2 1/1990

OTHER PUBLICATIONS

Li et al. Journal of Bacteriology, vol. 182 (14), pp. 4087–4095 (Jul. 2000).*
Jensen et al. Antimicrobial Agents and Chemotherapy, 44, 720–726 (2000).*
Elson et al. (1993) J. Chem. Soc., Chem. Commun., pp. 1211–1212.*
The Sixth Conference on the Genetics and Molecular Biology of Industrial Microorganisms, (GMBIM) Oct. 20–24, 1996, Bloomington, In. p. 26, P48 Identification of a Pathway–specific Transcriptional Activator Involved in Clavulanic Acid Biosynthesis in *Streptomyces clavuligerus*, A.S. Paradkar, K.A. Aidoo, and S.E. Jensen.
Journal of Bacteriology, vol. 177, Mar., 1995, p. 1307–1314—Functional Analysis of the Gene Encoding the Clavaminate Synthase 2 Isoenzyme Involved in Clavulanic Acid Biosynthesis in *Streptomyces clavuligeru*, Ashish S. Paradkar and Susan E. Jensen.
Gene, 147 (1994) 41–46, Cloning, Sequencing and disruption of a gene from *Streptomyces clavuligerus* involved in clavulanic acid biosynthesis—Kwamena A. Aidoo, Annie Wong, Dylan C. Alexander, Randy A.R. Rittammer and Susan E. Jensen.

Industrial Microorganisms: Basic and Applied Molecular Genetics, 1993 American Society for Microbiology, Washington, Chapter 22, pp. 169–176, Extending the β–Lactam Biosynthetic Gene Cluster in *Streptomyces clavuligerus*, Susan E. Jensen, Dylan C. Alexander, Ashish S. Paradkar, and Kwamena A. Aidoo.
Antimicrobial Agents and Chemotherapy, Nov. 1982, vol. 22, p. 753–762, Assay of Amoxicillin and Clavulanic Acid, the Components of Augmenin, in Biological Fluids with High–Performance Liquid Chromatograpy, Mark Foulstone and Christopher Reading.
Biochemistry 1992, 31; 12648–12657, Two Isozymes of Clavaminate Synthase Central to Clavulanic Acid Formation:Cloning and Sequencing of Both Genes from *Streptomyces clavuligerus*, E. Neil Marsh, Margaret Dah–Tsyr Chang, and Craig A. Towsend.
Journal of Bacteriology, Sep. 1990, vol. 172, p. 4909–4918—Isolation and Characterization of a β–Lactamase–Inhibitory Protein from *Streptomyces clavuligerus* and Cloning and Analysis of the Corresponding Gene, James L. Doran, Brenda K. Leskiw, Sven Aippersbach and Susan E. Jensen.
FEMS Microbiology Letters 110 (1993) 239–242, The biosynthetic genes for clavulanic acid and cephamycin production occur as a "super–cluster" in three *Streptomyces*, Judith M. Ward and John E. Hodgson.
Journal of Bacteriology, Dec. 1990, vol. 172, 7269–7271, Purification and Partial Characterization of δ–(L–α–Aminoadipyl)–L–Cysteinyl–D–Valine Synthetase from *Streptomyces clavuligerus*, Susan E.Jensen, A. Wong, M.J. Rollins and D.W.S. Westlake.
Eur. J. Biochem. 235, 687–694 (1992) Enzymatic characteristion of the multifunctional enzyme δ–(L–α–aminoadipyl)–L–cysteinyl–D–valine synthetase from *Streptomyces clavuligerus*, Torsten Schwecke, Yair Aharonowitz, Harriet Palissa, Hans von Dohren, Horst Kleinkauf and Henk van Liempt.
Biotechnology Letters vol. 12 No. 9. 649–654 (1990), Purification of ACV Synthetase from *Streptomyces Clavuligerus*, Jinyou Zhang and Arnold L. Demain.
ATCC Catalogue of Bacteria and Phages, American Type Culture Collection, Rockville, Maryland, 1992, pp. 321, 675.
Hunkapillar et al. Meth. Enzymol., 91:227–236 (1983).
Ohtsuka et al, J. Biol. Chem., 260:2605–2608 (1985).
Lathe, J. Mol. Biol., 183:1–12 (1985).
Elson et al, J. Chem. Soc., Chem. Commun., 1993, pp. 1212–1214.

(List continued on next page.)

*Primary Examiner*—Elizabeth Slobodyansky
(74) *Attorney, Agent, or Firm*—Jacobson Holman, PLLC

(57) ABSTRACT

DNA sequences are provided which encode the enzymes required for clavulanic acid synthesis. A process is provided for producing clavulanic acid in a transformant of a non-clavulanate-producing host.

1 Claim, 35 Drawing Sheets

OTHER PUBLICATIONS

Jensen et al, Expression of the *Streptomyces clavuligerus* Isopronnicillin In Synthase Gene in *Escherichia coli* and *Streptomyces lividans*, Genetics and Molecular Biology of Industrial Microorganisms, 1989, pp. 239–245.

Valentine et al, J. Chem. Soc., Chem. Commun., 1993, pp. 1210–1211.

Jensen et al, Appl. Microbiol. Biotechnol. (1984) 20:155–160.

Madduri et al, Journal of Bacteriology, vol. 173, Feb. 1991, pp. 985–988.

Madduri et al, Journal of Bacteriology, vol. 171, Jan. 1989, pp. 299–302.

Jensen, Journal of Bacteriology, Dec. 1990, pp. 7269–7271.

Elson et al, J. Chem. Soc., Commun. 1993, pp. 1211–1212.

* cited by examiner

FIG. 1

| | Met | Glu | Arg | Ile | Asp | Ser | His | Val | Ser | Pro | Arg | | |
|---|---|---|---|---|---|---|---|---|---|---|---|---|---|
| N-terminal amino acid sequence of CLA | Tyr | Ala | Gln | Ile | Pro | Thr | Phe | Met | Arg | (Leu) | Pro | His | Asp (Asp) |
| Potential codons (DNA) | TAT | GCT | CAA | ATT | CCT | ACT | TTT | ATG | | | | | |
| | C | C | G | C | C | C | C | | | | | | |
| | | A | | A | A | A | | | | | | | |
| | | G | | | G | G | | | | | | | |
| Probe made = 24-mer oligonucleotide with 8-fold degeneracy | TAC | GCC | CAG | ATC | CCC | ACC | TTC | ATG | | | | | |
| | | G | | | G | G | | | | | | | |
| Actual DNA sequence | TAC | GCA | CAG | ATC | CCC | ACC | TTC | ATG | | | | | |

FIG. 2A

```
         |  10       |  20       |  30       |  40       |  50       |  60
   1  gcggaaccgg  ccgccccctga  gcggggcggc  cgggaaggaa  acgggccggt  cgtccctcg   60
                                                       <--End of ORF 1
  61  ggaggggcg   gccggcccgt   ccggtgcgcg  cggtgggtgc  ggcgcgggTC  AGCCGGCCGC  120
 121  GAGGTTGCTG  AGGAACTTCG   CGGCGACGGG  GCCCGCGTCG  GCGCCGCCCG  ACCCGCCGTC  180
 181  CTCCAGCAGG  ACCGACCAGG   CGATGTTCCG  GTCGCCCTGG  TAGCCGATCA  TCCAGGCGTG  240
 241  CGTCTTCGGC  GGCTTCTCGG   TGCCGAACTC  GGCGGTACCG  GTCTTGGCGT  GCGGCTGTCC  300
 301  GCCGAGGCCC  CGCAGGGCGT   CGCCGGCGCC  GTCGGTGACG  GTCGAACGCA  TCATGGAACG  360
 361  CAGCGAGTCG  ACGATGCCCG   GGGCCATCCG  GGGGGCCTGG  TGCGGCTTCT  TGACCGCGTC  420
 421  GGGCACCAGC  ACGGGCTGCT   TGAACTCGCC  CTGCTTGACG  GTGGCGGCGA  TGGAGGCCAT  480
 481  CACCAGGGGC  GACGCCTCGA   CCCTGGCCTG  TCCGATGGTG  GACGCGGCCT  TGTCGTTCTC  540
 541  GCTGTTGGAG  ACGGGGACGC   TGCCGTCGAA  GGTGGAGGCG  CCGACGTCCC  AGGTGCCGCC  600
 601  GATGCCGAAG  GCTTCGGCGG   CCTGCTTCAG  GCTGGACTCG  GAGAGCTTGC  TGCGGGAGTT  660
 661  GACGAAGAAC  GTGTTGCAGG   AGTGGGCGAA  GCTGTCCCGG  AAGGTCGAGC  CGCGGGCAG   720
 721  CGTGAACTGG  TCCTGGTTCT   CGAAGCTCTG  GCCGTTGACA  TGGGCGAACT  TCGGGCAGTC  780
 781  GGCCCGCTCC  TCCGGGTTCA   TCCCCTGCTG  GAGCAGGGCC  GCGGTGGTGA  CCACCTTGAA  840
 841  GGTGGAGCCG  GGCGGGTAGC   GGCCCTCCAG  CGCGCGGTTC  ATGCCGGAGG  GCACGTTCGC  900
 901  GGCGGCCAGG  ATGTTGCCGG   TGGCGGGGTC  GACGGCGACG  ATCGCCGCGT  TCTTCTTCGA  960
 961  GCCCTCCAGG  GCCGCCGCGG   CGGCGGACTG  GACCCGCGGG  TCGATGGTGG  TCTTCACCGG  1020
1021  CTTGCCCTCG  GTGTCCTTGA   GGCCGGTGAG  CTTCTTGACC  ACCTGGCCGG  ACTCACGGTC  1080
1081  CAGGATCACG  ACCGAGCGCG   CCGCGCCGGA  GCCGCCGGTG  AGCTGCTTGT  CGTAGCGGGA  1140
1141  CTGGAGGCCC  GCCGAGCCCT   TGCCGGTCCT  GGGGTCGACC  GCGCCGATGA  TGGAGGCGGC  1200
1201  CTGGAGGACA  TTGCCGTTGG   CGTCGAGGAT  GTCCGCGCGC  TCCCGCGACT  TGAGGGCGAG  1260
1261  GGTCTGCCCC  GGAACCATCT   GCGGATGGAT  CATCTCGGTG  TTGAACGCGA  CCTTCCACTC  1320
1321  CTTGCCGCCG  CCGACGACCT   TCGCGGTGGA  GTCCCAGGCG  TACTCCCCGG  CCCCGGGGAG  1380
1381  GGTCATTCTG  ACGGTGAACG   GTATCTCCAC  CTCGCCCTCG  GGGTTCTTCT  CCCCGGTCTT  1440
1441  GGCGGTGATC  TCCGTCTTCG   TCGGCTTGAG  GTTGGTCATG  ACGGATTTGA  TCAGCGACTC  1500
1501  GGCGTTGTCC  GGGGTGTCCG   TCAGCCCGGC  GGCCGTCGGG  GCGTCGCCCT  TCTCCCAGGC  1560
```

FIG. 2B

```
1561 GCCGAGGAAG GTGTCGAACT GTCCGGCCGC CGCCTCCACC TCGGGGTCGC CCGAATCCTT 1620

1621 CTCGTCGGCA ACCAGGCTGG TGTAACCCCA ATAGCCGAGC CCACCGTCA CGGCCAGCCC 1680

1681 GGCGACCACC GCGGTGGCCG CCCGGCCACG GGAGCGGCGC CTGCCCTGCG GCGGGTCATC 1740
              <--Beginning of ORF 1
1741 GCCATAGTTG TCGGAATGCG TCATggggcc aggctatgcg ggcgccctct ttccctcctc 1800

1801 cccggatacc gcgtttcagg acagtcaagg ggccgaacgg agggctggac cagccgctca 1860

1861 gcggcccgtt cccacccctt ggggggaagc ggcacccgga aggtgaccga ggcaacatcc 1920

1921 atggaaaggg gagcgaatcg gtcgccgagt tcaccgcgat tggagtagac ctctgaaagc 1980

1981 gtgacagcgg ggagtagcga caaaacggtc agaccctga agggaattga ctgaattcga 2040

2041 gtcatcgggt tcggcgacgg atgggcggtt cggccacgca ccgtcactct tgtcccctc 2100

2101 ttcacaagaa ctcccgatac gtggagaaga gagcgtgaag agcgcgtccg gtcagggttg 2160
                                                                Begin-
2161 ccgagaaccg tccaccatga cggagcctgg tactgacgga gtctggagac cgctcATGTC 2220
     ning of ORF 2-->
2221 CCGTGTATCG ACCGCCCCA GCGGCAAGCC TACCGCCGCT CACGCCCTCC TGTCACGGTT 2280

2281 GCGTGATCAC GGTGTGGGGA AGGTGTTTGG GGTTGTCGGC CGAGAGGCCG CGTCGATTCT 2340

2341 CTTCGACGAG GTCGAGGGGA TCGACTTCGT TCTGACCCGC CACGAGTTCA CCGCGGGTGT 2400

2401 CGCCGCTGAT GTCCTCGCGC GGATCACCGG TCGCCCCCAG GCGTGCTGGG CCACCCTGGG 2460

2461 CCCCGGTATG ACCAACCTCT CCACCGGTAT CGCCACGTCC GTCCTGGACC GCTCGCCGGT 2520

2521 CATCGCGCTC GCCGCGCAGT CGGAGTCGCA CGACATCTTC CGAACGACA CCCACCAGTG 2580

2581 CCTGGACTCG GTGGCGATCG TCGCCCCGAT GTCCAAGTAC GCCGTGGAGC TCCAGCGGCC 2640

2641 CCACGAGATC ACCGACCTCG TCGACTCCGC CGTGAACGCG GCCATGACCG AGCCGGTCGG 2700

2701 GCCCTCCTTC ATCTCCCTCC CGGTGGACCT GCTCGGCTCC TCCGAGGGCA TCGACACCAC 2760

2761 CGTCCCCAAC CCGCCGGCGA ACACCCCGGC GAAACCGGTC GGCGTCGTCG CCGACGGCTG 2820

2821 GCAGAAGGCC GCCGACCAGG CCGCCGCCCT GCTCGCCGAG GCCAAGCACC GGTGCTCGT 2880

2881 CGTCGGAGCG GCCGCGATCC GCTCGGGCGC CGTCCCGGCG ATCCGCGCCC TGGCCGAGCG 2940

2941 CCTGAACATC CCGGTCATCA CGACCTACAT CGCCAAGGGT GTCCTGCCGG TCGGCCACGA 3000

3001 GCTGAACTAC GGCGCCGTCA CCGGCTACAT GGACGGCATC CTCAACTTCC CGGCGCTCCA 3060

3061 GACCATGTTC GCCCCGGTGG ACCTCGTCCT CACCGTCGGC TACGACTACG CCGAGGACCT 3120

3121 GCGCCCGTCC ATGTGGCAGA AGGGCATCGA GAAGAAGACC GTCCGTATCT CCCCGACGGT 3180

3181 CAACCCGATC CCCCGGGTCT ACCGGCCCGA CGTCGACGTC GTCACCGACG TCCTCGCCTT 3240
```

FIG. 2C

```
3241 CGTGGAGCAC TTCGAGACCG CGACCGCCTC CTTCGGGGCC AAGCAGCGCC ACGACATCGA 3300

3301 GCCGCTGCGC GCCCGGATCG CGGAGTTCCT GGCCGACCCG GAGACCTACG AGGACGGCAT 3360

3361 GCGCGTCCAC CAGGTCATCG ACTCCATGAA CACCGTCATG GAGGAGGCCG CCGAGCCCGG 3420

3421 CGAGGGCACG ATCGTCTCCG ACATCGGCTT CTTCCGTCAC TACGGTGTGC TCTTCGCCCG 3480

3481 CGCCGACCAG CCCTTCGGCT TCCTCACCTC GGCGGGCTGC TCCAGCTTCG GCTACGGCAT 3540

3541 CCCCGCCGCC ATCGGCGCCC AGATGGCCCG CCCGGACCAG CCGACCTTCC TCATCGCGGG 3600

3601 TGACGGCGGC TTCCACTCCA ACAGCTCCGA CCTGGAGACC ATCGCCCGGC TCAACCTGCC 3660

3661 GATCGTGACC GTCGTCGTCA ACAACGACAC CAACGGCCTG ATCGAGCTGT ACCAGAACAT 3720

3721 CGGTCACCAC CGCAGCCACG ACCCGGCGGT CAAGTTCGGC GGCGTCGACT TCGTCGCGCT 3780

3781 CGCCGAGGCC AACGGTGTCG ACGCCACCCG CGCCACCAAC CGCGAGGAGC TGCTCGCGGC 3840

3841 CCTGCGCAAG GGTGCCGAGC TGGGTCGTCC GTTCCTCATC GAGGTCCCGG TCAACTACGA 3900
                                End of ORF 2--> Beginning of ORF 3-->
3901 CTTCCAGCCG GGCGGCTTCG GCGCCCTGAG CATCTGAtcA TGGGGGCACC GGTTCTTCCG 3960

3961 GCTGCCTTCG GGTTCCTGGC CTCCGCCCGA ACGGGCGGGG GCCGGGCCCC CGGCCCGGTC 4020

4021 TTCGCGACCC GGGGCAGCCA CACCGACATC GACACGCCCC AGGGGGAGCG CTCGCTCGCG 4080

4081 GCGACCCTGG TGCACGCCCC CTCGGTCGCG CCCGACCGCG CGGTGGCGCG CTCCCTCACC 4140

4141 GGCGCGCCCA CCACCGCGGT GCTCGCCGGT GAGATCTACA ACCGGGACGA ACTCCTCTCC 4200

4201 GTGCTGCCCG CCGGACCCGC GCCGGAGGGG GACGCGGAGC TGGTCCTGCG GCTGCTGGAA 4260

4261 CGCTATGACC TGCATGCCTT CCGGCTGGTG AACGGGCGCT TCGCGACCGT GGTGCGGACC 4320

4321 GGGGACCGGG TCCTGCTCGC CACCGACCAC GCCGGTTCGG TGCCGCTGTA CACCTGTGTG 4380

4381 GCGCCGGGCG AGGTCCGGGC GTCCACCGAG GCCAAGGCGC TCGCCGCGCA CCGCGACCCG 4440

4441 AAGGGCTTCC GCTCGCGGA CGCCCGCCGG GTCGCCGGTC TGACCGGTGT CTACCAGGTG 4500

4501 CCCGCGGGCG CCGTGATGGA CATCGACCTC GGCTCGGGCA CCGCCGTCAC CCACCGCACC 4560

4561 TGGACCCCGG GCCTCTCCCG CCGCATCCTG CCGGAGGGCG AGGCCGTCGC GGCCGTGCGG 4620

4621 GCCGCGCTGG AGAAGGCCGT CGCCCAGCGG GTCACCCCCG GCGACACCCC GTTGGTGGTG 4680

4681 CTCTCCGGCG GAATCGACTC CTCCGGGGTC GCGGCCTGTG CGCACCGGGC GGCCGGGGAA 4740

4741 CTGGACACGG TGTCCATGGG CACCGACACG TCCAACGAGT TCCGCGAGGC CCGGGCGGTC 4800

4801 GTCGACCATC TGCGCACCCG GCACCGGGAG ATCACCATCC CGACCACCGA GCTGCTGGCG 4860
```

FIG. 2D

```
4861 CAGCTCCCGT ACGCGGTGTG GGCCTCCGAG TCGGTGGACC CGGACATCAT CGAGTACCTG 4920
4921 CTCCCCCTGA CAGCGCTCTA CCGGGCGCTC GACGGGCCGG AGCGCCGCAT CCTCACCGGG 4980
4981 TACGGCGCGG ACATCCCCCT CGGGGGCATG CACCGCGAGG ACCGGCTGCC CGCGCTGGAC 5040
5041 ACCGTTCTCG CGCACGACAT GGCCACCTTC GACGGGCTGA ACGAGATGTC CCCGGTGCTG 5100
5101 TCCACGCTGG CGGGGCACTG GACCACCCAC CCGTACTGGG ACCGGGAGGT CCTCGATCTG 5160
5161 CTGGTCTCGC TGGAGGCCGG GCTCAAGCGG CGGCACGGCC GGGACAAGTG GGTGCTGCGC 5220
5221 GCCGCGATGG CCGACGCCCT CCCGGCGGAG ACCGTCAACC GGCCCAAGCT GGGCGTCCAC 5280
5281 GAGGGCTCGG GCACCACGTC CTCGTTCTCC CGGCTGCTGC TGGACCACGG TGTCGCCGAG 5340
5341 GACCGCGTCC ACGAGGCGAA GCGGCAGGTG GTGCGCGAGC TGTTCGATCT CACGGTCGGG 5400
5401 GGCGGACGGC ACCCCTCCGA GGTGGACACC GACGATGTGG TGCGCTCCGT GGCCGACCGG 5460
          End of ORF 3-->
5461 ACCGCGCGGG GGGCGGCCTA Gtcccgccac ggggagcccg ccggacgccg gacccgcgcg 5520
5521 ggaccegtac ccggggccgc ccgcggactc cggcgcaccg gcacccctgt ccccacccg 5580
5581 ttgacgaccg tcggccctcg gccctcgcgg ccctgacga ccgtcgcccg attcccagga 5640
          Beginning of ORF 4-->
5641 gggagctgaa agcGTGGAGC GCATCGACTC GCACGTTTCA CCCCGCTACG CACAGATCCC 5700
5701 CACCTTCATG CGCCTGCCGC ACGATCCCCA GCCCGCGGC TATGACGTGG TGGTCATCGG 5760
5761 AGCCCCCTAC GACGGGGGCA CCAGCTACCG TCCCGGCGCC CGGTTCGGCC CCAGGCCAT 5820
5821 CCGCAGTGAG TCGGGCCTCA TCCACGGTGT CGGCATCGAC CGGGGCCCCG GCACGTTCGA 5880
5881 CCTGATCAAC TGTGTCGACG CCGGGGACAT CAATCTGACG CCGTTCGACA TGAACATCGC 5940
5941 GATCGACACG GCGCAGAGCC ATCTGTCGGG CCTGCTGAAG GCCAACGCCG CCTTTCTGAT 6000
6001 GATCGGCGGC GACCACTCGC TGACGGTGGC CGCCCTGCGC GCGGTCGCGG AGCAGCACGG 6060
6061 CCCGCTCGCC GTGGTGCACC TGGACGCGCA CTCCGACACC AACCCGGCCT CTACGGGGG 6120
6121 CCGGTACCAC CACGGCACCC CCTTCCGGCA CGGGATCGAC GAGAAGCTGA TCGACCCGGC 6180
6181 GGCGATGGTC CAGATCGGCA TCCGGGGCCA CAACCCGAAG CCGGACTCGC TCGACTACGC 6240
6241 CCGGGGCCAC GGCGTCCGGG TGGTCACGGC GGACGAGTTC GGCGAGCTGG GGGTGGGCGG 6300
6301 GACCGCCGAC CTCATCCGCG AGAAGGTCGG CCAGCGGCCC GTGTACGTCT CGGTCGACAT 6360
6361 CGACGTGGTC GACCCCGCCT TCGCCCCCGG TACGGGCACG CCCGCGCCGG GCGGGCTCCT 6420
6421 CTCGCGCGAG GTGCTGGCGC TGCTGCGCTG CGTGGGTGAC CTGAAGCCGG TCGGCTTCGA 6480
6481 CGTGATGGAG GTGTCACCCC TCTACGACCA CGGCGGGATC ACTTCGATCC TGGCCACGGA 6540
```

FIG. 2E

```
                                          End of ORF 4-->
6541 GATCGGTGCG GAACTGCTCT ACCAGTACGC CCGAGCCCAC AGAACCCAGT TGTGAaggag 6600
          Beginning of ORF 5-->
6601 acatcgtgtc ATGGCCTCTC CGATAGTTGA CTGCACCCCG TACCGCGACG AGCTGCTCGC 6660
6661 GCTCGCCTCC GAGCTTCCCG AGGTGCCGCG CGCGGACCTC CATGGCTTCC TCGACGAGGC 6720
6721 GAAGACGCTG GCCGCCCGTC TCCCGGAGGG GCTGGCCGCC GCTCTCGACA CCTTCAACGC 6780
6781 CGTGGGCAGC GAGGACGGTT ATCTGCTGCT GCGCGGGCTG CCCGTCGACG ACAGCGAGCT 6840
6841 GCCCGAGACG CCGACCTCCA CCCCGGCCCC GCTGGACCGC AAGCGGCTGG TGATGGAGGC 6900
6901 CATGCTCGCG CTGGCCGGCC GCCGGCTCGG TCTGCACACG GGTACCAGG AGCTGCGCTC 6960
6961 GGGCACGGTC TACCACGACG TGTACCCGTC GCCCGGCGCG CACTACCTGT CCTCGGAGAC 7020
7021 CTCCGAGACG CTGCTGGAGT TCCACACGGA GATGGCGTAC CACATCCTCC AGCCGAACTA 7080
7081 CGTCATGCTG GCCTGCTCCC GCGCGGACCA CGAGAACCGG GCGGAGACGC TGGTCGGCTC 7140
7141 GGTCCGCAAG GCGCTGCCCC TGCTGGACGA GAAGACCCGG GCCCGTCTCT TCGACCGCAA 7200
7201 GGTGCCCTGC TGCGTGGACG TGGCCTTCCG CGGCGGGGTC GACGACCCGG GCGCGATCGC 7260
7261 CAACGTCAAG CCGCTCTACG GGGACGCGAA CGACCCGTTC CTCGGGTACG ACCGCGAGCT 7320
7321 GCTGGCGCCG GAGGACCCCG CGGACAAGGA GGCCGTCGCC CATCTGTCCC AGGCGCTCGA 7380
7381 CGATGTGACC GTCGGGGTGA AGCTCGTCCC CGGTGACGTC CTCATCATCG ACAACTTCCG 7440
7441 CACCACGCAC GCGCGGACGC CGTTCTCGCC CCGCTGGGAC GGGAAGGACC GCTGGCTGCA 7500
7501 CCGCGTCTAC ATCCGCACCG ACCGCAATGG ACAGCTCTCC GGCGGCGAGC GCGCGGGCGA 7560
          End of ORF 5-->
7561 CACCATCTCG TTCTCGCCGC GCCGCTGAgc ccggctcccc gaggccctgg gccccggcgc 7620
7621 cggaaccggc tcccggtcct gccccctcac ccgccgcgcg ggtgaggggg caggcccctt 7680
7681 tgtgccgggt gccgtgcgtc ctgcgagggt gccggggcgg gggggacggc ggaggtgccc 7740
7741 ggcggccggg tgccgtgcgc cgccgtggg tgctgtacag cactccgtgt gccgtgcgcc 7800
7801 accccgtgca taaatttgcc actctatggg aaataatgca gagtgcgacg ggtgaggccg 7860
          Beginning of ORF 6-->
7861 tcgccgtgcc ctttccgtga caggagacgc tgacATGTCC GACAGCACAC CGAAGACGCC 7920
7921 CCGGGATTC GTGGTGCACA CGGCGCCGGT GGGCCTGGCC GACGACGGCC GCGACGACTT 7980
7981 CACCGTCCTC GCCTCCACCG CCCCGGCCAC CGTGAGCGCC GTCTTCACCC GCTCCCGCTT 8040
8041 CGCCGGGCCG AGCGTCGTGC TGTGCCGGGA GGCGGTGGCC GACGGGCAGG CGCGCGGTGT 8100
8101 GGTGGTGCTG GCCCGCAACG CGAATGTCGC GACCGGCCTG GAGGGCGAGG AGAACGCGCG 8160
```

FIG. 2F

```
8161 CGAGGTGCGC GAGGCCGTCG CCCGGGCCCT CGGGCTGCCG GAGGGCGAGA TGCTGATCGC 8220
8221 CTCCACCGGG GTGATCGGCC GGCAGTACCC GATGGAGAGC ATCCGGGAGC ACCTCAAGAC 8280
8281 GCTGGAGTGG CCCGCCGGGG AGGGCGGCTT CGACCGCGCG GCCCGCGCCA TCATGACGAC 8340
8341 CGACACCCGG CCCAAGGAGG TCCGGGTCAG CGTCGGCGGG GCGACCCTCG TGGGCATCGC 8400
8401 CAAGGGCGTC GGCATGCTGG AGCCCGACAT GGCGACGCTG CTGACCTTCT TCGCCACGGA 8460
8461 CGCCCGGCTG GACCCGGCCG AGCAGGACCG CCTCTTCCGC CGGGTCATGG ACCGCACCTT 8520
8521 CAACGCGGTC AGCATCGACA CCGACACCTC CACCAGCGAC ACGGCGGTGC TGTTCGCCAA 8580
8581 CGGCCTGGCG GGCGAGGTCG ACGCCGGGGA GTTCGAGGAG GCGCTGCACA CGGCGGCGCT 8640
8641 GGCCCTGGTC AAGGACATCG CGAGCGACGG CGAGGGCGCG GCCAAGCTGA TCGAGGTCCA 8700
8701 GGTCACCGGC GCCCGCGACG ACGCCCAGGC CAAGCGGGTC GGCAAGACCG TCGTCAACTC 8760
8761 CCCGTTGGTG AAGACCGCCG TGCACGGCTG CGACCCCAAC TGGGGCCGGG TCGCCATGGC 8820
8821 GATCGGCAAG TGCTCGGACG ACACCGACAT CGACCAGGAG CGGGTGACGA TCCGCTTCGG 8880
8881 CGAGGTCGAG GTCTATCCGC CGAAGGCCCG GGGCGACCAG GCCGACGACG CGCTGCGGGC 8940
8941 CGCCGTCGCG GAGCATCTGC GGGGCGACGA GGTGGTCATC GGGATCGACC TCGCCATCGC 9000
9001 GGACGGGGCC TTCACCGTCT ACGGCTGCGA CCTCACCGAG GGCTATGTCC GGCTGAACTC 9060
     End of ORF 6-->
9061 GGAGTACACC ACCTGAtccc cggacaggga acgggccgcc gccccgttcc ctgtccgctc 9120
9121 ccgtccgtg tggttatacc gaccgttccc cggctatgcg cacgggacgg agcggccccc 9180
9181 gccgggcccc gcccggccgc acgatgaggg gcgatgcaag gtgacgaggg caggagggac 9240
     Beginning of ORF 7-->
9241 ATGGAGACCA CTCGGTCGAC GACCGCGGAC GAGGGCTTCG ACGCCGGGGT ACGGGAGTG 9300
9301 GTCGCGCCGA CCGACGCCCC GGGCGGGACG CTGCGGCTGG TCCGCACGGA CGACTTCGAC 9360
9361 TCGCTCGACC CCGGCAACAC GTACTACGCC TACACCTGGA ACTTCCTCCG GCTCATCGGC 9420
9421 CGGACGCTGG TCACCTTCGA CACCGCGCCG GGCAAGGCGG CCAGCGGCT CGTGCCCGAC 9480
9481 CTCGCCGAGT CGCTGGGCGA GTCCTCCGAG GACGGCCGGG TCTGGACCTA CCGGCTGCGC 9540
9541 GAGGGCCTGC GCTACGAGGA CGGCACGCCG GTCGTCTCGG CCGACATCAA GCACGCCATC 9600
9601 GCCCGCAGCA ACTACGGCAC CGATGTCCTG GGCGCCGGTC CGACCTACTT CCGCCACCTC 9660
9661 CTGGGCACCG AGTACGGCGG CCCCTGGCGG GAGCCGGACG CCGACGGACC GGTGACGCTG 9720
9721 GAGACCCCGG ACGAGCGGAC GCTGGTCTTC CGGCTGCGGG AGCCGTTCGC GGGGATGGAT 9780
9781 CTGCTGGCGA CCATGCCGTC CACCACCCCC GTGCCGCGCG ACCGGGACAC CGGCGCCGAG 9840
```

FIG. 2G

```
 9841 TACCGGCTGC GGCCCGTGGC GACCGGCCCG TACCGGATCG TCTCGTACAC CCGGGGCGAG  9900
 9901 CTGGCCGTCC TGGAGCCCAA TCCGCACTGG GACCCCGAGA CCGACCCGGT GCGCGTCCAG  9960
 9961 CGCGCCTCCC GGATCGAGGT GCACCTCGGC AAGGACCCGC ACGAGGTGGA CCGCATGCTG 10020
10021 CTGGCGGGCG AGGCCCATGT GGACCTCGCG GGCTTCGGTG TGCAGCCCGC GGCCCAGGAG 10080
10081 CGCATCCTCG CCGAGCCGGA GCTGCGCGCG CACGCGGACA ACCCGCTGAC CGGCTTCACC 10140
10141 TGGATCTACT GCCTGTCGAG CCGGATCGCC CCGTTCGACA ATGTGCACTG CCGGCGGGCC 10200
10201 GTGCAGTTCG CCACCGACAA AGCGGCCATG CAGGAGGCGT ACGGCGGCGC GGTGGGCGGC 10260
10261 GACATCGCGA CCACCCTGCT GCCCCCGACC CTCGACGGCT ACAAGCACTT CGACCGCTAC 10320
10321 CCGGTCGGCC CCGAGGGCAC CGGCGACCTG GAGGCCGCCC GCGCCGAGCT GAAGCTGGCC 10380
10381 GGGATGCCCG ACGGCTTCCG CACCAGGATC GCCGCCCGCA AGGACCGGCT CAAGGAGTAC 10440
10441 CGGGCCGCCG AGGCGCTGGC CGCCGGGCTC GCCCGGGTCG GCATCGAGGC GGAGGTGCTG 10500
10501 GACTTCCCGT CGGGCGACTA CTTCGACCGC TACGGCGGCT GCCCGGAGTA TCTGCGCGAG 10560
10561 CACGGGATCG GGATCATCAT GTTCGGCTGG GGCGCCGACT TCCCCGACGG ATACGGCTTC 10620
10621 CTCCAGCAGA TCACCGACGG GCGCGCGATC AAGGAGCGCG GCAACCAGAA CATGGGCGAG 10680
10681 CTGGACGACC CGGAGATCAA CGCGCTGCTG GACGAGGGGG CGCAGTGCGC CGACCCGGCG 10740
10741 CGGCGCGCGG AGATCTGGCA CCGCATCGAC CAGCTCACGA TGGACCACGC GGTCATCGTT 10800
10801 CCGTATCTGT ACCCGCGGTC CCTGCTCTAC CGGCACCCGG ACACCCGCAA CGCCTTCGTC 10860
                                                End of ORF 7-->
10861 ACCGGCTCCT TCGGGATGTA CGACTACGTG GCGCTCGGCG CGAAGTGAgc acggggtccg 10920
10921 gccccgggac cgtatgtccc ggggccggac cccgcccgtt ccccgcccgg tccggtccgg 10980
                           <--End of ORF 8
10981 acccggtcgc ggcccgcTCA GCCGGACATC CGGGCCCCGG CCGCGACCCC GCGCCGGATC 11040
11041 GGCCAGTGGC CCTGCGCCAG GGGCCGTTCC ACGCTGCGGC AGGCGAGAGC GGCCTCGCGG 11100
11101 AACTCCGCCT CGTACAGCGC GAGCTGGCGC AGGAACTGCC GGGTCGGGCC GGTCAGGCTG 11160
11161 GTCCCCGCG GGCTGCGCAG CAGCAGCCGG GCGCCGAGGG ACTGCTCCAG CCGGTGAATC 11220
11221 CGGCGGGTGA GCGCCGACTG GCTGATCGAC AGCACCGCCG CGGCCCGGTT GATGCTGCCG 11280
11281 TGCCGGGCCA CGGCCTGGAG CAGATGGAGA TCGTCCACAT CCAGTTTGCG GCCCTCGGCC 11340
11341 TGGCCGGGCA CGGAGCCCTG GTCGGGTCCC GCCCGAAGC GGCGGGCGTC CGCGCCGGTG 11400
11401 CGCTCCGCGT ACCACTGCGC CCACCAGGGC TCGTCCAGCA GGTCGCGGTG GTGTTCGGCG 11460
11461 AAGCGCCGGA GCTGGACCTC GGCGATCAGC GCGGCCAGCC GTCCCGCCAG CGCCCGGGGC 11520
```

FIG. 2H

```
11521 ACGATGGTGG GGTCGACGAG CAGACTCGTG GTGCGGCGCG GGCGCTCCGC CAGGGAGCGG 11580
11581 CGCACCAGCG AGGGGTCCTG CACCGCCGGG TGGGTGGGCG AGCCGAGACC TATCGCGTCC 11640
11641 CCGCGGCGCA GGATGCCCCG GGCAACCGAT GCCCCGTGA TGTGGAGCCG GGTGGGCGCG 11700
11701 GTGAGCCCGG CCAGCTGGAA GACACGTGTC ACCAGGATCT CCGAGCCGGG TCCCGTCTCG 11760
11761 GACACCCAGG TCTCGTCCCG CAGATCGGCG AGCGAGACCT CCCGCCGGGC GGCCAGCGGA 11820
11821 TGGTCCCGGG GCAGGATCAC CCACAGCGGG TCGTCCAGCA CCTCACAGGT GCGCACGGAC 11880
11881 CGCTCCAGGC TGTGCCGGGG GGACTGGAGG CTCCAGGTGT AGGCCGCGTC CACCTGGTAG 11940
11941 CCCGCCAGTT GGGCGGCGAC CTGGTGCGGG GCCTCGTGCC GGACCGACAG CAGCAGGTCC 12000
12001 AGCGAGGCCG CCGCGTCCTC CACCACCTCG TCGAGCAGGG GTTCCGTGGA GACCAGCGAC 12060
12061 AGCACCTCCG GGGCGTCCAC GGCCTCGGAG CCATGGCCGA AGATATGCGT CCGCGCGGCC 12120
12121 AGGTCGACCT GGTGGAAGAA CCGCCGCCCG GCGACGAGGA TGCGGGAGCC CGCGGTGGTC 12180
12181 AGCCGGGCCG TGTGGCGGCT GCGCAGGGTC AGCGGGAGGC CGACGATCCG GTCCAGCCGG 12240
                                            <--beginning of ORF 8
12241 TCGAGTCTGC GCTCCACGGT GCCGTGCCGG ACACCCGTCC GCCGGGCCAC TTCCATgagg 12300
12301 tctccgcagt gtcccaccgc gtccagtaaa gacagatcgc atcggctgac accagcagac 12360
12361 gtcggttctg acccgagaga caatgtcggt tccctttttcc gtcaaggact gtaccgctga 12420
12421 attgtccgaa gtggctcttg aattgcttcg gaatcgatcc taggcagcgc cgctcttcgg 12480
12481 attctcctcg ccgggaagcg gaacgcgccc ggccggatgg cgggcgcgct ccgggcgccg 12540
12541 tcccgggaac gggggacggg gcacggcacg gccggccacc cggtccgggc gcgcggcgtg 12600
                               <--end of ORF 9
12601 gacctggtcg gcggacgggt gTCAGACCTG GTCGGTGGGG CGTATGAAGA TCTCGTGGAC 12660
12661 GGTCGCGTGG TGCGGCGCGG TCACGGCGTA GCGGACCGCC TCCGCGATGT CCTGGGCCTG 12720
12721 GAGCTTGCGG ATCTGGCTGA TCCGCTGCTC GTACATCTCC TTGGTGGCGG TGTGGGTGAT 12780
12781 GTGGCCGCGC AGCTCCGTGT CGGTGGTGCC CGGCTCGATG ACGACGACCC GCACCCCGCG 12840
12841 CTCGGTGACC TCCTGGCGCA GCGTCTCGCT GAACGCGTTC ACACCGAACT TCGTGGCCTG 12900
12901 GTAGACGGCC GCGTTGCGGA CGTTCACCCG GCCCGCGATC GAGGACATCT GCACCACGGT 12960
12961 GCCCTTGCTG CGCAGCAGAT GGGGAAGGGC CGCCCGGGTC ATGTACATCA GGCCCAGGAG 13020
13021 ATTGGTGTCG ATCATCCGGG TCCAGTCGGT GGTGTCGGCG TCCTCCACCG GCCGAGCAG 13080
13081 CATGATCCCG GCGTTGTTGA CGAGGATGTC GAGGCCGCCC AGCGCCTCGA CGGTGGAGGC 13140
13141 GACGGCGGCG TCCACCCCCT GCCGGTCGGC GACGTCGAGT TCGAGGACAT GGACCTTCGC 13200
```

FIG. 21

```
13201  CCCGGCGGCG GTCAGCTCGT CACCCAGGGC GCGCAGCTTC TCGACCCGGC GCGCGGCGAT  13260
13261  GGCCACGGCG GCGCCCTCGG CGGCCAGGGC GCGGGCCGTG GCCTCGCCGA TGCCCGAGCT  13320
                                            <---beginning of ORF 9
13321  CGCGCCCGTG ATGAGCGCGA CTTTCCCCTG GAGTGCGGAT GGCATcattt cctccacatg  13380
13381  gtgctgcgat cgtggtgagc gtatgaagaa ggggtgagac ctgccgtgcc ggggcgggtt  13440
13441  ccgtacgccg gaccgttgcg gtgggcacgg ccgaccgggt acggatggcc gcagttcccc  13500
13501  ggggagttcc cggggaatgg tgaataccgc ggcgctctcc gatggtcttc ggaggacacc  13560
13561  cggggattca ccgggaatca gcggccggag ttctccccgt ccacggcaga cgctatcagc  13620
13621  gtcgcattcc ccggtgaatt cccttcggtg gaccgggtta tgactgtttc cgccgggtta  13680
13681  tgcgcgccgc cccggcggac cggccacccg cccgggggct gcggcagatt gggcgccacg  13740
                                               Beginning of ORF 10--->
13741  acatggcgcg agcagcgatc ggcggtggAT GATGAACGAG CAGCGCCTC AGTCCGACCA  13800
13801  GGTGGCACCG GCGTATCCGA TGCACCGGGT CTGCCCGGTC GACCCGCCGC CGCAACTGGC  13860
13861  CGGGCTGCGG TCCCAGAAGG CCGCGAGCCG GGTGACGCTG TGGGACGGCA GCCAGGTGTG  13920
13921  GCTGGTGACC TCGCACGCCG GGGCCCGGGC CGTCCTGGGC GACCGCCGCT TCACCGCGGT  13980
13981  GACGAGCGCG CCCGGCTTCC CGATGCTGAC CCGCACCTCC CAACTGGTGC GCGCCAACCC  14040
14041  GGAGTCGGCG TCGTTCATCC GCATGGACGA CCCGCAGCAC TCCCGGCTGC GCTCGATGCT  14100
14101  CACCCGGGAC TTCCTGGCCC GCCGCGCCGA GGCGCTGCGC CCCGCGGTGC GGGAGCTGCT  14160
14161  GGACGAGATC CTGGGCGGGC TGGTGAAGGG GGAGCGGCCG GTCGACCTGG TCGCCGGACT  14220
14221  GACGATCCCG GTGCCCTCGC GGGTCATCAC CCTGCTCTTC GGCGCCGGTG ACGACCGCCG  14280
14281  GGAGTTCATC GAGGACCGCA GCGCGGTCCT CATCGACCGC GGCTACACCC CGGAGCAGGT  14340
14341  CGCCAAGGCC CGGGACGAAC TCGACGGCTA TCTGCGGGAG CTGGTCGAGG AGCGGATCGA  14400
14401  GAACCCGGGC ACCGACCTGA TCAGCCGGCT CGTCATCGAC CAGGTGCGGC CGGGGCATCT  14460
14461  GCGGGTCGAG GAGATGGTCC CGATGTGCCG GCTGCTGCTG GTGGCCGGTC ACGGCACCAC  14520
14521  CACCAGCCAG GCGAGCCTGA GCCTGCTCAG CCTGCTCACC GACCCGGAGC TGGCCGGGCG  14580
14581  CCTCACCGAG GACCCGGCCC TGCTGCCCAA GGCGGTCGAG GAGCTGCTGC GCTTCCACTC  14640
14641  CATCGTGCAG AACGGGCTGG CCCGTGCCGC GGTGGAGGAC GTCCAGCTCG ACGATGTGCT  14700
14701  CATCCGGGCG GGCGAGGGCG TGGTGCTGTC GCTGTCGGCG GCAACCGGG ACGAGACGGT  14760
14761  CTTCCCCGAC CCGGACCGGG TGGACGTGGA CCGCGACGCC CGCCGCCATC TCGCCTTCGG  14820
14821  CCACGGCATG CACCAGTGCC TGGGCCAGTG GCTGGCCCGG GTGGAGCTGG AGGAGATCCT  14880
```

FIG. 2J

```
14881 CGCCGCGGGTG CTGCGGCTGGA TGCCCGGTGC CCGGCTCGCG GTGCCCTTCG AGGAGCTGGA 14940
                                                                  end of ORF 10-->
14941 CTTCCGTCAT GAGGTGTCCA GTTACGGGCCT CGGCGCCCTC CCGGTGACCT GGTGAgcggc 15000
15001 gtggagcggc tgaccgtcgt cctcgacgcg tcggcctgct gcgcgatggg gcgctgcgcg 15060
15061 gccacggccc ccgagatct                                              15079
       |        |        |        |        |        |
       10       20       30       40       50       60
```

ORF 4 = cla

FIG. 9

```
            10          20          30          40          50          60
            |           |           |           |           |           |
  1  MTHSDNYGDD  PPQGRRRSRG  RAATAVVAGL  AVTVGLGYWG  YTSLVADEKD  SGDPEVEAAA   60
 61  GQFDTFLGAW  EKGDAPTAAG  LTDTPDNAES  LIKSVMTNLK  PTKTEITAKT  GEKNPEGEVE  120
121  IPFTVRMTLP  GAGEYAWDST  AKVVGGGKEW  KVAFNTEMIH  PQMVPGQTLA  LKSRERADIL  180
181  DANGNVLQAA  SIIGAVDPRT  GKGSAGLQSR  YDKQLTGGSG  AARSVVILDR  ESGQVVKKLT  240
241  GLKDTEGKPV  KTTIDPRVQS  AAAAALEGSK  KNAAIVAVDP  ATGNILAAAN  VPSGMNRALE  300
301  GRYPPGSTFK  VVTAALLQQ   GMNPEERADC  PKFAHVNGQS  FENQDQFTLP  AGSTFRDSFA  360
361  HSCNTFFVNS  RSKLSESSLK  QAAEAFGIGG  TWDVGASTFD  GSVPVSNSEN  DKAASTIGQA  420
421  RVEASPLVMA  SIAATVKQGE  FKQPVLVPDA  VKKPHQAPRM  APGIVDSLRS  MMRSTVTDGA  480
481  GDALRGLGGQ  PHAKTGTAEF  GTEKPPKTHA  WMIGYQGDRN  IAWSVLLEDG  GSGGADAGPV  540
541  AAKFLSNLAA  GZ                                                         552
            |           |           |           |           |           |
            10          20          30          40          50          60
```

FIG. 10

```
          10         20         30         40         50         60
  1  MSRVSTAPSG KPTAAHALLS RLRDHGVGKV FGVVGREAAS ILFDEVEGID FVLTRHEFTA   60
 61  GVAADVLARI TGRPQACWAT LGPGMTNLST GIATSVLDRS PVIALAAQSE SHDIFPNDTH  120
121  QCLDSVAIVA PMSKYAVELQ RPHEITDLVD SAVNAAMTEP VGPSFISLPV DLLGSSEGID  180
181  TTVPNPPANT PAKPVGVVAD GWQKAADQAA ALLAEAKHPV LVVGAAAIRS GAVPAIRALA  240
241  ERLNIPVITT YIAKGVLPVG HELNYGAVTG YMDGILNFPA LQTMFAPVDL VLTVGYDYAE  300
301  DLRPSMWQKG IEKKTVRISP TVNPIPRVYR PDVDVVTDVL AFVEHFETAT ASFGAKQRHD  360
361  IEPLRARIAE FLADPETYED GMRVHQVIDS MNTVMEEAAE PGEGTIVSDI GFFRHYGVLF  420
421  ARADQPFGFL TSAGCSSFGY GIPAAIGAQM ARPDQPTFLI AGDGGFHSNS SDLETIARLN  480
481  LPIVTVVVNN DTNGLIELYQ NIGHHRSHDP AVKFGGVDFV ALAEANGVDA TRATNREELL  540
541  AALRKGAELG RPFLIEVPVN YDFQPGGFGA LSIZ                              574
          10         20         30         40         50         60
```

FIG. 11

```
         10         20         30         40         50         60
         |          |          |          |          |          |
  1  MGAPVLPAAF GFLASARTGG GRAPGPVFAT RGSHTDIDTP QGERSLAATL VHAPSVAPDR   60
 61  AVARSLTGAP TTAVLAGEIY NRDELLSVLP AGPAPEGDAE LVLRLLERYD LHAFRLVNGR  120
121  FATVVRTGDR VLLATDHAGS VPLYTCVAPG EVRASTEAKA LAAHRDPKGF PLADARRVAG  180
181  LTGVYQVPAG AVMDIDLGSG TAVTHRTWTP GLSRRILPEG EAVAAVRAAL EKAVAQRVTP  240
241  GDTPLVVLSG GIDSSGVAAC AHRAAGELDT VSMGTDTSNE FREARAVVDH LRTRHREITI  300
301  PTTELLAQLP YAVWASESVD PDIIEYLLPL TALYRALDGP ERRILTGYGA DIPLGGMHRE  360
361  DRLPALDTVL AHDMATFDGL NEMSPVLSTL AGHWTTHPYW DREVLDLLVS LEAGLKRRHG  420
421  RDKWVLRAAM ADALPAETVN RPKLGVHEGS GTTSSFSRLL LDHGVAEDRV HEAKRQVVRE  480
481  LFDLTVGGGR HPSEVDTDDV VRSVADRTAR GAAZ                              514
         |          |          |          |          |          |
         10         20         30         40         50         60
```

FIG. 12

```
            10         20         30         40         50         60
            |          |          |          |          |          |
  1  VERIDSHVSP RYAQIPTFMR LPHDPQPRGY DVVVIGAPYD GGTSYRPGAR FGPQAIRSES   60
 61  GLIHGVGIDR GPGTFDLINC VDAGDINLTP FDMNIAIDTA QSHLSGLLKA NAAFLMIGGD  120
121  HSLTVAALRA VAEQHGPLAV VHLDAHSDTN PAFYGGRYHH GTPFRHGIDE KLIDPAAMVQ  180
181  IGIRGHNPKP DSLDYARGHG VRVVTADEFG ELGVGGTADL IREKVGQRPV YVSVDIDVVD  240
241  PAFAPGTGTP APGGLLSREV LALLRCVGDL KPVGFDVMEV SPLYDHGGIT SILATEIGAE  300
301  LLYQYARAHR TQLZ                                                    314
            |          |          |          |          |          |
            10         20         30         40         50         60
```

FIG. 13

```
             10         20         30         40         50         60
             |          |          |          |          |          |
  1  MASPIVDCTP YRDELLALAS ELPEVPRADL HGFLDEAKTL AARLPEGLAA ALDTFNAVGS   60
 61  EDGYLLLRGL PVDDSELPET PTSTPAPLDR KRLVMEAMLA LAGRRLGLHT GYQELRSGTV  120
121  YHDVYPSPGA HYLSSETSET LLEFHTEMAY HILQPNYVML ACSRADHENR AETLVGSVRK  180
181  ALPLLDEKTR ARLFDRKVPC CVDVAFRGGV DDPGAIANVK PLYGDANDPF LGYDRELLAP  240
241  EDPADKEAVA HLSQALDDVT VGVKLVPGDV LIIDNFRTTH ARTPFSPRWD GKDRWLHRVY  300
301  IRTDRNGQLS GGERAGDTIS FSPRRZ                                      326
             |          |          |          |          |          |
             10         20         30         40         50         60
```

FIG. 14

```
            10          20          30          40          50          60
  1  MSDSTPKTPR  GFVVHTAPVG  LADDGRDDFT  VLASTAPATV  SAVFTRSRFA  GPSVVLCREA   60
 61  VADGQARGVV  VLARNANVAT  GLEGEENARE  VREAVARALG  LPEGEMLIAS  TGVIGRQYPM  120
121  ESIREHLKTL  EWPAGEGGFD  RAARAIMTTD  TRPKEVRVSV  GGATLVGIAK  GVGMLEPDMA  180
181  TLLTFFATDA  RLDPAEQDRL  FRRVMDRTFN  AVSIDTDTST  SDTAVLFANG  LAGEVDAGEF  240
241  EEALHTAALA  LVKDIASDGE  GAAKLIEVQV  TGARDDAQAK  RVGKTVVNSP  LVKTAVHGCD  300
301  PNWGRVAMAI  GKCSDDTDID  QERVTIRFGE  VEVYPPKARG  DQADDALRAA  VAEHLRGDEV  360
361  VIGIDLAIAD  GAFTVYGCDL  TEGYVRLNSE  YTTZ                                394
            10          20          30          40          50          60
```

FIG. 15

```
              10         20         30         40         50         60
  1  METTRSTTAD EGFDAGVRGV VAPTDAPGGT LRLVRTDDFD SLDPGNTYYA YTWNFLRLIG   60
 61  RTLVTFDTAP GKAGQRLVPD LAESLGESSE DGRVWTYRLR EGLRYEDGTP VVSADIKHAI  120
121  ARSNYGTDVL GAGPTYFRHL LGTEYGGPWR EPDADGPVTL ETPDERTLVF RLREPFAGMD  180
181  LLATMPSTTP VPRDRDTGAE YRLRPVATGP YRIVSYTRGE LAVLEPNPHW DPETDPVRVQ  240
241  RASRIEVHLG KDPHEVDRML LAGEAHVDLA GFGVQPAAQE RILAEPELRA HADNPLTGFT  300
301  WIYCLSSRIA PFDNVHCRRA VQFATDKAAM QEAYGGAVGG DIATTLLPPT LDGYKHFDRY  360
361  PVGPEGTGDL EAARAELKLA GMPDGFRTRI AARKDRLKEY RAAEALAAGL ARVGIEAEVL  420
421  DFPSGDYFDR YGGCPEYLRE HGIGIIMFGW GADFPDGYGF LQQITDGRAI KERGNQNMGE  480
481  LDDPEINALL DEGAQCADPA RRAEIWHRID QLTMDHAVIV PYLYPRSLLY RHPDTRNAFV  540
541  TGSFGMYDYV ALGAKZ                                                  556
              10         20         30         40         50         60
```

FIG. 16

```
         10         20         30         40         50         60
         |          |          |          |          |          |
  1  MEVARRTGVR HGTVERRLDR LDRIVGLPLT LRSRHTARLT TAGSRILVAG RRFFHQVDLA   60
 61  ARTHIFGHGS EAVDAPEVLS LVSTEPLLDE VVEDAAASLD LLLSVRHEAP HQVAAQLAGY  120
121  QVDAAYTWSL QSPRHSLERS VRTCEVLDDP LWVILPRDHP LAARREVSLA DLRDETWVSE  180
181  TGPGSEILVT RVFQLAGLTA PTRLHITGAS VARGILRRGD AIGLGSPTHP AVQDPSLVRR  240
241  SLAERPRRTT SLLVDPTIVP RALAGRLAAL IAEVQLRRFA EHHRDLLDEP WWAQWYAERT  300
301  GADARRFGAG PDQGSVPGQA EGRKLDVDDL HLLQAVARHG SINRAAAVLS ISQSALTRRI  360
361  HRLEQSLGAR LLLRSPRGTS LTGPTRQFLR QLALYEAEFR EAALACRSVE RPLAQGHWPI  420
421  RRGVAAGARM SGZ                                                    433
         |          |          |          |          |          |
         10         20         30         40         50         60
```

FIG. 17

```
          10         20         30         40         50         60
          |          |          |          |          |          |
  1  MPSALQGKVA LITGASSGIG EATARALAAE GAAVAIAARR VEKLRALGDE LTAAGAKVHV   60
 61  LELDVADRQG VDAAVASTVE ALGGLDILVN NAGIMLLGPV EDADTTDWTR MIDTNLLGLM  120
121  YMTRAALPHL LRSKGTVVQM SSIAGRVNVR NAAVYQATKF GVNAFSETLR QEVTERGVRV  180
181  VVIEPGTTDT ELRGHITHTA TKEMYEQRIS QIRKLQAQDI AEAVRYAVTA PHHATVHEIF  240
241  IRPTDQVZ                                                          248
          |          |          |          |          |          |
          10         20         30         40         50         60
```

FIG. 18

```
            10         20         30         40         50         60
             |          |          |          |          |          |
  1  MMNEAAPQSD QVAPAYPMHR VCPVDPPPQL AGLRSQKAAS RVTLWDGSQV WLVTSHAGAR   60
 61  AVLGDRRFTA VTSAPGFPML TRTSQLVRAN PESASFIRMD DPQHSRLRSM LTRDFLARRA  120
121  EALRPAVREL LDEILGGLVK GERPVDLVAG LTIPVPSRVI TLLFGAGDDR REFIEDRSAV  180
181  LIDRGYTPEQ VAKARDELDG YLRELVEERI ENPGTDLISR LVIDQVRPGH LRVEEMVPMC  240
241  RLLLVAGHGT TTSQASLSLL SLLTDPELAG RLTEDPALLP KAVEELLRFH SIVQNGLARA  300
301  AVEDVQLDDV LIRAGEGVVL SLSAGNRDET VFPDPDRVDV DRDARRHLAF GHGMHQCLGQ  360
361  WLARVELEEI LAAVLRWMPG ARLAVPFEEL DFRHEVSSYG LGALPVTWZ              409
             |          |          |          |          |          |
            10         20         30         40         50         60
```

FIG. 19
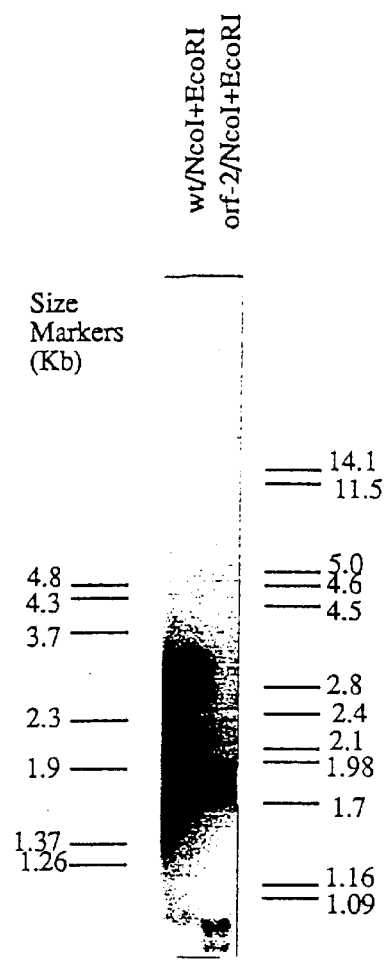
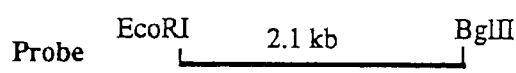
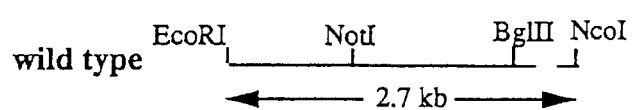
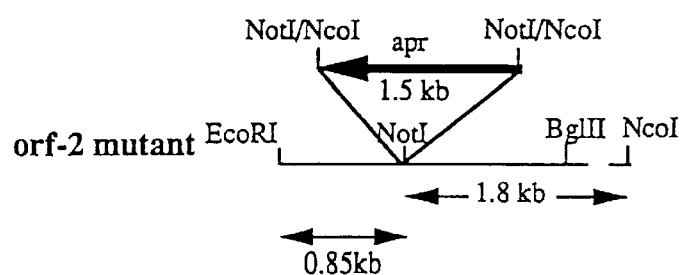

FIG. 20
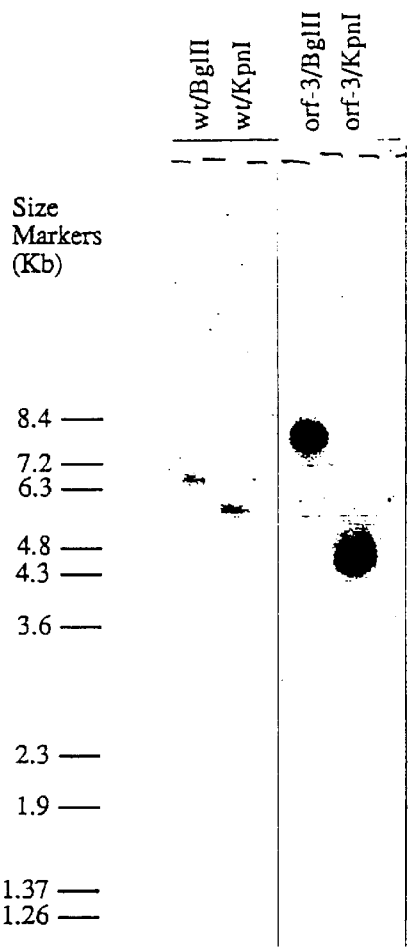
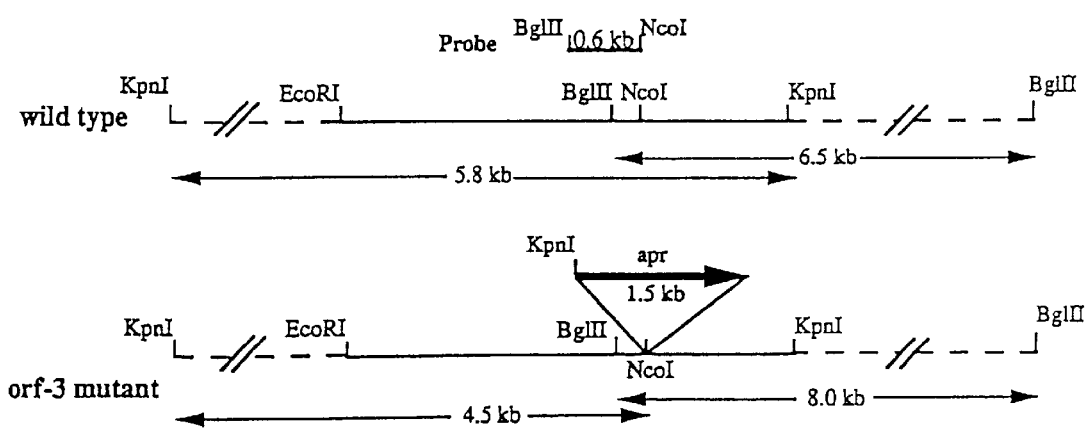

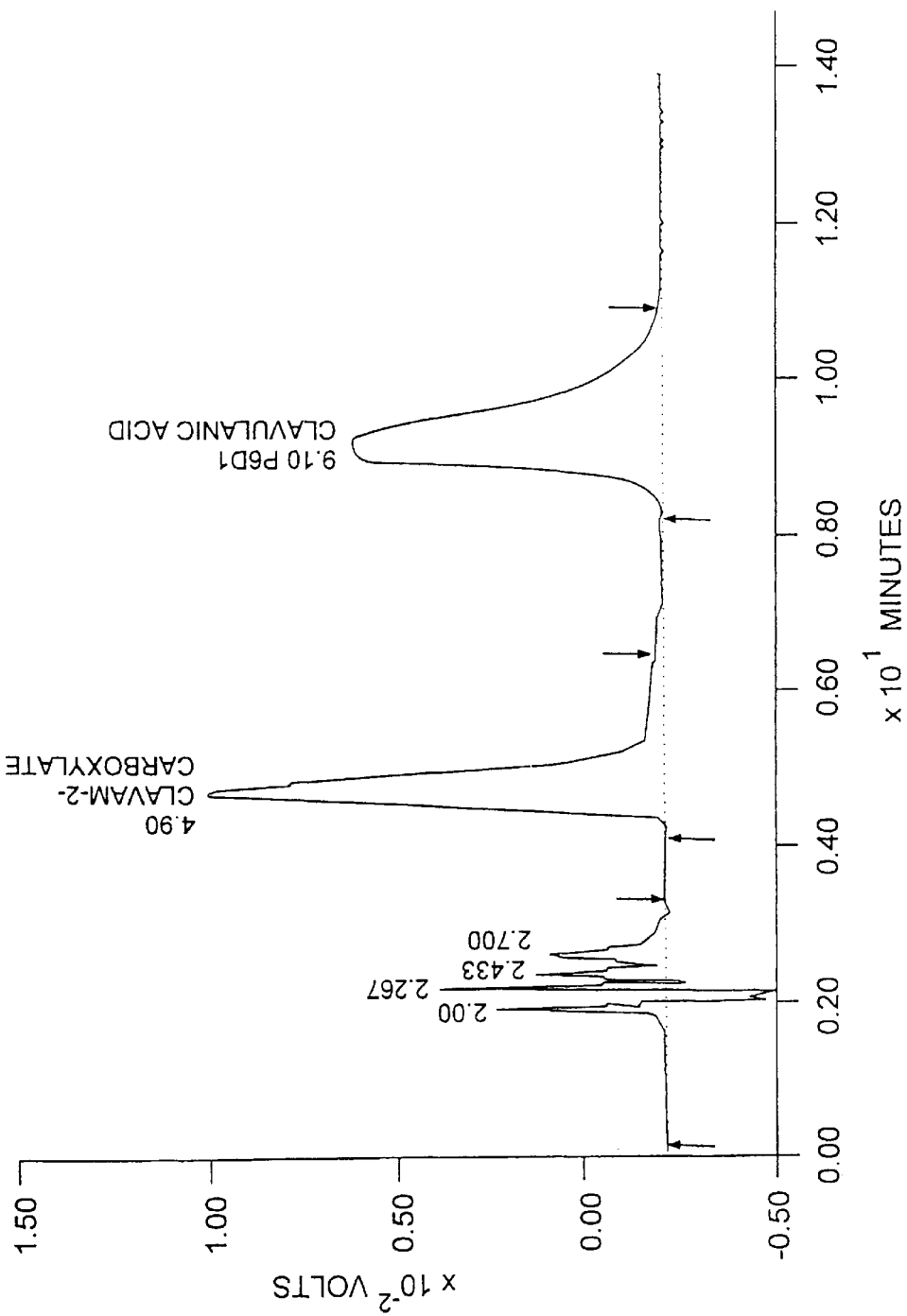

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 15079 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Streptomyces clavuligerus (xi) SEQUENCE DESCRIPTION: SEQ ID NO: 1:

```
GCGGAACCGG CCGCCCCTGA GCGGGCGGC CGGGAAGGAA ACGGGCCGGT CGTCCCCTCG      60
GGAGGGGGCG GCCGGCCCGT CCGGTGCGCG CGGTGGGTGC GGCGCGGGTC AGCCGGCCGC     120
GAGGTTGCTG AGGAACTTCG CGGCGACGGG GCCCGCGTCG GCGCCGCCCG ACCCGCCGTC     180
CTCCAGCAGG ACCGACCAGG CGATGTTCCG GTCGCCCTGG TAGCCGATCA TCCAGGCGTG     240
CGTCTTCGGC GGCTTCTCGG TGCCGAACTC GGCGGTACCG GTCTTGGCGT GCGGCTGTCC     300
GCCGAGGCCC CGCAGGGCGT CGCCGGCGCC GTCGGTGACG GTCGAACGCA TCATGGAACG     360
CAGCGAGTCG ACGATGCCCG GGCCATCCG GGGGCCTGG TGCGGCTTCT TGACCGCGTC      420
GGGCACCAGC ACGGGCTGCT TGAACTCGCC CTGCTTGACG GTGGCGGCGA TGGAGGCCAT     480
CACCAGGGGC GACGCCTCGA CCCTGGCCTG TCCGATGGTG GACGCGGCCT TGTCGTTCTC     540
GCTGTTGGAG ACGGGACGC TGCCGTCGAA GGTGGAGGCG CCGACGTCCC AGGTGCCGCC     600
GATGCCGAAG GCTTCGGCGG CCTGCTTCAG GCTGGACTCG GAGAGCTTGC TGCGGGAGTT     660
GACGAAGAAC GTGTTGCAGG AGTGGGCGAA GCTGTCCCGG AAGGTCGAGC CCGCGGGCAG     720
CGTGAACTGG TCCTGGTTCT CGAAGCTCTG GCCGTTGACA TGGGCGAACT TCGGGCAGTC     780
GGCCCGCTCC TCCGGGTTCA TCCCCTGCTG GAGCAGGGCC GCGGTGGTGA CCACCTTGAA     840
GGTGGAGCCG GGCGGGTAGC GGCCCTCCAG CGCGCGGTTC ATGCCGGAGG GCACGTTCGC     900
GGCGGCCAGG ATGTTGCCGG TGGCGGGGTC GACGGCGACG ATCGCCGCGT TCTTCTTCGA     960
GCCCTCCAGG GCCGCCGCGG CGGCGGACTG GACCCGCGGG TCGATGGTGG TCTTCACCGG    1020
CTTGCCCTCG GTGTCCTTGA GGCCGGTGAG CTTCTTGACC ACCTGGCCGG ACTCACGGTC    1080
CAGGATCACG ACCGAGCGCG CCGCGCCGGA GCCGCCGGTG AGCTGCTTGT CGTAGCGGGA    1140
CTGGAGGCCC GCCGAGCCCT TGCCGGTCCT GGGGTCGACC GCGCCGATGA TGGAGGCGGC    1200
CTGGAGGACA TTGCCGTTGG CGTCGAGGAT GTCCGCGCGC TCCCGCGACT TGAGGGCGAG    1260
GGTCTGCCCC GGAACCATCT GCGGATGGAT CATCTCGGTG TTGAACGCGA CCTTCCACTC    1320
CTTGCCGCCG CCGACGACCT TCGCGGTGGA GTCCAGGCG TACTCCCCGG CCCCGGGGAG    1380
GGTCATTCTG ACGGTGAACG GTATCTCCAC CTCGCCCTCG GGGTTCTTCT CCCCGGTCTT    1440
GGCGGTGATC TCCGTCTTCG TCGGCTTGAG GTTGGTCATG ACGGATTTGA TCAGCGACTC    1500
GGCGTTGTCC GGGGTGTCCG TCAGCCCGGC GGCCGTCGGG GCGTCGCCCT TCTCCCAGGC    1560
GCCGAGGAAG GTGTCGAACT GTCCGGCCGC CGCCTCCACC TCGGGGTCGC CCGAATCCTT    1620
CTCGTCGGCA ACCAGGCTGG TGTAACCCCA ATAGCCGAGC CCACCGTCA CGGCCAGCCC    1680
GGCGACCACC GCGGTGGCCG CCCGGCCACG GGAGCGGCGC CTGCCCTGCG GCGGGTCATC    1740
GCCATAGTTG TCGGAATGCG TCATGGGGCC AGGCTATGCG GGCGCCCTCT TTCCCTCCTC    1800
CCCGGATACC GCGTTTCAGG ACAGTCAAGG GCCGAACGG AGGGCTGGAC CAGCCGCTCA    1860
GCGGCCCGTT CCCACCCCTT GGGGGAAGC GGCACCCGGA AGGTGACCGA GGCAACATCC    1920
ATGGAAAGGG GAGCGAATCG GTCGCCGAGT TCACCGCGAT GGAGTAGAC CTCTGAAAGC    1980
GTGACAGCGG GGAGTAGCGA CAAAACGGTC AGACCCCTGA AGGGAATTGA CTGAATTCGA    2040
GTCATCGGGT TCGGCGACGG ATGGGCGGTT CGGCCACGCA CCGTCACTCT TCGTCCCCTC    2100
TTCACAAGAA CTCCCGATAC GTGGAGAAGA GAGCGTGAAG AGCGCGTCCG GTCAGGGTTG    2160
CCGAGAACCG TCCACCATGA CGGAGCCTGG TACTGACGGA GTCTGGAGAC CGCTCATGTC    2220
CCGTGTATCG ACCGCCCCCA GCGGCAAGCC TACCGCCGCT CACGCCCTCC TGTCACGGTT    2280
GCGTGATCAC GGTGTGGGGA AGGTGTTTGG GGTTGTCGGC CGAGAGGCCG CGTCGATTCT    2340
```

```
CTTCGACGAG GTCGAGGGGA TCGACTTCGT TCTGACCCGC CACGAGTTCA CCGCGGGTGT      2400

CGCCGCTGAT GTCCTCGCGC GGATCACCGG TCGCCCCCAG GCGTGCTGGG CCACCCTGGG      2460

CCCCGGTATG ACCAACCTCT CCACCGGTAT CGCCACGTCC GTCCTGGACC GCTCGCCGGT      2520

CATCGCGCTC GCCGCGCAGT CGGAGTCGCA CGACATCTTC CCGAACGACA CCCACCAGTG      2580

CCTGGACTCG GTGGCGATCG TCGCCCCGAT GTCCAAGTAC GCCGTGGAGC TCCAGCGGCC      2640

CCACGAGATC ACCGACCTCG TCGACTCCGC CGTGAACGCG GCCATGACCG AGCCGGTCGG      2700

GCCCTCCTTC ATCTCCCTCC CGGTGGACCT GCTCGGCTCC TCCGAGGGCA TCGACACCAC      2760

CGTCCCCAAC CCGCCGGCGA ACACCCCGGC GAAACCGGTC GGCGTCGTCG CCGACGGCTG      2820

GCAGAAGGCC GCCGACCAGG CCGCCGCCCT GCTCGCCGAG GCCAAGCACC CGGTGCTCGT      2880

CGTCGGAGCG GCCGCGATCC GCTCGGGCGC CGTCCCGGCG ATCCGCGCCC TGGCCGAGCG      2940

CCTGAACATC CCGGTCATCA CGACCTACAT CGCCAAGGGT GTCCTGCCGG TCGGCCACGA      3000

GCTGAACTAC GGCGCCGTCA CCGGCTACAT GGACGGCATC CTCAACTTCC CGGCGCTCCA      3060

GACCATGTTC GCCCCGGTGG ACCTCGTCCT CACCGTCGGC TACGACTACG CCGAGGACCT      3120

GCGCCCGTCC ATGTGGCAGA AGGGCATCGA GAAGAAGACC GTCCGTATCT CCCCGACGGT      3180

CAACCCGATC CCCCGGGTCT ACCGGCCCGA CGTCGACGTC GTCACCGACG TCCTCGCCTT      3240

CGTGGAGCAC TTCGAGACCG CGACCGCCTC CTTCGGGGCC AAGCAGCGCC ACGACATCGA      3300

GCCGCTGCGC GCCCGGATCG CGGAGTTCCT GGCCGACCCG GAGACCTACG AGGACGGCAT      3360

GCGCGTCCAC CAGGTCATCG ACTCCATGAA CACCGTCATG GAGGAGGCCG CCGAGCCCGG      3420

CGAGGGCACG ATCGTCTCCG ACATCGGCTT CTTCCGTCAC TACGGTGTGC TCTTCGCCCG      3480

CGCCGACCAG CCCTTCGGCT TCCTCACCTC GGCGGGCTGC TCCAGCTTCG GCTACGGCAT      3540

CCCCGCCGCC ATCGGCGCCC AGATGGCCCG CCCGGACCAG CCGACCTTCC TCATCGCGGG      3600

TGACGGCGGC TTCCACTCCA ACAGCTCCGA CCTGGAGACC ATCGCCCGGC TCAACCTGCC      3660

GATCGTGACC GTCGTCGTCA ACAACGACAC CAACGGCCTG ATCGAGCTGT ACCAGAACAT      3720

CGGTCACCAC CGCAGCCACG ACCCGGCGGT CAAGTTCGGC GGCGTCGACT TCGTCGCGCT      3780

CGCCGAGGCC AACGGTGTCG ACGCCACCCG CGCCACCAAC CGCGAGGAGC TGCTCGCGGC      3840

CCTGCGCAAG GGTGCCGAGC TGGGTCGTCC GTTCCTCATC GAGGTCCCGG TCAACTACGA      3900

CTTCCAGCCG GGCGGCTTCG CGCCCTGAG CATCTGATCA TGGGGCACC GGTTCTTCCG      3960

GCTGCCTTCG GGTTCCTGGC CTCCGCCCGA ACGGGCGGGG GCCGGGCCCC CGGCCCGGTC      4020

TTCGCGACCC GGGGCAGCCA CACCGACATC GACACGCCCC AGGGGAGCG CTCGCTCGCG      4080

GCGACCCTGG TGCACGCCCC CTCGGTCGCG CCCGACCGCG CGGTGGCGCG CTCCCTCACC      4140

GGCGCGCCCA CCACCGCGGT GCTCGCCGGT GAGATCTACA ACCGGGACGA ACTCCTCTCC      4200

GTGCTGCCCG CCGGACCCGC GCCGGAGGGG GACGCGGAGC TGGTCCTGCG GCTGCTGGAA      4260

CGCTATGACC TGCATGCCTT CCGGCTGGTG AACGGGCGCT TCGCGACCGT GGTGCGGACC      4320

GGGGACCGGG TCCTGCTCGC CACCGACCAC GCCGGTTCGG TGCCGCTGTA CACCTGTGTG      4380

GCGCCGGGCG AGGTCCGGGC GTCCACCGAG GCCAAGGCGC TCGCCGCGCA CCGCGACCCG      4440

AAGGGCTTCC CGCTCGCGGA CGCCCGCCGG GTCGCCGGTC TGACCGGTGT CTACCAGGTG      4500

CCCGCGGGCG CCGTGATGGA CATCGACCTC GGCTCGGGCA CCGCCGTCAC CCACCGCACC      4560

TGGACCCCGG GCCTCTCCCG CCGCATCCTG CCGGAGGGCG AGGCCGTCGC GGCCGTGCGG      4620

GCCGCGCTGG AGAAGGCCGT CGCCCAGCGG GTCACCCCCG GCGACACCCC GTTGGTGGTG      4680

CTCTCCGGCG GAATCGACTC CTCCGGGGTC GCGGCCTGTG CGCACCGGGC GGCCGGGGAA      4740
```

```
CTGGACACGG TGTCCATGGG CACCGACACG TCCAACGAGT TCCGCGAGGC CCGGGCGGTC    4800
GTCGACCATC TGCGCACCCG GCACCGGGAG ATCACCATCC CGACCACCGA GCTGCTGGCG    4860
CAGCTCCCGT ACGCGGTGTG GGCCTCCGAG TCGGTGGACC CGGACATCAT CGAGTACCTG    4920
CTCCCCCTGA CAGCGCTCTA CCGGGCGCTC GACGGGCCGG AGCGCCGCAT CCTCACCGGG    4980
TACGGCGCGG ACATCCCCCT CGGGGGCATG CACCGCGAGG ACCGGCTGCC CGCGCTGGAC    5040
ACCGTTCTCG CGCACGACAT GGCCACCTTC GACGGGCTGA ACGAGATGTC CCCGGTGCTG    5100
TCCACGCTGG CGGGGCACTG GACCACCCAC CCGTACTGGG ACCGGGAGGT CCTCGATCTG    5160
CTGGTCTCGC TGGAGGCCGG GCTCAAGCGG CGGCACGGCC GGGACAAGTG GGTGCTGCGC    5220
GCCGCGATGG CCGACGCCCT CCCGGCGGAG ACCGTCAACC GGCCCAAGCT GGGCGTCCAC    5280
GAGGGCTCGG GCACCACGTC CTCGTTCTCC CGGCTGCTGC TGGACCACGG TGTCGCCGAG    5340
GACCGCGTCC ACGAGGCGAA GCGGCAGGTG GTGCGCGAGC TGTTCGATCT CACGGTCGGG    5400
GGCGGACGGC ACCCCTCCGA GGTGGACACC GACGATGTGG TGCGCTCCGT GGCCGACCGG    5460
ACCGCGCGGG GGCGGCCTA GTCCCGCCAC GGGGAGCCCG CCGGACGCCG GACCCGCGCG    5520
GGACCCGTAC CCGGGGCCGC CCGCGGACTC CGGCGCACCG GCACCCCTGT CCCCCACCCG    5580
TTGACGACCG TCGGCCCTCG GCCCTCGCGG CCCCTGACGA CCGTCGCCCG ATTCCCAGGA    5640
GGGAGCTGAA AGCGTGGAGC GCATCGACTC GCACGTTTCA CCCCGCTACG CACAGATCCC    5700
CACCTTCATG CGCCTGCCGC ACGATCCCCA GCCCCGCGGC TATGACGTGG TGGTCATCGG    5760
AGCCCCCTAC GACGGGGGCA CCAGCTACCG TCCCGGCGCC CGGTTCGGCC CCCAGGCCAT    5820
CCGCAGTGAG TCGGGCCTCA TCCACGGTGT CGGCATCGAC CGGGGCCCCG GCACGTTCGA    5880
CCTGATCAAC TGTGTCGACG CCGGGGACAT CAATCTGACG CCGTTCGACA TGAACATCGC    5940
GATCGACACG GCGCAGAGCC ATCTGTCGGG CCTGCTGAAG GCCAACGCCG CCTTTCTGAT    6000
GATCGGCGGC GACCACTCGC TGACGGTGGC CGCCCTGCGC GCGGTCGCGG AGCAGCACGG    6060
CCCGCTCGCC GTGGTGCACC TGGACGCGCA CTCCGACACC AACCCGGCCT TCTACGGGGG    6120
CCGGTACCAC CACGGCACCC CCTTCCGGCA CGGGATCGAC GAGAAGCTGA TCGACCCGGC    6180
GGCGATGGTC CAGATCGGCA TCCGGGGCCA CAACCCGAAG CCGGACTCGC TCGACTACGC    6240
CCGGGGCCAC GGCGTCCGGG TGGTCACGGC GGACGAGTTC GGCGAGCTGG GGGTGGGCGG    6300
GACCGCCGAC CTCATCCGCG AGAAGGTCGG CCAGCGGCCC GTGTACGTCT CGGTCGACAT    6360
CGACGTGGTC GACCCCGCCT TCGCCCCCGG TACGGGCACG CCCGCGCCGG GCGGGCTCCT    6420
CTCGCGCGAG GTGCTGGCGC TGCTGCGCTG CGTGGGTGAC CTGAAGCCGG TCGGCTTCGA    6480
CGTGATGGAG GTGTCACCCC TCTACGACCA CGGCGGGATC ACTTCGATCC TGGCCACGGA    6540
GATCGGTGCG GAACTGCTCT ACCAGTACGC CCGAGCCCAC AGAACCCAGT TGTGAAGGAG    6600
ACATCGTGTC ATGGCCTCTC CGATAGTTGA CTGCACCCCG TACCGCGACG AGCTGCTCGC    6660
GCTCGCCTCC GAGCTTCCCG AGGTGCCGCG CGCGGACCTC CATGGCTTCC TCGACGAGGC    6720
GAAGACGCTG GCCGCCCGTC TCCCGGAGGG GCTGGCCGCC GCTCTCGACA CCTTCAACGC    6780
CGTGGGCAGC GAGGACGGTT ATCTGCTGCT GCGCGGGCTG CCCGTCGACG ACAGCGAGCT    6840
GCCCGAGACG CCGACCTCCA CCCCGGCCCC GCTGGACCGC AAGCGGCTGG TGATGGAGGC    6900
CATGCTCGCG CTGGCCGGCC GCCGGCTCGG TCTGCACACG GGGTACCAGG AGCTGCGCTC    6960
GGGCACGGTC TACCACGACG TGTACCCGTC GCCCGGCGCG CACTACCTGT CCTCGGAGAC    7020
CTCCGAGACG CTGCTGGAGT TCCACACGGA GATGGCGTAC CACATCCTCC AGCCGAACTA    7080
CGTCATGCTG GCCTGCTCCC GCGCGGACCA CGAGAACCGG GCGGAGACGC TGGTCGGCTC    7140
```

-continued

```
GGTCCGCAAG GCGCTGCCCC TGCTGGACGA GAAGACCCGG GCCCGTCTCT TCGACCGCAA    7200
GGTGCCCTGC TGCGTGGACG TGGCCTTCCG CGGCGGGGTC GACGACCCGG GCGCGATCGC    7260
CAACGTCAAG CCGCTCTACG GGACGCGAA CGACCCGTTC CTCGGGTACG ACCGCGAGCT    7320
GCTGGCGCCG GAGGACCCCG CGGACAAGGA GGCCGTCGCC CATCTGTCCC AGGCGCTCGA    7380
CGATGTGACC GTCGGGGTGA AGCTCGTCCC CGGTGACGTC CTCATCATCG ACAACTTCCG    7440
CACCACGCAC GCGCGGACGC CGTTCTCGCC CCGCTGGGAC GGGAAGGACC GCTGGCTGCA    7500
CCGCGTCTAC ATCCGCACCG ACCGCAATGG ACAGCTCTCC GGCGGCGAGC GCGCGGGCGA    7560
CACCATCTCG TTCTCGCCGC GCCGCTGAGC CCGGCTCCCC GAGGCCCTGG GCCCCGGCGC    7620
CGGAACCGGC TCCCGGTCCT GCCCCCTCAC CCGCCGCGCG GGTGAGGGGG CAGGCCCCTT    7680
TGTGCCGGGT GCCGTGCGTC CTGCGAGGGT GCCGGGCGG GGGGACGGC GGAGGTGCCC    7740
GGCGGCCGGG TGCCGTGCGC CGCCCGTGGG TGCTGTACAG CACTCCGTGT GCCGTGCGCC    7800
ACCCCGTGCA TAAATTTGCC ACTCTATGGG AAATAATGCA GAGTGCGACG GGTGAGGCCG    7860
TCGCCGTGCC CTTTCCGTGA CAGGAGACGC TGACATGTCC GACAGCACAC CGAAGACGCC    7920
CCGGGGATTC GTGGTGCACA CGGCGCCGGT GGGCCTGGCC GACGACGGCC GCGACGACTT    7980
CACCGTCCTC GCCTCCACCG CCCCGGCCAC CGTGAGCGCC GTCTTCACCC GCTCCCGCTT    8040
CGCCGGGCCG AGCGTCGTGC TGTGCCGGGA GGCGGTGGCC GACGGGCAGG CGCGCGGTGT    8100
GGTGGTGCTG GCCCGCAACG CGAATGTCGC GACCGGCCTG GAGGGCGAGG AGAACGCGCG    8160
CGAGGTGCGC GAGGCCGTCG CCCGGGCCCT CGGGCTGCCG GAGGGCGAGA TGCTGATCGC    8220
CTCCACCGGG GTGATCGGCC GGCAGTACCC GATGGAGAGC ATCCGGGAGC ACCTCAAGAC    8280
GCTGGAGTGG CCCGCCGGGG AGGGCGGCTT CGACCGCGCG GCCCGCGCCA TCATGACGAC    8340
CGACACCCGG CCCAAGGAGG TCCGGGTCAG CGTCGGCGGG GCGACCCTCG TGGGCATCGC    8400
CAAGGGCGTC GGCATGCTGG AGCCCGACAT GGCGACGCTG CTGACCTTCT TCGCCACGGA    8460
CGCCCGGCTG GACCCGGCCG AGCAGGACCG CCTCTTCCGC CGGGTCATGG ACCGCACCTT    8520
CAACGCGGTC AGCATCGACA CCGACACCTC CACCAGCGAC ACGGCGGTGC TGTTCGCCAA    8580
CGGCCTGGCG GGCGAGGTCG ACGCCGGGGA GTTCGAGGAG GCGCTGCACA CGGCGGCGCT    8640
GGCCCTGGTC AAGGACATCG CGAGCGACGG CGAGGGCGCG GCCAAGCTGA TCGAGGTCCA    8700
GGTCACCGGC GCCCGCGACG ACGCCCAGGC CAAGCGGGTC GGCAAGACCG TCGTCAACTC    8760
CCCGTTGGTG AAGACCGCCG TGCACGGCTG CGACCCCAAC TGGGGCCGGG TCGCCATGGC    8820
GATCGGCAAG TGCTCGGACG ACACCGACAT CGACCAGGAG CGGGTGACGA TCCGCTTCGG    8880
CGAGGTCGAG GTCTATCCGC CGAAGGCCCG GGGCGACCAG GCCGACGACG CGCTGCGGGC    8940
CGCCGTCGCG GAGCATCTGC GGGGCGACGA GGTGGTCATC GGGATCGACC TCGCCATCGC    9000
GGACGGGGCC TTCACCGTCT ACGGCTGCGA CCTCACCGAG GCTATGTCC GGCTGAACTC    9060
GGAGTACACC ACCTGATCCC CGGACAGGGA ACGGGCCGCC GCCCCGTTCC CTGTCCGCTC    9120
CCGTCCCGTG TGGTTATACC GACCGTTCCC CGGCTATGCG CACGGGACGG AGCGGCCCCC    9180
GCCGGGCCCC GCCCGGCCGC ACGATGAGGG GCGATGCAAG GTGACGAGGG CAGGAGGGAC    9240
ATGGAGACCA CTCGGTCGAC GACCGCGGAC GAGGGCTTCG ACGCCGGGGT ACGGGGAGTG    9300
GTCGCGCCGA CCGACGCCCC GGGCGGGACG CTGCGGCTGG TCCGCACGGA CGACTTCGAC    9360
TCGCTCGACC CCGGCAACAC GTACTACGCC TACACCTGGA ACTTCCTCCG GCTCATCGGC    9420
CGGACGCTGG TCACCTTCGA CACCGCGCCG GGCAAGGCG GCCAGCGGCT CGTGCCCGAC    9480
CTCGCCGAGT CGCTGGGCGA GTCCTCCGAG GACGGCCGGG TCTGGACCTA CCGGCTGCGC    9540
```

-continued

```
GAGGGCCTGC GCTACGAGGA CGGCACGCCG GTCGTCTCGG CCGACATCAA GCACGCCATC    9600

GCCCGCAGCA ACTACGGCAC CGATGTCCTG GGCGCCGGTC CGACCTACTT CCGCCACCTC    9660

CTGGGCACCG AGTACGGCGG CCCCTGGCGG GAGCCGGACG CCGACGGACC GGTGACGCTG    9720

GAGACCCCGG ACGAGCGGAC GCTGGTCTTC CGGCTGCGGG AGCCGTTCGC GGGGATGGAT    9780

CTGCTGGCGA CCATGCCGTC CACCACCCCC GTGCCGCGCG ACCGGGACAC CGGCGCCGAG    9840

TACCGGCTGC GGCCCGTGGC GACCGGCCCG TACCGGATCG TCTCGTACAC CCGGGGCGAG    9900

CTGGCCGTCC TGGAGCCCAA TCCGCACTGG GACCCCGAGA CCGACCCGGT GCGCGTCCAG    9960

CGCGCCTCCC GGATCGAGGT GCACCTCGGC AAGGACCCGC ACGAGGTGGA CCGCATGCTG   10020

CTGGCGGGCG AGGCCCATGT GGACCTCGCG GGCTTCGGTG TGCAGCCCGC GGCCCAGGAG   10080

CGCATCCTCG CCGAGCCGGA GCTGCGCGCG CACGCGGACA ACCCGCTGAC CGGCTTCACC   10140

TGGATCTACT GCCTGTCGAG CCGGATCGCC CCGTTCGACA ATGTGCACTG CCGGCGGGCC   10200

GTGCAGTTCG CCACCGACAA AGCGGCCATG CAGGAGGCGT ACGGCGGCGC GGTGGGCGGC   10260

GACATCGCGA CCACCCTGCT GCCCCCGACC CTCGACGGCT ACAAGCACTT CGACCGCTAC   10320

CCGGTCGGCC CCGAGGGCAC CGGCGACCTG GAGGCCGCCC GCGCCGAGCT GAAGCTGGCC   10380

GGGATGCCCG ACGGCTTCCG CACCAGGATC GCCGCCCGCA AGGACCGGCT CAAGGAGTAC   10440

CGGGCCGCCG AGGCGCTGGC CGCCGGGCTC GCCCGGGTCG GCATCGAGGC GGAGGTGCTG   10500

GACTTCCCGT CGGGCGACTA CTTCGACCGC TACGGCGGCT GCCCGGAGTA TCTGCGCGAG   10560

CACGGGATCG GGATCATCAT GTTCGGCTGG GGCGCCGACT TCCCCGACGG ATACGGCTTC   10620

CTCCAGCAGA TCACCGACGG GCGCGCGATC AAGGAGCGCG GCAACCAGAA CATGGGCGAG   10680

CTGGACGACC CGGAGATCAA CGCGCTGCTG GACGAGGGGG CGCAGTGCGC CGACCCGGCG   10740

CGGCGCGCGG AGATCTGGCA CCGCATCGAC CAGCTCACGA TGGACCACGC GGTCATCGTT   10800

CCGTATCTGT ACCCGCGGTC CCTGCTCTAC CGGCACCCGG ACACCCGCAA CGCCTTCGTC   10860

ACCGGCTCCT TCGGGATGTA CGACTACGTG GCGCTCGGCG CGAAGTGAGC ACGGGGTCCG   10920

GCCCCGGGAC CGTATGTCCC GGGGCCGGAC CCCGCCCGTT CCCCGCCCGG TCCGGTCCGG   10980

ACCCGGTCGC GGCCCGCTCA GCCGGACATC CGGGCCCCGG CCGCGACCCC GCGCCGGATC   11040

GGCCAGTGGC CCTGCGCCAG GGGCCGTTCC ACGCTGCGGC AGGCGAGAGC GGCCTCGCGG   11100

AACTCCGCCT CGTACAGCGC GAGCTGGCGC AGGAACTGCC GGGTCGGGCC GGTCAGGCTG   11160

GTCCCCGCG GGCTGCGCAG CAGCAGCCGG GCGCCGAGGG ACTGCTCCAG CCGGTGAATC   11220

CGGCGGGTGA GCGCCGACTG GCTGATCGAC AGCACCGCCG CGGCCCGGTT GATGCTGCCG   11280

TGCCGGGCCA CGGCCTGGAG CAGATGGAGA TCGTCCACAT CCAGTTTGCG GCCCTCGGCC   11340

TGGCCGGGCA CGGAGCCCTG GTCGGGTCCC GCCCCGAAGC GGCGGGCGTC CGCGCCGGTG   11400

CGCTCCGCGT ACCACTGCGC CCACCAGGGC TCGTCCAGCA GGTCGCGGTG GTGTTCGGCG   11460

AAGCGCCGGA GCTGGACCTC GGCGATCAGC GCGGCCAGCC GTCCCGCCAG CGCCCGGGGC   11520

ACGATGGTGG GGTCGACGAG CAGACTCGTG GTGCGGCGCG GGCGCTCCGC CAGGGAGCGG   11580

CGCACCAGCG AGGGGTCCTG CACCGCCGGG TGGGTGGGCG AGCCGAGACC TATCGCGTCC   11640

CCGCGGCGCA GGATGCCCCG GCAACCGAT GCCCCGTGA TGTGGAGCCG GGTGGGCGCG   11700

GTGAGCCCGG CCAGCTGGAA GACACGTGTC ACCAGGATCT CCGAGCCGGG TCCCGTCTCG   11760

GACACCCAGG TCTCGTCCCG CAGATCGGCG AGCGAGACCT CCCGCCGGGC GGCCAGCGGA   11820

TGGTCCCGGG GCAGGATCAC CCACAGCGGG TCGTCCAGCA CCTCACAGGT GCGCACGGAC   11880

CGCTCCAGGC TGTGCCGGGG GGACTGGAGG CTCCAGGTGT AGGCCGCGTC CACCTGGTAG   11940
```

```
CCCGCCAGTT GGGCGGCGAC CTGGTGCGGG GCCTCGTGCC GGACCGACAG CAGCAGGTCC   12000

AGCGAGGCCG CCGCGTCCTC CACCACCTCG TCGAGCAGGG GTTCCGTGGA GACCAGCGAC   12060

AGCACCTCCG GGGCGTCCAC GGCCTCGGAG CCATGGCCGA AGATATGCGT CCGCGCGGCC   12120

AGGTCGACCT GGTGGAAGAA CCGCCGCCCG GCGACGAGGA TGCGGGAGCC CGCGGTGGTC   12180

AGCCGGGCCG TGTGGCGGCT CGCAGGGTC AGCGGGAGGC CGACGATCCG GTCCAGCCGG    12240

TCGAGTCTGC GCTCCACGGT GCCGTGCCGG ACACCCGTCC GCCGGGCCAC TTCCATGAGG   12300

TCTCCGCAGT GTCCCACCGC GTCCAGTAAA GACAGATCGC ATCGGCTGAC ACCAGCAGAC   12360

GTCGGTTCTG ACCCGAGAGA CAATGTCGGT TCCCTTTTCC GTCAAGGACT GTACCGCTGA   12420

ATTGTCCGAA GTGGCTCTTG AATTGCTTCG GAATCGATCC TAGGCAGCGC CGCTCTTCGG   12480

ATTCTCCTCG CCGGGAAGCG GAACGCGCCC GGCCGGATGG CGGGCGCGCT CCGGGCGCCG   12540

TCCCGGGAAC GGGGGACGGG GCACGGCACG GCCGGCCACC CGGTCCGGGC GCGCGGCGTG   12600

GACCTGGTCG GCGGACGGGT GTCAGACCTG GTCGGTGGGG CGTATGAAGA TCTCGTGGAC   12660

GGTCGCGTGG TGCGGCGCGG TCACGGCGTA GCGGACCGCC TCCGCGATGT CCTGGGCCTG   12720

GAGCTTGCGG ATCGGCTGA TCCGCTGCTC GTACATCTCC TTGGTGGCGG TGTGGGTGAT    12780

GTGGCCGCGC AGCTCCGTGT CGGTGGTGCC CGGCTCGATG ACGACGACCC GCACCCCGCG   12840

CTCGGTGACC TCCTGGCGCA GCGTCTCGCT GAACGCGTTC ACACCGAACT TCGTGGCCTG   12900

GTAGACGGCC GCGTTGCGGA CGTTCACCCG GCCCGCGATC GAGGACATCT GCACCACGGT   12960

GCCCTTGCTG CGCAGCAGAT GGGGAAGGGC CGCCCGGGTC ATGTACATCA GGCCCAGGAG   13020

ATTGGTGTCG ATCATCCGGG TCCAGTCGGT GGTGTCGGCG TCCTCCACCG GCCGAGCAG    13080

CATGATCCCG GCGTTGTTGA CGAGGATGTC GAGGCCGCCC AGCGCCTCGA CGGTGGAGGC   13140

GACGGCGGCG TCCACCCCCT GCCGGTCGGC GACGTCGAGT TCGAGGACAT GGACCTTCGC   13200

CCCGGCGGCG GTCAGCTCGT CACCCAGGGC GCGCAGCTTC TCGACCCGGC GCGCGGCGAT   13260

GGCCACGGCG GCGCCCTCGG CGGCCAGGGC GCGGGCCGTG GCCTCGCCGA TGCCCGAGCT   13320

CGCGCCCGTG ATGAGCGCGA CTTTCCCCTG GAGTGCGGAT GGCATCATTT CCTCCACATG   13380

GTGCTGCGAT CGTGGTGAGC GTATGAAGAA GGGGTGAGAC CTGCCGTGCC GGGGCGGGTT   13440

CCGTACGCCG GACCGTTGCG GTGGGCACGG CCGACCGGGT ACGGATGGCC GCAGTTCCCC   13500

GGGGAGTTCC CGGGGAATGG TGAATACCGC GGCGCTCTCC GATGGTCTTC GGAGGACACC   13560

CGGGGATTCA CCGGGAATCA GCGGCCGGAG TTCTCCCCGT CCACGGCAGA CGCTATCAGC   13620

GTCGCATTCC CCGGTGAATT CCCTTCGGTG GACCGGGTTA TGACTGTTTC CGCCGGGTTA   13680

TGCGCGCCGC CCCGGCGGAC CGGCCACCCG CCCGGGGGCT GCGGCAGATT GGGCGCCACG   13740

ACATGGCGCG AGCAGCGATC GGCGGTGGAT GATGAACGAG GCAGCGCCTC AGTCCGACCA   13800

GGTGGCACCG GCGTATCCGA TGCACCGGGT CTGCCCGGTC GACCCGCCGC CGCAACTGGC   13860

CGGGCTGCGG TCCCAGAAGG CCGCGAGCCG GGTGACGCTG TGGGACGGCA GCCAGGTGTG   13920

GCTGGTGACC TCGCACGCCG GGCCCGGGC CGTCCTGGGC GACCGCCGCT TCACCGCGGT    13980

GACGAGCGCG CCCGGCTTCC CGATGCTGAC CCGCACCTCC CAACTGGTGC GCGCCAACCC   14040

GGAGTCGGCG TCGTTCATCC GCATGGACGA CCCGCAGCAC TCCCGGCTGC GCTCGATGCT   14100

CACCCGGGAC TTCCTGGCCC GCCGCGCCGA GGCGCTGCGC CCCGCGGTGC GGGAGCTGCT   14160

GGACGAGATC CTGGGCGGGC TGGTGAAGGG GGAGCGGCCG GTCGACCTGG TCGCCGGACT   14220

GACGATCCCG GTGCCCTCGC GGGTCATCAC CCTGCTCTTC GGCGCCGGTG ACGACCGCCG   14280

GGAGTTCATC GAGGACCGCA GCGCGGTCCT CATCGACCGC GGCTACACCC CGGAGCAGGT   14340
```

```
CGCCAAGGCC CGGGACGAAC TCGACGGCTA TCTGCGGGAG CTGGTCGAGG AGCGGATCGA    14400

GAACCCGGGC ACCGACCTGA TCAGCCGGCT CGTCATCGAC CAGGTGCGGC CGGGGCATCT    14460

GCGGGTCGAG GAGATGGTCC CGATGTGCCG GCTGCTGCTG GTGGCCGGTC ACGGCACCAC    14520

CACCAGCCAG GCGAGCCTGA GCCTGCTCAG CCTGCTCACC GACCCGGAGC TGGCCGGGCG    14580

CCTCACCGAG GACCCGGCCC TGCTGCCCAA GGCGGTCGAG GAGCTGCTGC GCTTCCACTC    14640

CATCGTGCAG AACGGGCTGG CCCGTGCCGC GGTGGAGGAC GTCCAGCTCG ACGATGTGCT    14700

CATCCGGGCG GGCGAGGGCG TGGTGCTGTC GCTGTCGGCG GGCAACCGGG ACGAGACGGT    14760

CTTCCCCGAC CCGGACCGGG TGGACGTGGA CCGCGACGCC CGCCGCCATC TCGCCTTCGG    14820

CCACGGCATG CACCAGTGCC TGGGCCAGTG GCTGGCCCGG GTGGAGCTGG AGGAGATCCT    14880

CGCCGCGGTG CTGCGCTGGA TGCCCGGTGC CCGGCTCGCG GTGCCCTTCG AGGAGCTGGA    14940

CTTCCGTCAT GAGGTGTCCA GTTACGGCCT CGGCGCCCTC CCGGTGACCT GGTGAGCGGC    15000

GTGGAGCGGC TGACCGTCGT CCTCGACGCG TCGGCCTGCT GCGCGATGGG GCGCTGCGCG    15060

GCCACGGCCC CCGAGATCT                                                 15079
```

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 2:

```
TACGCCCAGA TCCCCACCTT CATG                                                 24
```

(2) INFORMATION FOR SEQ ID NO: 3:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Met Thr His Ser Asp Asn Tyr Gly Asp Asp Pro Pro Gln Gly Arg Arg
1               5                   10                  15

Arg Ser Arg Gly Arg Ala Ala Thr Ala Val Val Ala Gly Leu Ala Val
            20                  25                  30

Thr Val Gly Leu Gly Tyr Trp Gly Tyr Thr Ser Leu Val Ala Asp Glu
        35                  40                  45

Lys Asp Ser Gly Asp Pro Glu Val Glu Ala Ala Gly Gln Phe Asp
    50                  55                  60

Thr Phe Leu Gly Ala Trp Glu Lys Gly Asp Ala Pro Thr Ala Ala Gly
65                  70                  75                  80

Leu Thr Asp Thr Pro Asp Asn Ala Glu Ser Leu Ile Lys Ser Val Met
                85                  90                  95

Thr Asn Leu Lys Pro Thr Lys Thr Glu Ile Thr Ala Lys Thr Gly Glu
            100                 105                 110

Lys Asn Pro Glu Gly Glu Val Glu Ile Pro Phe Thr Val Arg Met Thr
        115                 120                 125
```

-continued

```
Leu Pro Gly Ala Gly Glu Tyr Ala Trp Asp Ser Thr Ala Lys Val Val
    130                 135                 140
Gly Gly Gly Lys Glu Trp Lys Val Ala Phe Asn Thr Glu Met Ile His
145                 150                 155                 160
Pro Gln Met Val Pro Gly Gln Thr Leu Ala Leu Lys Ser Arg Glu Arg
                165                 170                 175
Ala Asp Ile Leu Asp Ala Asn Gly Asn Val Leu Gln Ala Ala Ser Ile
            180                 185                 190
Ile Gly Ala Val Asp Pro Arg Thr Gly Lys Gly Ser Ala Gly Leu Gln
        195                 200                 205
Ser Arg Tyr Asp Lys Gln Leu Thr Gly Gly Ser Gly Ala Ala Arg Ser
    210                 215                 220
Val Val Ile Leu Asp Arg Glu Ser Gly Gln Val Val Lys Lys Leu Thr
225                 230                 235                 240
Gly Leu Lys Asp Thr Glu Gly Lys Pro Val Lys Thr Thr Ile Asp Pro
                245                 250                 255
Arg Val Gln Ser Ala Ala Ala Ala Leu Glu Gly Ser Lys Lys Asn
            260                 265                 270
Ala Ala Ile Val Ala Val Asp Pro Ala Thr Gly Asn Ile Leu Ala Ala
        275                 280                 285
Ala Asn Val Pro Ser Gly Met Asn Arg Ala Leu Glu Gly Arg Tyr Pro
    290                 295                 300
Pro Gly Ser Thr Phe Lys Val Val Thr Thr Ala Ala Leu Leu Gln Gln
305                 310                 315                 320
Gly Met Asn Pro Glu Glu Arg Ala Asp Cys Pro Lys Phe Ala His Val
                325                 330                 335
Asn Gly Gln Ser Phe Glu Asn Gln Asp Gln Phe Thr Leu Pro Ala Gly
            340                 345                 350
Ser Thr Phe Arg Asp Ser Phe Ala His Ser Cys Asn Thr Phe Phe Val
    355                 360                 365
Asn Ser Arg Ser Lys Leu Ser Glu Ser Ser Leu Lys Gln Ala Ala Glu
370                 375                 380
Ala Phe Gly Ile Gly Gly Thr Trp Asp Val Gly Ala Ser Thr Phe Asp
385                 390                 395                 400
Gly Ser Val Pro Val Ser Asn Ser Glu Asn Asp Lys Ala Ala Ser Thr
                405                 410                 415
Ile Gly Gln Ala Arg Val Glu Ala Ser Pro Leu Val Met Ala Ser Ile
            420                 425                 430
Ala Ala Thr Val Lys Gln Gly Glu Phe Lys Gln Pro Val Leu Val Pro
        435                 440                 445
Asp Ala Val Lys Lys Pro His Gln Ala Pro Arg Met Ala Pro Gly Ile
    450                 455                 460
Val Asp Ser Leu Arg Ser Met Met Arg Ser Thr Val Thr Asp Gly Ala
465                 470                 475                 480
Gly Asp Ala Leu Arg Gly Leu Gly Gly Gln Pro His Ala Lys Thr Gly
                485                 490                 495
Thr Ala Glu Phe Gly Thr Glu Lys Pro Pro Lys Thr His Ala Trp Met
            500                 505                 510
Ile Gly Tyr Gln Gly Asp Arg Asn Ile Ala Trp Ser Val Leu Leu Glu
        515                 520                 525
```

```
Asp Gly Gly Ser Gly Gly Ala Asp Ala Gly Pro Val Ala Ala Lys Phe
    530                 535                 540

Leu Ser Asn Leu Ala Ala Gly Glx
545                 550

(2) INFORMATION FOR SEQ ID NO: 4:

(i) SEQUENCE CHARACTERISTICS:
        (A) LENGTH: 574 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

Met Ser Arg Val Ser Thr Ala Pro Ser Gly Lys Pro Thr Ala Ala His
1                 5                  10                 15

Ala Leu Leu Ser Arg Leu Arg Asp His Gly Val Gly Lys Val Phe Gly
                 20                  25                 30

Val Val Gly Arg Glu Ala Ala Ser Ile Leu Phe Asp Glu Val Glu Gly
             35                 40                  45

Ile Asp Phe Val Leu Thr Arg His Glu Phe Thr Ala Gly Val Ala Ala
    50                  55                  60

Asp Val Leu Ala Arg Ile Thr Gly Arg Pro Gln Ala Cys Trp Ala Thr
65                  70                  75                  80

Leu Gly Pro Gly Met Thr Asn Leu Ser Thr Gly Ile Ala Thr Ser Val
                 85                  90                  95

Leu Asp Arg Ser Pro Val Ile Ala Leu Ala Ala Gln Ser Glu Ser His
                 100                 105                 110

Asp Ile Phe Pro Asn Asp Thr His Gln Cys Leu Asp Ser Val Ala Ile
            115                 120                 125

Val Ala Pro Met Ser Lys Tyr Ala Val Glu Leu Gln Arg Pro His Glu
            130                 135                 140

Ile Thr Asp Leu Val Asp Ser Ala Val Asn Ala Ala Met Thr Glu Pro
145                 150                 155                 160

Val Gly Pro Ser Phe Ile Ser Leu Pro Val Asp Leu Leu Gly Ser Ser
                165                 170                 175

Glu Gly Ile Asp Thr Thr Val Pro Asn Pro Ala Asn Thr Pro Ala
                180                 185                 190

Lys Pro Val Gly Val Val Ala Asp Gly Trp Gln Lys Ala Ala Asp Gln
            195                 200                 205

Ala Ala Ala Leu Leu Ala Glu Ala Lys His Pro Val Leu Val Val Gly
            210                 215                 220

Ala Ala Ile Arg Ser Gly Ala Val Pro Ala Ile Arg Ala Ile Ala
225                 230                 235                 240

Glu Arg Leu Asn Ile Pro Val Ile Thr Thr Tyr Ile Ala Lys Gly Val
                245                 250                 255

Leu Pro Val Gly His Glu Leu Asn Tyr Gly Ala Val Thr Gly Tyr Met
                260                 265                 270

Asp Gly Ile Leu Asn Phe Pro Ala Leu Gln Thr Met Phe Ala Pro Val
            275                 280                 285

Asp Leu Val Leu Thr Val Gly Tyr Asp Tyr Ala Glu Asp Leu Arg Pro
            290                 295                 300

Ser Met Trp Gln Lys Gly Ile Glu Lys Leu Thr Val Arg Ile Ser Pro
305                 310                 315                 320
```

```
Thr Val Asn Pro Ile Pro Arg Val Tyr Arg Pro Asp Val Asp Val Val
                325                 330                 335

Thr Asp Val Leu Ala Phe Val Glu His Phe Glu Thr Ala Thr Ala Ser
                340                 345                 350

Phe Gly Ala Lys Gln Arg His Asp Ile Glu Pro Leu Arg Ala Arg Ile
                355                 360                 365

Ala Glu Phe Leu Ala Asp Pro Glu Thr Tyr Glu Asp Gly Met Arg Val
                370                 375                 380

His Gln Val Ile Asp Ser Met Asn Thr Val Met Glu Glu Ala Ala Glu
385                 390                 395                 400

Pro Gly Glu Gly Thr Ile Val Ser Asp Ile Gly Phe Phe Arg His Tyr
                405                 410                 415

Gly Val Leu Phe Ala Arg Ala Asp Gln Pro Phe Gly Phe Leu Thr Ser
                420                 425                 430

Ala Gly Cys Ser Ser Phe Gly Tyr Gly Ile Pro Ala Ala Ile Gly Ala
                435                 440                 445

Gln Met Ala Arg Pro Asp Gln Pro Thr Phe Leu Ile Ala Gly Asp Gly
                450                 455                 460

Gly Phe His Ser Asn Ser Ser Asp Leu Glu Thr Ile Ala Arg Leu Asn
465                 470                 475                 480

Leu Pro Ile Val Thr Val Val Asn Asn Asp Thr Asn Gly Leu Ile
                485                 490                 495

Glu Leu Tyr Gln Asn Ile Gly His His Arg Ser His Asp Pro Ala Val
                500                 505                 510

Lys Phe Gly Gly Val Asp Phe Val Ala Leu Ala Glu Ala Asn Gly Val
                515                 520                 525

Asp Ala Thr Arg Ala Thr Asn Arg Glu Glu Leu Leu Ala Ala Leu Arg
                530                 535                 540

Lys Gly Ala Glu Leu Gly Arg Pro Phe Leu Ile Glu Val Pro Val Asn
545                 550                 555                 560

Tyr Asp Phe Gln Pro Gly Gly Phe Gly Ala Leu Ser Ile Glx
                565                 570

(2) INFORMATION FOR SEQ ID NO: 5:

(i) SEQUENCE CHARACTERISTICS:
        (A) LENGTH: 514 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Met Gly Ala Pro Val Leu Pro Ala Ala Phe Gly Phe Leu Ala Ser Ala
1               5                   10                  15

Arg Thr Gly Gly Gly Arg Ala Pro Gly Pro Val Phe Ala Thr Arg Gly
                20                  25                  30

Ser His Thr Asp Ile Asp Thr Pro Gln Gly Glu Arg Ser Leu Ala Ala
                35                  40                  45

Thr Leu Val His Ala Pro Ser Val Ala Pro Asp Arg Ala Val Ala Arg
                50                  55                  60

Ser Leu Thr Gly Ala Pro Thr Thr Ala Val Leu Ala Gly Glu Ile Tyr
65                  70                  75                  80

Asn Arg Asp Glu Leu Leu Ser Val Leu Pro Ala Gly Pro Ala Pro Glu
                85                  90                  95
```

```
Gly Asp Ala Glu Leu Val Leu Arg Leu Leu Glu Arg Tyr Asp Leu His
            100                 105                 110
Ala Phe Arg Leu Val Asn Gly Arg Phe Ala Thr Val Val Arg Thr Gly
            115                 120                 125
Asp Arg Val Leu Leu Ala Thr Asp His Ala Gly Ser Val Pro Leu Tyr
            130                 135             140
Thr Cys Val Ala Pro Gly Glu Val Arg Ala Ser Thr Glu Ala Lys Ala
145                 150                 155                 160
Leu Ala Ala His Arg Asp Pro Lys Gly Phe Pro Leu Ala Asp Ala Arg
                165                 170                 175
Arg Val Ala Gly Leu Thr Gly Val Tyr Gln Val Pro Ala Gly Ala Val
                180                 185                 190
Met Asp Ile Asp Leu Gly Ser Gly Thr Ala Val Thr His Arg Thr Trp
            195                 200                 205
Thr Pro Gly Leu Ser Arg Arg Ile Leu Pro Glu Gly Glu Ala Val Ala
            210                 215                 220
Ala Val Arg Ala Ala Leu Glu Lys Ala Val Ala Gln Arg Val Thr Pro
225                 230                 235                 240
Gly Asp Thr Pro Leu Val Leu Ser Gly Gly Ile Asp Ser Ser Gly
                245                 250                 255
Val Ala Ala Cys Ala His Arg Ala Ala Gly Glu Leu Asp Thr Val Ser
                260                 265                 270
Met Gly Thr Asp Thr Ser Asn Glu Phe Arg Glu Ala Arg Ala Val Val
            275                 280                 285
Asp His Leu Arg Thr Arg His Arg Glu Ile Thr Ile Pro Thr Thr Glu
            290                 295                 300
Leu Leu Ala Gln Leu Pro Tyr Ala Val Trp Ala Ser Glu Ser Val Asp
305                 310                 315                 320
Pro Asp Ile Ile Glu Tyr Leu Leu Pro Leu Thr Ala Leu Tyr Arg Ala
                325                 330                 335
Leu Asp Gly Pro Glu Arg Arg Ile Leu Thr Gly Tyr Gly Ala Asp Ile
                340                 345                 350
Pro Leu Gly Gly Met His Arg Glu Asp Arg Leu Pro Ala Leu Asp Thr
            355                 360                 365
Val Leu Ala His Asp Met Ala Thr Phe Asp Gly Leu Asn Glu Met Ser
            370                 375                 380
Pro Val Leu Ser Thr Leu Ala Gly His Trp Thr Thr His Pro Tyr Trp
385                 390                 395                 400
Asp Arg Glu Val Leu Asp Leu Val Ser Leu Glu Ala Gly Leu Lys
                405                 410                 415
Arg Arg His Gly Arg Asp Lys Trp Val Leu Arg Ala Ala Met Ala Asp
                420                 425                 430
Ala Leu Pro Ala Glu Thr Val Asn Arg Pro Lys Leu Gly Val His Glu
            435                 440                 445
Gly Ser Gly Thr Thr Ser Ser Phe Ser Arg Leu Leu Leu Asp His Gly
            450                 455                 460
Val Ala Glu Asp Arg Val His Glu Ala Lys Arg Gln Val Val Arg Glu
465                 470                 475                 480
Leu Phe Asp Leu Thr Val Gly Gly Arg His Pro Ser Glu Val Asp
                485                 490                 495
Thr Asp Asp Val Val Arg Ser Val Ala Asp Arg Thr Ala Arg Gly Ala
                500                 505                 510
Ala Glx
```

(2) INFORMATION FOR SEQ ID NO: 6:

(i) SEQUENCE CHARACTERISTICS:
        (A) LENGTH: 314 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Val Glu Arg Ile Asp Ser His Val Ser Pro Arg Tyr Ala Gln Ile Pro
1               5                   10                  15

Thr Phe Met Arg Leu Pro His Asp Pro Gln Pro Arg Gly Tyr Asp Val
            20                  25                  30

Val Val Ile Gly Ala Pro Tyr Asp Gly Gly Thr Ser Tyr Arg Pro Gly
        35                  40                  45

Ala Arg Phe Gly Pro Gln Ala Ile Arg Ser Glu Ser Gly Leu Ile His
    50                  55                  60

Gly Val Gly Ile Asp Arg Gly Pro Gly Thr Phe Asp Leu Ile Asn Cys
65                  70                  75                  80

Val Asp Ala Gly Asp Ile Asn Leu Thr Pro Phe Asp Met Asn Ile Ala
                85                  90                  95

Ile Asp Thr Ala Gln Ser His Leu Ser Gly Leu Leu Lys Ala Asn Ala
                100                 105                 110

Ala Phe Leu Met Ile Gly Gly Asp His Ser Leu Thr Val Ala Ala Leu
            115                 120                 125

Arg Ala Val Ala Glu Gln His Gly Pro Leu Ala Val Val His Leu Asp
130                 135                 140

Ala His Ser Asp Thr Asn Pro Ala Phe Tyr Gly Gly Arg Tyr His His
145                 150                 155                 160

Gly Thr Pro Phe Arg His Gly Ile Asp Glu Lys Leu Ile Asp Pro Ala
                165                 170                 175

Ala Met Val Gln Ile Gly Ile Arg Gly His Asn Pro Lys Pro Asp Ser
            180                 185                 190

Leu Asp Tyr Ala Arg Gly His Gly Val Arg Val Thr Ala Asp Glu
        195                 200                 205

Phe Gly Glu Leu Gly Val Gly Thr Ala Asp Leu Ile Arg Glu Lys
    210                 215                 220

Val Gly Gln Arg Pro Val Tyr Val Ser Val Asp Ile Asp Val Val Asp
225                 230                 235                 240

Pro Ala Phe Ala Pro Gly Thr Gly Thr Pro Ala Pro Gly Gly Leu Leu
                245                 250                 255

Ser Arg Glu Val Leu Ala Leu Leu Arg Cys Val Gly Asp Leu Lys Pro
            260                 265                 270

Val Gly Phe Asp Val Met Glu Val Ser Pro Leu Tyr Asp His Gly Gly
        275                 280                 285

Ile Thr Ser Ile Leu Ala Thr Glu Ile Gly Ala Glu Leu Leu Tyr Gln
    290                 295                 300

Tyr Ala Arg Ala His Arg Thr Gln Leu Glx
305                 310
```

(2) INFORMATION FOR SEQ ID NO: 7:

(i) SEQUENCE CHARACTERISTICS:
        (A) LENGTH: 326 amino acids
        (B) TYPE: amino acid

```
        (C) STRANDEDNESS: single
        (D) TOPOLOGY: linear (ii) MOLECULE TYPE: protein (xi) SEQUENCE DESCRIPTION: SEQ ID NO: 7:

Met Ala Ser Pro Ile Val Asp Cys Thr Pro Tyr Arg Asp Glu Leu Leu
1               5                  10                  15

Ala Leu Ala Ser Glu Leu Pro Glu Val Pro Arg Ala Asp Leu His Gly
            20                  25                  30

Phe Leu Asp Glu Ala Lys Thr Leu Ala Ala Arg Leu Pro Glu Gly Leu
        35                  40                  45

Ala Ala Ala Leu Asp Thr Phe Asn Ala Val Gly Ser Glu Asp Gly Tyr
50                  55                  60

Leu Leu Leu Arg Gly Leu Pro Val Asp Asp Ser Glu Leu Pro Glu Thr
65                  70                  75                  80

Pro Thr Ser Thr Pro Ala Pro Leu Asp Arg Lys Arg Leu Val Met Glu
                85                  90                  95

Ala Met Leu Ala Leu Ala Gly Arg Arg Leu Gly Leu His Thr Gly Tyr
            100                 105                 110

Gln Glu Leu Arg Ser Gly Thr Val Tyr His Asp Val Tyr Pro Ser Pro
        115                 120                 125

Gly Ala His Tyr Leu Ser Ser Glu Thr Ser Glu Thr Leu Leu Glu Phe
130                 135                 140

His Thr Glu Met Ala Tyr His Ile Leu Gln Pro Asn Tyr Val Met Leu
145                 150                 155                 160

Ala Cys Ser Arg Ala Asp His Glu Asn Arg Ala Glu Thr Leu Val Gly
            165                 170                 175

Ser Val Arg Lys Ala Leu Pro Leu Leu Asp Glu Lys Thr Arg Ala Arg
        180                 185                 190

Leu Phe Asp Arg Lys Val Pro Cys Cys Val Asp Val Ala Phe Arg Gly
        195                 200                 205

Gly Val Asp Asp Pro Gly Ala Ile Ala Asn Val Lys Pro Leu Tyr Gly
        210                 215                 220

Asp Ala Asn Asp Pro Phe Leu Gly Tyr Asp Arg Glu Leu Leu Ala Pro
225                 230                 235                 240

Glu Asp Pro Ala Asp Lys Glu Ala Val Ala His Leu Ser Gln Ala Leu
            245                 250                 255

Asp Asp Val Thr Val Gly Val Lys Leu Val Pro Gly Asp Val Leu Ile
        260                 265                 270

Ile Asp Asn Phe Arg Thr Thr His Ala Arg Thr Pro Phe Ser Pro Arg
        275                 280                 285

Trp Asp Gly Lys Asp Arg Trp Leu His Arg Val Tyr Ile Arg Thr Asp
290                 295                 300

Arg Asn Gly Gln Leu Ser Gly Gly Glu Arg Ala Gly Asp Thr Ile Ser
305                 310                 315                 320

Phe Ser Pro Arg Arg Glx
                325

(2) INFORMATION FOR SEQ ID NO: 8:

(i) SEQUENCE CHARACTERISTICS:
        (A) LENGTH: 394 amino acids
        (B) TYPE: amino acid
        (C) STRANDEDNESS: single
        (D) TOPOLOGY: linear
```

(ii) MOLECULE TYPE: protein (xi) SEQUENCE DESCRIPTION: SEQ ID NO: 8:

Met Ser Asp Ser Thr Pro Lys Thr Pro Arg Gly Phe Val Val His Thr
1               5                   10                  15

Ala Pro Val Gly Leu Ala Asp Asp Gly Arg Asp Phe Thr Val Leu
            20                  25                  30

Ala Ser Thr Ala Pro Ala Thr Val Ser Ala Val Phe Thr Arg Ser Arg
        35                  40                  45

Phe Ala Gly Pro Ser Val Val Leu Cys Arg Glu Ala Val Ala Asp Gly
    50                  55                  60

Gln Ala Arg Gly Val Val Val Leu Ala Arg Asn Ala Asn Val Ala Thr
65              70                  75                  80

Gly Leu Glu Gly Glu Glu Asn Ala Arg Glu Val Arg Glu Ala Val Ala
                85                  90                  95

Arg Ala Leu Gly Leu Pro Glu Gly Glu Met Leu Ile Ala Ser Thr Gly
            100                 105                 110

Val Ile Gly Arg Gln Tyr Pro Met Glu Ser Ile Arg Glu His Leu Lys
            115                 120                 125

Thr Leu Glu Trp Pro Ala Gly Glu Gly Phe Asp Arg Ala Ala Arg
130             135                 140

Ala Ile Met Thr Thr Asp Thr Arg Pro Lys Glu Val Arg Val Ser Val
145             150                 155                 160

Gly Gly Ala Thr Leu Val Gly Ile Ala Lys Gly Val Gly Met Leu Glu
                165                 170                 175

Pro Asp Met Ala Thr Leu Leu Thr Phe Phe Ala Thr Asp Ala Arg Leu
            180                 185                 190

Asp Pro Ala Glu Gln Asp Arg Leu Phe Arg Arg Val Met Asp Arg Thr
            195                 200                 205

Phe Asn Ala Val Ser Ile Asp Thr Asp Thr Ser Thr Ser Asp Thr Ala
    210                 215                 220

Val Leu Phe Ala Asn Gly Leu Ala Gly Glu Val Asp Ala Gly Glu Phe
225                 230                 235                 240

Glu Glu Ala Leu His Thr Ala Ala Leu Ala Leu Val Lys Asp Ile Ala
                245                 250                 255

Ser Asp Gly Glu Gly Ala Ala Lys Leu Ile Glu Val Gln Val Thr Gly
            260                 265                 270

Ala Arg Asp Asp Ala Gln Ala Lys Arg Val Gly Lys Thr Val Val Asn
            275                 280                 285

Ser Pro Leu Val Lys Thr Ala His Gly Cys Asp Pro Asn Trp Gly
290                 295                 300

Arg Val Ala Met Ala Ile Gly Lys Cys Ser Asp Asp Thr Asp Ile Asp
305             310                 315                 320

Gln Glu Arg Val Thr Ile Arg Phe Gly Glu Val Glu Val Tyr Pro Pro
            325                 330                 335

Lys Ala Arg Gly Asp Gln Ala Asp Ala Leu Arg Ala Ala Val Ala
            340                 345                 350

Glu His Leu Arg Gly Asp Glu Val Val Ile Gly Ile Asp Leu Ala Ile
            355                 360                 365

Ala Asp Gly Ala Phe Thr Val Tyr Gly Cys Asp Leu Thr Glu Gly Tyr
            370                 375                 380

Val Arg Leu Asn Ser Glu Tyr Thr Thr Glx
385                 390

(2) INFORMATION FOR SEQ ID NO: 9:

(i) SEQUENCE CHARACTERISTICS:
        (A) LENGTH: 556 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Glu Thr Thr Arg Ser Thr Thr Ala Asp Glu Gly Phe Asp Ala Gly
 1               5                  10                  15

Val Arg Gly Val Val Ala Pro Thr Asp Ala Pro Gly Gly Thr Leu Arg
             20                  25                  30

Leu Val Arg Thr Asp Asp Phe Asp Ser Leu Asp Pro Gly Asn Thr Tyr
         35                  40                  45

Tyr Ala Tyr Thr Trp Asn Phe Leu Arg Leu Ile Gly Arg Thr Leu Val
     50                  55                  60

Thr Phe Asp Thr Ala Pro Gly Lys Ala Gly Gln Arg Leu Val Pro Asp
 65                  70                  75                  80

Leu Ala Glu Ser Leu Gly Glu Ser Ser Glu Asp Gly Arg Val Trp Thr
                 85                  90                  95

Tyr Arg Leu Arg Glu Gly Leu Arg Tyr Glu Asp Gly Thr Pro Val Val
            100                 105                 110

Ser Ala Asp Ile Lys His Ala Ile Ala Arg Ser Asn Tyr Gly Thr Asp
        115                 120                 125

Val Leu Gly Ala Gly Pro Thr Tyr Phe Arg His Leu Leu Gly Thr Glu
    130                 135                 140

Tyr Gly Gly Pro Trp Arg Glu Pro Asp Ala Asp Gly Pro Val Thr Leu
145                 150                 155                 160

Glu Thr Pro Asp Glu Arg Thr Leu Val Phe Arg Leu Arg Glu Pro Phe
                165                 170                 175

Ala Gly Met Asp Leu Leu Ala Thr Met Pro Ser Thr Thr Pro Val Pro
            180                 185                 190

Arg Asp Arg Asp Thr Gly Ala Glu Tyr Arg Leu Arg Pro Val Ala Thr
        195                 200                 205

Gly Pro Tyr Arg Ile Val Ser Tyr Thr Arg Gly Glu Leu Ala Val Leu
    210                 215                 220

Glu Pro Asn Pro His Trp Asp Pro Glu Thr Asp Pro Val Arg Val Gln
225                 230                 235                 240

Arg Ala Ser Arg Ile Glu Val His Leu Gly Lys Asp Pro His Glu Val
                245                 250                 255

Asp Arg Met Leu Leu Ala Gly Glu Ala His Val Asp Leu Ala Gly Phe
            260                 265                 270

Gly Val Gln Pro Ala Ala Gln Glu Arg Ile Leu Ala Glu Pro Glu Leu
        275                 280                 285

Arg Ala His Ala Asp Asn Pro Leu Thr Gly Phe Thr Trp Ile Tyr Cys
    290                 295                 300

Leu Ser Ser Arg Ile Ala Pro Phe Asp Asn Val His Cys Arg Arg Ala
305                 310                 315                 320

Val Gln Phe Ala Thr Asp Lys Ala Ala Met Gln Glu Ala Tyr Gly Gly
                325                 330                 335

Ala Val Gly Gly Asp Ile Ala Thr Thr Leu Leu Pro Pro Thr Leu Asp
            340                 345                 350
```

-continued

```
Gly Tyr Lys His Phe Asp Arg Tyr Pro Val Gly Pro Glu Gly Thr Gly
            355                 360                 365

Asp Leu Glu Ala Ala Arg Ala Glu Leu Lys Leu Ala Gly Met Pro Asp
370                 375                 380

Gly Phe Arg Thr Arg Ile Ala Ala Arg Lys Asp Arg Leu Lys Glu Tyr
385                 390                 395                 400

Arg Ala Ala Glu Ala Leu Ala Ala Gly Leu Ala Arg Val Gly Ile Glu
                405                 410                 415

Ala Glu Val Leu Asp Phe Pro Ser Gly Asp Tyr Phe Asp Arg Tyr Gly
            420                 425                 430

Gly Cys Pro Glu Tyr Leu Arg Glu His Gly Ile Gly Ile Ile Met Phe
            435                 440                 445

Gly Trp Gly Ala Asp Phe Pro Asp Gly Tyr Gly Phe Leu Gln Gln Ile
450                 455                 460

Thr Asp Gly Arg Ala Ile Lys Glu Arg Gly Asn Gln Asn Met Gly Glu
465                 470                 475                 480

Leu Asp Asp Pro Glu Ile Asn Ala Leu Leu Asp Glu Gly Ala Gln Cys
                485                 490                 495

Ala Asp Pro Ala Arg Arg Ala Glu Ile Trp His Arg Ile Asp Gln Leu
            500                 505                 510

Thr Met Asp His Ala Val Ile Val Pro Tyr Leu Tyr Pro Arg Ser Leu
            515                 520                 525

Leu Tyr Arg His Pro Asp Thr Arg Asn Ala Phe Val Thr Gly Ser Phe
            530                 535                 540

Gly Met Tyr Asp Tyr Val Ala Leu Gly Ala Lys Glx
545                 550                 555
```

(2) INFORMATION FOR SEQ ID NO: 10:

(i) SEQUENCE CHARACTERISTICS:
        (A) LENGTH: 433 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Met Glu Val Ala Arg Arg Thr Gly Val Arg His Gly Thr Val Glu Arg
1               5                   10                  15

Arg Leu Asp Arg Leu Asp Arg Ile Val Gly Leu Pro Leu Thr Leu Arg
            20                  25                  30

Ser Arg His Thr Ala Arg Leu Thr Thr Ala Gly Ser Arg Ile Leu Val
        35                  40                  45

Ala Gly Arg Arg Phe Phe His Gln Val Asp Leu Ala Ala Arg Thr His
50                  55                  60

Ile Phe Gly His Gly Ser Glu Ala Val Asp Ala Pro Glu Val Leu Ser
65                  70                  75                  80

Leu Val Ser Thr Glu Pro Leu Leu Asp Glu Val Val Glu Asp Ala Ala
                85                  90                  95

Ala Ser Leu Asp Leu Leu Leu Ser Val Arg His Glu Ala Pro His Gln
            100                 105                 110

Val Ala Ala Gln Leu Ala Gly Tyr Gln Val Asp Ala Ala Tyr Thr Trp
        115                 120                 125

Ser Leu Gln Ser Pro Arg His Ser Leu Glu Arg Ser Val Arg Thr Cys
130                 135                 140
```

```
Glu Val Leu Asp Asp Pro Leu Trp Val Ile Leu Pro Arg Asp His Pro
145                 150                 155                 160

Leu Ala Ala Arg Arg Glu Val Ser Leu Ala Asp Leu Arg Asp Glu Thr
                165                 170                 175

Trp Val Ser Glu Thr Gly Pro Gly Ser Glu Ile Leu Val Thr Arg Val
            180                 185                 190

Phe Gln Leu Ala Gly Leu Thr Ala Pro Thr Arg Leu His Ile Thr Gly
        195                 200                 205

Ala Ser Val Ala Arg Gly Ile Leu Arg Arg Gly Asp Ala Ile Gly Leu
    210                 215                 220

Gly Ser Pro Thr His Pro Ala Val Gln Asp Pro Ser Leu Val Arg Arg
225                 230                 235                 240

Ser Leu Ala Glu Arg Pro Arg Arg Thr Thr Ser Leu Leu Val Asp Pro
                245                 250                 255

Thr Ile Val Pro Arg Ala Leu Ala Gly Arg Leu Ala Leu Leu Ile Ala
            260                 265                 270

Glu Val Gln Leu Arg Arg Phe Ala Glu His His Arg Asp Leu Leu Asp
        275                 280                 285

Glu Pro Trp Trp Ala Gln Trp Tyr Ala Glu Arg Thr Gly Ala Asp Ala
290                 295                 300

Arg Arg Phe Gly Ala Gly Pro Asp Gln Gly Ser Val Pro Gly Gln Ala
305                 310                 315                 320

Glu Gly Arg Lys Leu Asp Val Asp Asp Leu His Leu Leu Gln Ala Val
                325                 330                 335

Ala Arg His Gly Ser Ile Asn Arg Ala Ala Val Leu Ser Ile Ser
            340                 345                 350

Gln Ser Ala Leu Thr Arg Arg Ile His Arg Leu Glu Gln Ser Leu Gly
        355                 360                 365

Ala Arg Leu Leu Leu Arg Ser Pro Arg Gly Thr Ser Leu Thr Gly Pro
    370                 375                 380

Thr Arg Gln Phe Leu Arg Gln Leu Ala Leu Tyr Glu Ala Glu Phe Arg
385                 390                 395                 400

Glu Ala Ala Leu Ala Cys Arg Ser Val Glu Arg Pro Leu Ala Gln Gly
                405                 410                 415

His Trp Pro Ile Arg Arg Gly Val Ala Ala Gly Ala Arg Met Ser Gly
            420                 425                 430

Glx (2) INFORMATION FOR SEQ ID NO: 11:

(i) SEQUENCE CHARACTERISTICS:
        (A) LENGTH: 248 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

Met Pro Ser Ala Leu Gln Gly Lys Val Ala Leu Ile Thr Gly Ala Ser
1               5                   10                  15

Ser Gly Ile Gly Glu Ala Thr Ala Arg Ala Leu Ala Ala Glu Gly Ala
            20                  25                  30

Ala Val Ala Ile Ala Ala Arg Arg Val Glu Lys Leu Arg Ala Leu Gly
        35                  40                  45
```

-continued

```
Asp Glu Leu Thr Ala Ala Gly Ala Lys Val His Val Leu Glu Leu Asp
         50                  55                  60

Val Ala Asp Arg Gln Gly Val Asp Ala Val Ala Ser Thr Val Glu
 65                  70                  75                  80

Ala Leu Gly Gly Leu Asp Ile Leu Val Asn Asn Ala Gly Ile Met Leu
                     85                  90                  95

Leu Gly Pro Val Glu Asp Ala Asp Thr Thr Asp Trp Thr Arg Met Ile
                100                 105                 110

Asp Thr Asn Leu Leu Gly Leu Met Tyr Met Thr Arg Ala Ala Leu Pro
            115                 120                 125

His Leu Leu Arg Ser Lys Gly Thr Val Val Gln Met Ser Ser Ile Ala
        130                 135                 140

Gly Arg Val Asn Val Arg Asn Ala Ala Val Tyr Gln Ala Thr Lys Phe
145                 150                 155                 160

Gly Val Asn Ala Phe Ser Glu Thr Leu Arg Gln Glu Val Thr Glu Arg
                165                 170                 175

Gly Val Arg Val Val Val Ile Glu Pro Gly Thr Thr Asp Thr Glu Leu
            180                 185                 190

Arg Gly His Ile Thr His Thr Ala Thr Lys Glu Met Tyr Glu Gln Arg
        195                 200                 205

Ile Ser Gln Ile Arg Lys Leu Gln Ala Gln Asp Ile Ala Glu Ala Val
    210                 215                 220

Arg Tyr Ala Val Thr Ala Pro His His Ala Thr Val His Glu Ile Phe
225                 230                 235                 240

Ile Arg Pro Thr Asp Gln Val Glx
                245
```

(2) INFORMATION FOR SEQ ID NO: 12:

(i) SEQUENCE CHARACTERISTICS:
        (A) LENGTH: 409 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

```
Met Met Asn Glu Ala Ala Pro Gln Ser Asp Gln Val Ala Pro Ala Tyr
 1                   5                  10                  15

Pro Met His Arg Val Cys Pro Val Asp Pro Pro Gln Leu Ala Gly
                 20                  25                  30

Leu Arg Ser Gln Lys Ala Ala Ser Arg Val Thr Leu Trp Asp Gly Ser
             35                  40                  45

Gln Val Trp Leu Val Thr Ser His Ala Gly Ala Arg Ala Val Leu Gly
 50                  55                  60

Asp Arg Arg Phe Thr Ala Val Thr Ser Ala Pro Gly Phe Pro Met Leu
 65                  70                  75                  80

Thr Arg Thr Ser Gln Leu Val Arg Ala Asn Pro Glu Ser Ala Ser Phe
                 85                  90                  95

Ile Arg Met Asp Asp Pro Gln His Ser Arg Leu Arg Ser Met Leu Thr
                100                 105                 110

Arg Asp Phe Leu Ala Arg Arg Ala Glu Ala Leu Arg Pro Ala Val Arg
            115                 120                 125

Glu Leu Leu Asp Glu Ile Leu Gly Gly Leu Val Lys Gly Glu Arg Pro
        130                 135                 140
```

```
Val Asp Leu Val Ala Gly Leu Thr Ile Pro Val Pro Ser Arg Val Ile
145                 150                 155                 160

Thr Leu Leu Phe Gly Ala Gly Asp Asp Arg Arg Glu Phe Ile Glu Asp
                165                 170                 175

Arg Ser Ala Val Leu Ile Asp Arg Gly Tyr Thr Pro Glu Gln Val Ala
            180                 185                 190

Lys Ala Arg Asp Glu Leu Asp Gly Tyr Leu Arg Glu Leu Val Glu Glu
        195                 200                 205

Arg Ile Glu Asn Pro Gly Thr Asp Leu Ile Ser Arg Leu Val Ile Asp
    210                 215                 220

Gln Val Arg Pro Gly His Leu Arg Val Glu Glu Met Val Pro Met Cys
225                 230                 235                 240

Arg Leu Leu Leu Val Ala Gly His Gly Thr Thr Thr Ser Gln Ala Ser
                245                 250                 255

Leu Ser Leu Leu Ser Leu Leu Thr Asp Pro Glu Leu Ala Gly Arg Leu
            260                 265                 270

Thr Glu Asp Pro Ala Leu Leu Pro Lys Ala Val Glu Glu Leu Leu Arg
        275                 280                 285

Phe His Ser Ile Val Gln Asn Gly Leu Ala Arg Ala Ala Val Glu Asp
    290                 295                 300

Val Gln Leu Asp Asp Val Leu Ile Arg Ala Gly Glu Gly Val Val Leu
305                 310                 315                 320

Ser Leu Ser Ala Gly Asn Arg Asp Glu Thr Val Phe Pro Asp Pro Asp
                325                 330                 335

Arg Val Asp Val Asp Arg Asp Ala Arg Arg His Leu Ala Phe Gly His
            340                 345                 350

Gly Met His Gln Cys Leu Gly Gln Trp Leu Ala Arg Val Glu Leu Glu
        355                 360                 365

Glu Ile Leu Ala Ala Val Leu Arg Trp Met Pro Gly Ala Arg Leu Ala
    370                 375                 380

Val Pro Phe Glu Glu Leu Asp Phe Arg His Glu Val Ser Ser Tyr Gly
385                 390                 395                 400

Leu Gly Ala Leu Pro Val Thr Trp Glx
                405

(2) INFORMATION FOR SEQ ID NO: 13:

(i) SEQUENCE CHARACTERISTICS:
        (A) LENGTH: 11604 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GAATTCGAGT CATCGGGTTC GGCGACGGAT GGGCGGTTCG GCCACGCACC GTCACTCTTC      60

GTCCCCTCTT CACAAGAACT CCCGATACGT GGAGAAGAGA GCGTGAAGAG CGCGTCCGGT     120

CAGGGTTGCC GAGAACCGTC CACCATGACG GAGCCTGGTA CTGACGGAGT CTGGAGACCG     180

CTCATGTCCC GTGTATCGAC CGCCCCCAGC GGCAAGCCTA CCGCCGCTCA CGCCCTCCTG     240

TCACGGTTGC GTGATCACGG TGTGGGGAAG GTGTTTGGGG TTGTCGGCCG AGAGGCCGCG     300

TCGATTCTCT TCGACGAGGT CGAGGGGATC GACTTCGTTC TGACCCGCCA CGAGTTCACC     360

GCGGGTGTCG CCGCTGATGT CCTCGCGCGG ATCACCGGTC GCCCCAGGC GTGCTGGGCC      420

ACCCTGGGCC CCGGTATGAC CAACCTCTCC ACCGGTATCG CCACGTCCGT CCTGGACCGC     480
```

-continued

```
TCGCCGGTCA TCGCGCTCGC CGCGCAGTCG GAGTCGCACG ACATCTTCCC GAACGACACC    540

CACCAGTGCC TGGACTCGGT GGCGATCGTC GCCCCGATGT CCAAGTACGC CGTGGAGCTC    600

CAGCGGCCCC ACGAGATCAC CGACCTCGTC GACTCCGCCG TGAACGCGGC CATGACCGAG    660

CCGGTCGGGC CCTCCTTCAT CTCCCTCCCG GTGGACCTGC TCGGCTCCTC CGAGGGCATC    720

GACACCACCG TCCCCAACCC GCCGGCGAAC ACCCCGGCGA AACCGGTCGG CGTCGTCGCC    780

GACGGCTGGC AGAAGGCCGC CGACCAGGCC GCCGCCCTGC TCGCCGAGGC CAAGCACCCG    840

GTGCTCGTCG TCGGAGCGGC CGCGATCCGC TCGGGCGCCG TCCCGGCGAT CCGCGCCCTG    900

GCCGAGCGCC TGAACATCCC GGTCATCACG ACCTACATCG CCAAGGGTGT CCTGCCGGTC    960

GGCCACGAGC TGAACTACGG CGCCGTCACC GGCTACATGG ACGGCATCCT CAACTTCCCG   1020

GCGCTCCAGA CCATGTTCGC CCCGGTGGAC CTCGTCCTCA CCGTCGGCTA CGACTACGCC   1080

GAGGACCTGC GCCCGTCCAT GTGGCAGAAG GGCATCGAGA AGAAGACCGT CCGTATCTCC   1140

CCGACGGTCA ACCCGATCCC CCGGGTCTAC CGGCCCGACG TCGACGTCGT CACCGACGTC   1200

CTCGCCTTCG TGGAGCACTT CGAGACCGCG ACCGCCTCCT TCGGGGCCAA GCAGCGCCAC   1260

GACATCGAGC CGCTGCGCGC CCGGATCGCG GAGTTCCTGG CCGACCCGGA GACCTACGAG   1320

GACGGCATGC GCGTCCACCA GGTCATCGAC TCCATGAACA CCGTCATGGA GGAGGCCGCC   1380

GAGCCCGGCG AGGGCACGAT CGTCTCCGAC ATCGGCTTCT TCCGTCACTA CGGTGTGCTC   1440

TTCGCCCGCG CCGACCAGCC CTTCGGCTTC CTCACCTCGG CGGGCTGCTC CAGCTTCGGC   1500

TACGGCATCC CCGCCGCCAT CGGCGCCCAG ATGGCCCGCC GGACCAGCC GACCTTCCTC   1560

ATCGCGGGTG ACGGCGGCTT CCACTCCAAC AGCTCCGACC TGGAGACCAT CGCCCGGCTC   1620

AACCTGCCGA TCGTGACCGT CGTCGTCAAC AACGACACCA ACGGCCTGAT CGAGCTGTAC   1680

CAGAACATCG GTCACCACCG CAGCCACGAC CCGGCGGTCA AGTTCGGCGG CGTCGACTTC   1740

GTCGCGCTCG CCGAGGCCAA CGGTGTCGAC GCCACCCGCG CCACCAACCG CGAGGAGCTG   1800

CTCGCGGCCC TGCGCAAGGG TGCCGAGCTG GGTCGTCCGT TCCTCATCGA GGTCCCGGTC   1860

AACTACGACT TCCAGCCGGG CGGCTTCGGC GCCCTGAGCA TCTGATCATG GGGGCACCGG   1920

TTCTTCCGGC TGCCTTCGGG TTCCTGGCCT CCGCCCGAAC GGGCGGGGGC CGGGCCCCCG   1980

GCCCGGTCTT CGCGACCCGG GGCAGCCACA CCGACATCGA CACGCCCCAG GGGGAGCGCT   2040

CGCTCGCGGC GACCCTGGTG CACGCCCCCT CGGTCGCGCC CGACCGCGCG GTGGCGCGCT   2100

CCCTCACCGG CGCGCCCACC ACCGCGGTGC TCGCCGGTGA GATCTACAAC CGGGACGAAC   2160

TCCTCTCCGT GCTGCCCGCC GGACCCGCGC CGGAGGGGGA CGCGGAGCTG GTCCTGCGGC   2220

TGCTGGAACG CTATGACCTG CATGCCTTCC GGCTGGTGAA CGGGCGCTTC GCGACCGTGG   2280

TGCGGACCGG GGACCGGGTC CTGCTCGCCA CCGACCACGC CGGTTCGGTG CCGCTGTACA   2340

CCTGTGTGGC GCCGGGCGAG GTCCGGGCGT CCACCGAGGC CAAGGCGCTC GCCGCGCACC   2400

GCGACCCGAA GGGCTTCCCG CTCGCGGACG CCCGCCGGGT CGCCGGTCTG ACCGGTGTCT   2460

ACCAGGTGCC CGCGGGCGCC GTGATGGACA TCGACCTCGG CTCGGGCACC GCCGTCACCC   2520

ACCGCACCTG GACCCCGGGC CTCTCCCGCC GCATCCTGCC GGAGGGCGAG GCCGTCGCGG   2580

CCGTGCGGGC CGCGCTGGAG AAGGCCGTCG CCCAGCGGGT CACCCCCGGC GACACCCCGT   2640

TGGTGGTGCT CTCCGGCGGA ATCGACTCCT CCGGGGTCGC GGCCTGTGCG CACCGGGCGG   2700

CCGGGGAACT GGACACGGTG TCCATGGGCA CCGACACGTC CAACGAGTTC CGCGAGGCCC   2760

GGGCGGTCGT CGACCATCTG CGCACCCGGC ACCGGGAGAT CACCATCCCG ACCACCGAGC   2820

TGCTGGCGCA GCTCCCGTAC GCGGTGTGGG CCTCCGAGTC GGTGGACCCG GACATCATCG   2880
```

```
AGTACCTGCT CCCCCTGACA GCGCTCTACC GGGCGCTCGA CGGGCCGGAG CGCCGCATCC    2940

TCACCGGGTA CGGCGCGGAC ATCCCCCTCG GGGGCATGCA CCGCGAGGAC CGGCTGCCCG    3000

CGCTGGACAC CGTTCTCGCG CACGACATGG CCACCTTCGA CGGGCTGAAC GAGATGTCCC    3060

CGGTGCTGTC CACGCTGGCG GGGCACTGGA CCACCCACCC GTACTGGGAC CGGGAGGTCC    3120

TCGATCTGCT GGTCTCGCTG GAGGCCGGGC TCAAGCGGCG GCACGGCCGG GACAAGTGGG    3180

TGCTGCGCGC CGCGATGGCC GACGCCCTCC CGGCGGAGAC CGTCAACCGG CCCAAGCTGG    3240

GCGTCCACGA GGGCTCGGGC ACCACGTCCT CGTTCTCCCG GCTGCTGCTG GACCACGGTG    3300

TCGCCGAGGA CCGCGTCCAC GAGGCGAAGC GGCAGGTGGT GCGCGAGCTG TTCGATCTCA    3360

CGGTCGGGGG CGGACGGCAC CCCTCCGAGG TGGACACCGA CGATGTGGTG CGCTCCGTGG    3420

CCGACCGGAC CGCGCGGGGG GCGGCCTAGT CCCGCCACGG GGAGCCCGCC GGACGCCGGA    3480

CCCGCGCGGG ACCCGTACCC GGGGCCGCCC GCGGACTCCG GCGCACCGGC ACCCCTGTCC    3540

CCCACCCGTT GACGACCGTC GGCCCTCGGC CCTCGCGGCC CCTGACGACC GTCGCCCGAT    3600

TCCCAGGAGG GAGCTGAAAG CGTGGAGCGC ATCGACTCGC ACGTTTCACC CCGCTACGCA    3660

CAGATCCCCA CCTTCATGCG CCTGCCGCAC GATCCCCAGC CCCGCGGCTA TGACGTGGTG    3720

GTCATCGGAG CCCCCTACGA CGGGGGCACC AGCTACCGTC CCGGCGCCCG GTTCGGCCCC    3780

CAGGCCATCC GCAGTGAGTC GGGCCTCATC CACGGTGTCG GCATCGACCG GGGCCCCGGC    3840

ACGTTCGACC TGATCAACTG TGTCGACGCC GGGGACATCA ATCTGACGCC GTTCGACATG    3900

AACATCGCGA TCGACACGGC GCAGAGCCAT CTGTCGGGCC TGCTGAAGGC CAACGCCGCC    3960

TTTCTGATGA TCGGCGGCGA CCACTCGCTG ACGGTGGCCG CCCTGCGCGC GGTCGCGGAG    4020

CAGCACGGCC CGCTCGCCGT GGTGCACCTG GACGCGCACT CCGACACCAA CCCGGCCTTC    4080

TACGGGGGCC GGTACCACCA CGGCACCCCC TTCCGGCACG GGATCGACGA GAAGCTGATC    4140

GACCCGGCGG CGATGGTCCA GATCGGCATC CGGGGCCACA ACCCGAAGCC GGACTCGCTC    4200

GACTACGCCC GGGGCCACGG CGTCCGGGTG GTCACGGCGG ACGAGTTCGG CGAGCTGGGG    4260

GTGGGCGGGA CCGCCGACCT CATCCGCGAG AAGGTCGGCC AGCGGCCCGT GTACGTCTCG    4320

GTCGACATCG ACGTGGTCGA CCCCGCCTTC GCCCCCGGTA CGGGCACGCC CGCGCCGGGC    4380

GGGCTCCTCT CGCGCGAGGT GCTGGCGCTG CTGCGCTGCG TGGGTGACCT GAAGCCGGTC    4440

GGCTTCGACG TGATGGAGGT GTCACCCCTC TACGACCACG GCGGGATCAC TTCGATCCTG    4500

GCCACGGAGA TCGGTGCGGA ACTGCTCTAC CAGTACGCCC GAGCCCACAG AACCCAGTTG    4560

TGAAGGAGAC ATCGTGTCAT GGCCTCTCCG ATAGTTGACT GCACCCCGTA CCGCGACGAG    4620

CTGCTCGCGC TCGCCTCCGA GCTTCCCGAG GTGCCGCGCG CGGACCTCCA TGGCTTCCTC    4680

GACGAGGCGA AGACGCTGGC CGCCCGTCTC CCGGAGGGGC TGGCCGCCGC TCTCGACACC    4740

TTCAACGCCG TGGGCAGCGA GGACGGTTAT CTGCTGCTGC GCGGGCTGCC CGTCGACGAC    4800

AGCGAGCTGC CCGAGACGCC GACCTCCACC CCGGCCCCGC TGGACCGCAA GCGGCTGGTG    4860

ATGGAGGCCA TGCTCGCGCT GGCCGGCCGC CGGCTCGGTC TGCACACGGG GTACCAGGAG    4920

CTGCGCTCGG GCACGGTCTA CCACGACGTG TACCCGTCGC CCGGCGCGCA CTACCTGTCC    4980

TCGGAGACCT CCGAGACGCT GCTGGAGTTC CACACGGAGA TGGCGTACCA CATCCTCCAG    5040

CCGAACTACG TCATGCTGGC CTGCTCCCGC GCGGACCACG AGAACCGGGC GGAGACGCTG    5100

GTCGGCTCGG TCCGCAAGGC GCTGCCCCTG CTGGACGAGA AGACCGGGGC CCGTCTCTTC    5160

GACCGCAAGG TGCCCTGCTG CGTGGACGTG GCCTTCCGCG GCGGGTCGA CGACCCGGGC    5220

GCGATCGCCA ACGTCAAGCC GCTCTACGGG GACGCGAACG ACCCGTTCCT CGGGTACGAC    5280
```

-continued

| | | | | | |
|---|---|---|---|---|---|
| CGCGAGCTGC | TGGCGCCGGA | GGACCCCGCG | GACAAGGAGG | CCGTCGCCCA | TCTGTCCCAG | 5340 |
| GCGCTCGACG | ATGTGACCGT | CGGGGTGAAG | CTCGTCCCCG | GTGACGTCCT | CATCATCGAC | 5400 |
| AACTTCCGCA | CCACGCACGC | GCGGACGCCG | TTCTCGCCCC | GCTGGGACGG | GAAGGACCGC | 5460 |
| TGGCTGCACC | GCGTCTACAT | CCGCACCGAC | CGCAATGGAC | AGCTCTCCGG | CGGCGAGCGC | 5520 |
| GCGGGCGACA | CCATCTCGTT | CTCGCCGCGC | CGCTGAGCCC | GGCTCCCCGA | GGCCCTGGGC | 5580 |
| CCCGGCGCCG | GAACCGGCTC | CCGGTCCTGC | CCCCTCACCC | GCCGCGCGGG | TGAGGGGCA | 5640 |
| GGCCCCTTTG | TGCCGGGTGC | CGTGCGTCCT | GCGAGGGTGC | CGGGGCGGGG | GGGACGGCGG | 5700 |
| AGGTGCCCGG | CGGCCGGGTG | CCGTGCGCCG | CCCGTGGGTG | CTGTACAGCA | CTCCGTGTGC | 5760 |
| CGTGCGCCAC | CCCGTGCATA | AATTTGCCAC | TCTATGGGAA | ATAATGCAGA | GTGCGACGGG | 5820 |
| TGAGGCCGTC | GCCGTGCCCT | TTCCGTGACA | GGAGACGCTG | ACATGTCCGA | CAGCACACCG | 5880 |
| AAGACGCCCC | GGGGATTCGT | GGTGCACACG | GCGCCGGTGG | GCCTGGCCGA | CGACGGCCGC | 5940 |
| GACGACTTCA | CCGTCCTCGC | CTCCACCGCC | CCGGCCACCG | TGAGCGCCGT | CTTCACCCGC | 6000 |
| TCCCGCTTCG | CCGGGCCGAG | CGTCGTGCTG | TGCCGGGAGG | CGGTGGCCGA | CGGGCAGGCG | 6060 |
| CGCGGTGTGG | TGGTGCTGGC | CCGCAACGCG | AATGTCGCGA | CCGGCCTGGA | GGGCGAGGAG | 6120 |
| AACGCGCGCG | AGGTGCGCGA | GGCCGTCGCC | CGGGCCCTCG | GCTGCCGGA | GGGCGAGATG | 6180 |
| CTGATCGCCT | CCACCGGGGT | GATCGGCCGG | CAGTACCCGA | TGGAGAGCAT | CCGGGAGCAC | 6240 |
| CTCAAGACGC | TGGAGTGGCC | CGCCGGGGAG | GGCGGCTTCG | ACCGCGCGG | CCGCGCCATC | 6300 |
| ATGACGACCG | ACACCCGGCC | CAAGGAGGTC | CGGGTCAGCG | TCGGCGGGGC | GACCCTCGTG | 6360 |
| GGCATCGCCA | AGGGCGTCGG | CATGCTGGAG | CCCGACATGG | CGACGCTGCT | GACCTTCTTC | 6420 |
| GCCACGGACG | CCCGGCTGGA | CCCGGCCGAG | CAGGACCGCC | TCTTCCGCCG | GGTCATGGAC | 6480 |
| CGCACCTTCA | ACGCGGTCAG | CATCGACACC | GACACCTCCA | CCAGCGACAC | GGCGGTGCTG | 6540 |
| TTCGCCAACG | GCCTGGCGGG | CGAGGTCGAC | GCCGGGGAGT | TCGAGGAGGC | GCTGCACACG | 6600 |
| GCGGCGCTGG | CCCTGGTCAA | GGACATCGCG | AGCGACGGCG | AGGGCGCGGC | CAAGCTGATC | 6660 |
| GAGGTCCAGG | TCACCGGCGC | CCGCGACGAC | GCCCAGGCCA | AGCGGGTCGG | CAAGACCGTC | 6720 |
| GTCAACTCCC | CGTTGGTGAA | GACCGCCGTG | CACGGCTGCG | ACCCCAACTG | GGGCCGGGTC | 6780 |
| GCCATGGCGA | TCGGCAAGTG | CTCGGACGAC | ACCGACATCG | ACCAGGAGCG | GGTGACGATC | 6840 |
| CGCTTCGGCG | AGGTCGAGGT | CTATCCGCCG | AAGGCCCGGG | GCGACCAGGC | CGACGACGCG | 6900 |
| CTGCGGGCCG | CCGTCGCGGA | GCATCTGCGG | GGCGACGAGG | TGGTCATCGG | GATCGACCTC | 6960 |
| GCCATCGCGG | ACGGGGCCTT | CACCGTCTAC | GGCTGCGACC | TCACCGAGGG | CTATGTCCGG | 7020 |
| CTGAACTCGG | AGTACACCAC | CTGATCCCCG | GACAGGGAAC | GGGCCGCCGC | CCCGTTCCCT | 7080 |
| GTCCGCTCCC | GTCCCGTGTG | GTTATACCGA | CCGTTCCCCG | GCTATGCGCA | CGGGACGGAG | 7140 |
| CGGCCCCCGC | CGGGCCCCGC | CCGGCCGCAC | GATGAGGGGC | GATGCAAGGT | GACGAGGGCA | 7200 |
| GGAGGGACAT | GGAGACCACT | CGGTCGACGA | CCGCGGACGA | GGGCTTCGAC | GCCGGGGTAC | 7260 |
| GGGGAGTGGT | CGCGCCGACC | GACGCCCGG | GCGGACGCT | GCGGCTGGTC | CGCACGGACG | 7320 |
| ACTTCGACTC | GCTCGACCCC | GGCAACACGT | ACTACGCCTA | CACCTGGAAC | TTCCTCCGGC | 7380 |
| TCATCGGCCG | GACGCTGGTC | ACCTTCGACA | CCGCGCCGGG | CAAGGCGGGC | CAGCGGCTCG | 7440 |
| TGCCCGACCT | CGCCGAGTCG | CTGGGCGAGT | CCTCCGAGGA | CGGCCGGGTC | TGGACCTACC | 7500 |
| GGCTGCGCGA | GGGCCTGCGC | TACGAGGACG | GCACGCGGT | CGTCTCGGCC | GACATCAAGC | 7560 |
| ACGCCATCGC | CCGCAGCAAC | TACGGCACCG | ATGTCCTGGG | CGCCGGTCCG | ACCTACTTCC | 7620 |
| GCCACCTCCT | GGGCACCGAG | TACGGCGGCC | CCTGGCGGGA | GCCGGACGCC | GACGGACCGG | 7680 |

```
TGACGCTGGA GACCCCGGAC GAGCGGACGC TGGTCTTCCG GCTGCGGGAG CCGTTCGCGG    7740

GGATGGATCT GCTGGCGACC ATGCCGTCCA CCACCCCCGT GCCGCGCGAC CGGGACACCG    7800

GCGCCGAGTA CCGGCTGCGG CCCGTGGCGA CCGGCCCGTA CCGGATCGTC TCGTACACCC    7860

GGGGCGAGCT GGCCGTCCTG GAGCCCAATC CGCACTGGGA CCCCGAGACC GACCCGGTGC    7920

GCGTCCAGCG CGCCTCCCGG ATCGAGGTGC ACCTCGGCAA GGACCCGCAC GAGGTGGACC    7980

GCATGCTGCT GGCGGGCGAG GCCCATGTGG ACCTCGCGGG CTTCGGTGTG CAGCCCGCGG    8040

CCCAGGAGCG CATCCTCGCC GAGCCGGAGC TGCGCGCGCA CGCGGACAAC CCGCTGACCG    8100

GCTTCACCTG GATCTACTGC CTGTCGAGCC GGATCGCCCC GTTCGACAAT GTGCACTGCC    8160

GGCGGGCCGT GCAGTTCGCC ACCGACAAAG CGGCCATGCA GGAGGCGTAC GGCGGCGCGG    8220

TGGGCGGCGA CATCGCGACC ACCCTGCTGC CCCCGACCCT CGACGGCTAC AAGCACTTCG    8280

ACCGCTACCC GGTCGGCCCC GAGGGCACCG GCGACCTGGA GGCCGCCCGC GCCGAGCTGA    8340

AGCTGGCCGG GATGCCCGAC GGCTTCCGCA CCAGGATCGC CGCCCGCAAG GACCGGCTCA    8400

AGGAGTACCG GGCCGCCGAG GCGCTGGCCG CCGGGCTCGC CCGGGTCGGC ATCGAGGCGG    8460

AGGTGCTGGA CTTCCCGTCG GGCGACTACT TCGACCGCTA CGGCGGCTGC CCGGAGTATC    8520

TGCGCGAGCA CGGGATCGGG ATCATCATGT TCGGCTGGGG CGCCGACTTC CCCGACGGAT    8580

ACGGCTTCCT CCAGCAGATC ACCGACGGGC GCGCGATCAA GGAGCGCGGC AACCAGAACA    8640

TGGGCGAGCT GGACGACCCG GAGATCAACG CGCTGCTGGA CGAGGGGCG CAGTGCGCCG    8700

ACCCGGCGCG GCGCGCGGAG ATCTGGCACC GCATCGACCA GCTCACGATG GACCACGCGG    8760

TCATCGTTCC GTATCTGTAC CCGCGGTCCC TGCTCTACCG GCACCGGGAC ACCCGCAACG    8820

CCTTCGTCAC CGGCTCCTTC GGGATGTACG ACTACGTGGC GCTCGGCGCG AAGTGAGCAC    8880

GGGGTCCGGC CCCGGGACCG TATGTCCCGG GGCCGGACCC CGCCCGTTCC CCGCCCGGTC    8940

CGGTCCGGAC CCGGTCGCGG CCCGCTCAGC CGGACATCCG GGCCCCGGCC GCGACCCCGC    9000

GCCGGATCGG CCAGTGGCCC TGCGCCAGGG GCCGTTCCAC GCTGCGGCAG GCGAGAGCGG    9060

CCTCGCGGAA CTCCGCCTCG TACAGCGCGA GCTGGCGCAG GAACTGCCGG GTCGGGCCGG    9120

TCAGGCTGGT CCCCCGCGGG CTGCGCAGCA GCAGCCGGGC GCCGAGGGAC TGCTCCAGCC    9180

GGTGAATCCG GCGGGTGAGC GCCGACTGGC TGATCGACAG CACCGCCGCG GCCCGGTTGA    9240

TGCTGCCGTG CCGGGCCACG GCCTGGAGCA GATGGAGATC GTCCACATCC AGTTTGCGGC    9300

CCTCGGCCTG GCCGGGCACG GAGCCCTGGT CGGGTCCCGC CCCGAAGCGG CGGGCGTCCG    9360

CGCCGGTGCG CTCCGCGTAC CACTGCGCCC ACCAGGGCTC GTCCAGCAGG TCGCGGTGGT    9420

GTTCGGCGAA GCGCCGGAGC TGGACCTCGG CGATCAGCGC GGCCAGCCGT CCCGCCAGCG    9480

CCCGGGGCAC GATGGTGGGG TCGACGAGCA GACTCGTGGT GCGGCGCGGG CGCTCCGCCA    9540

GGGAGCGGCG CACCAGCGAG GGGTCCTGCA CCGCCGGGTG GGTGGGCGAG CCGAGACCTA    9600

TCGCGTCCCC GCGGCGCAGG ATGCCCCGGG CAACCGATGC CCCCGTGATG TGGAGCCGGG    9660

TGGGCGCGGT GAGCCCGGCC AGCTGGAAGA CACGTGTCAC CAGGATCTCC GAGCCGGGTC    9720

CCGTCTCGGA CACCCAGGTC TCGTCCCGCA GATCGGCGAG CGAGACCTCC CGCCGGGCGG    9780

CCAGCGGATG GTCCCGGGGC AGGATCACCC ACAGCGGGTC GTCCAGCACC TCACAGGTGC    9840

GCACGGACCG CTCCAGGCTG TGCCGGGGGG ACTGGAGGCT CCAGGTGTAG GCCGCGTCCA    9900

CCTGGTAGCC CGCCAGTTGG GCGGCGACCT GGTGCGGGGC CTCGTGCCGG ACCGACAGCA    9960

GCAGGTCCAG CGAGGCCGCC GCGTCCTCCA CCACCTCGTC GAGCAGGGGT TCCGTGGAGA   10020

CCAGCGACAG CACCTCCGGG GCGTCCACGG CCTCGGAGCC ATGGCCGAAG ATATGCGTCC   10080
```

```
GCGCGGCCAG GTCGACCTGG TGGAAGAACC GCCGCCCGGC GACGAGGATG CGGGAGCCCG    10140

CGGTGGTCAG CCGGGCCGTG TGGCGGCTGC GCAGGGTCAG CGGGAGGCCG ACGATCCGGT    10200

CCAGCCGGTC GAGTCTGCGC TCCACGGTGC CGTGCCGGAC ACCCGTCCGC CGGGCCACTT    10260

CCATGAGGTC TCCGCAGTGT CCCACCGCGT CCAGTAAAGA CAGATCGCAT CGGCTGACAC    10320

CAGCAGACGT CGGTTCTGAC CCGAGAGACA ATGTCGGTTC CCTTTTCCGT CAAGGACTGT    10380

ACCGCTGAAT TGTCCGAAGT GGCTCTTGAA TTGCTTCGGA ATCGATCCTA GGCAGCGCCG    10440

CTCTTCGGAT TCTCCTCGCC GGGAAGCGGA ACGCGCCCGG CCGGATGGCG GGCGCGCTCC    10500

GGGCGCCGTC CCGGGAACGG GGGACGGGGC ACGGCACGGC CGGCCACCCG GTCCGGGCGC    10560

GCGGCGTGGA CCTGGTCGGC GGACGGGTGT CAGACCTGGT CGGTGGGCG TATGAAGATC     10620

TCGTGGACGG TCGCGTGGTG CGGCGCGGTC ACGGCGTAGC GGACCGCCTC CGCGATGTCC    10680

TGGGCCTGGA GCTTGCGGAT CTGGCTGATC CGCTGCTCGT ACATCTCCTT GGTGGCGGTG    10740

TGGGTGATGT GGCCGCGCAG CTCCGTGTCG GTGGTGCCCG GCTCGATGAC GACGACCCGC    10800

ACCCCGCGCT CGGTGACCTC CTGGCGCAGC GTCTCGCTGA ACGCGTTCAC ACCGAACTTC    10860

GTGGCCTGGT AGACGGCCGC GTTGCGGACG TTCACCCGGC CCGCGATCGA GGACATCTGC    10920

ACCACGGTGC CCTTGCTGCG CAGCAGATGG GGAAGGGCCG CCCGGGTCAT GTACATCAGG    10980

CCCAGGAGAT TGGTGTCGAT CATCCGGGTC CAGTCGGTGG TGTCGGCGTC CTCCACCGGG    11040

CCGAGCAGCA TGATCCCGGC GTTGTTGACG AGGATGTCGA GGCCGCCCAG CGCCTCGACG    11100

GTGGAGGCGA CGGCGGCGTC CACCCCCTGC CGGTCGGCGA CGTCGAGTTC GAGGACATGG    11160

ACCTTCGCCC CGGCGGCGGT CAGCTCGTCA CCCAGGGCGC GCAGCTTCTC GACCCGGCGC    11220

GCGGCGATGG CCACGGCGGC GCCCTCGGCG CCAGGGCGC GGGCCGTGGC CTCGCCGATG     11280

CCCGAGCTCG CGCCCGTGAT GAGCGCGACT TTCCCCTGGA GTGCGGATGG CATCATTTCC    11340

TCCACATGGT GCTGCGATCG TGGTGAGCGT ATGAAGAAGG GGTGAGACCT GCCGTGCCGG    11400

GGCGGGTTCC GTACGCCGGA CCGTTGCGGT GGGCACGGCC GACCGGGTAC GGATGGCCGC    11460

AGTTCCCCGG GGAGTTCCCG GGGAATGGTG AATACCGCGG CGCTCTCCGA TGGTCTTCGG    11520

AGGACACCCG GGGATTCACC GGGAATCAGC GGCCGGAGTT CTCCCCGTCC ACGGCAGACG    11580

CTATCAGCGT CGCATTCCCC GGTG                                          11604
```

(2) INFORMATION FOR SEQ ID NO: 14:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
TCAGCCGGCC GCGAGGTTGC TGAGGAACTT CGCGGCGACG GGGCCCGCGT CGGCGCCGCC      60

CGACCCGCCG TCCTCCAGCA GGACCGACCA GGCGATGTTC CGGTCGCCCT GGTAGCCGAT     120

CATCCAGGCG TGCGTCTTCG GCGGCTTCTC GGTGCCGAAC TCGGCGGTAC CGGTCTTGGC     180

GTGCGGCTGT CCGCCGAGGC CCCGCAGGGC GTCGCCGGCG CCGTCGGTGA CGGTCGAACG     240

CATCATGGAA CGCAGCGAGT CGACGATGCC CGGGGCCATC CGGGGGGCCT GGTGCGGCTT     300

CTTGACCGCG TCGGGCACCA GCACGGGCTG CTTGAACTCG CCCTGCTTGA CGGTGGCGGC     360

GATGGAGGCC ATCACCAGGG GCGACGCCTC GACCCTGGCC TGTCCGATGG TGGACGCGGC     420
```

```
CTTGTCGTTC TCGCTGTTGG AGACGGGGAC GCTGCCGTCG AAGGTGGAGG CGCCGACGTC    480

CCAGGTGCCG CCGATGCCGA AGGCTTCGGC GGCCTGCTTC AGGCTGGACT CGGAGAGCTT    540

GCTGCGGGAG TTGACGAAGA ACGTGTTGCA GGAGTGGGCG AAGCTGTCCC GGAAGGTCGA    600

GCCCGCGGGC AGCGTGAACT GGTCCTGGTT CTCGAAGCTC TGGCCGTTGA CATGGGCGAA    660

CTTCGGGCAG TCGGCCCGCT CCTCCGGGTT CATCCCCTGC TGGAGCAGGG CCGCGGTGGT    720

GACCACCTTG AAGGTGGAGC CGGGCGGGTA GCGGCCCTCC AGCGCGCGGT TCATGCCGGA    780

GGGCACGTTC GCGGCGGCCA GGATGTTGCC GGTGGCGGGG TCGACGGCGA CGATCGCCGC    840

GTTCTTCTTC GAGCCCTCCA GGGCCGCCGC GGCGGCGGAC TGGACCCGCG GGTCGATGGT    900

GGTCTTCACC GGCTTGCCCT CGGTGTCCTT GAGGCCGGTG AGCTTCTTGA CCACCTGGCC    960

GGACTCACGG TCCAGGATCA CGACCGAGCG CGCCGCGCCG GAGCCGCCGG TGAGCTGCTT   1020

GTCGTAGCGG GACTGGAGGC CCGCCGAGCC CTTGCCGGTC CTGGGGTCGA CCGCGCCGAT   1080

GATGGAGGCG GCCTGGAGGA CATTGCCGTT GGCGTCGAGG ATGTCCGCGC GCTCCCGCGA   1140

CTTGAGGGCA AGGGTCTGCC CCGGAACCAT CTGCGGATGG ATCATCTCGG TGTTGAACGC   1200

GACCTTCCAC TCCTTGCCGC CGCCGACGAC CTTCGCGGTG GAGTCCCAGG CGTACTCCCC   1260

GGCCCCGGGG AGGGTCATTC TGACGGTGAA CGGTATCTCC ACCTCGCCCT CGGGGTTCTT   1320

CTCCCCGGTC TTGGCGGTGA TCTCCGTCTT CGTCGGCTTG AGGTTGGTCA TGACGGATTT   1380

GATCAGCGAC TCGGCGTTGT CCGGGGTGTC CGTCAGCCCG GCGGCCGTCG GGGCGTCGCC   1440

CTTCTCCCAG GCGCCGAGGA AGGTGTCGAA CTGTCCGGCC GCCGCCTCCA CCTCGGGGTC   1500

GCCCGAATCC TTCTCGTCGG CAACCAGGCT GGTGTAACCC CAATAGCCGA GCCCCACCGT   1560

CACGGCCAGC CCGGCGACCA CCGCGGTGGC CGCCCGGCCA CGGGAGCGGC GCCTGCCCTG   1620

CGGCGGGTCA TCGCCATAGT TGTCGGAATG CGTCAT                             1656
```

(2) INFORMATION FOR SEQ ID NO: 15:

(i) SEQUENCE CHARACTERISTICS:
        (A) LENGTH: 1722 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
ATGTCCCGTG TATCGACCGC CCCCAGCGGC AAGCCTACCG CCGCTCACGC CCTCCTGTCA     60

CGGTTGCGTG ATCACGGTGT GGGGAAGGTG TTTGGGGTTG TCGGCCGAGA GGCCGCGTCG    120

ATTCTCTTCG ACGAGGTCGA GGGGATCGAC TTCGTTCTGA CCCGCCACGA GTTCACCGCG    180

GGTGTCGCCG CTGATGTCCT CGCGCGGATC ACCGGTCGCC CCCAGGCGTG CTGGGCCACC    240

CTGGGCCCCG GTATGACCAA CCTCTCCACC GGTATCGCCA CGTCCGTCCT GGACCGCTCG    300

CCGGTCATCG CGCTCGCCGC GCAGTCGGAG TCGCACGACA TCTTCCCGAA CGACACCCAC    360

CAGTGCCTGG ACTCGGTGGC GATCGTCGCC CCGATGTCCA AGTACGCCGT GGAGCTCCAG    420

CGGCCCCACG AGATCACCGA CCTCGTCGAC TCCGCCGTGA ACGCGGCCAT GACCGAGCCG    480

GTCGGGCCCT CCTTCATCTC CCTCCCGGTG GACCTGCTCG GCTCCTCCGA GGGCATCGAC    540

ACCACCGTCC CCAACCCGCC GGCGAACACC CCGGCGAAAC CGGTCGGCGT CGTCGCCGAC    600

GGCTGGCAGA AGGCCGCCGA CCAGGCCGCC GCCCTGCTCG CCGAGGCCAA GCACCCGGTG    660

CTCGTCGTCG GAGCGGCCGC GATCCGCTCG GGCGCCGTCC CGGCGATCCG CGCCCTGGCC    720
```

```
GAGCGCCTGA ACATCCCGGT CATCACGACC TACATCGCCA AGGGTGTCCT GCCGGTCGGC        780

CACGAGCTGA ACTACGGCGC CGTCACCGGC TACATGGACG GCATCCTCAA CTTCCCGGCG        840

CTCCAGACCA TGTTCGCCCC GGTGGACCTC GTCCTCACCG TCGGCTACGA CTACGCCGAG        900

GACCTGCGCC CGTCCATGTG GCAGAAGGGC ATCGAGAAGA AGACCGTCCG TATCTCCCCG        960

ACGGTCAACC CGATCCCCCG GGTCTACCGG CCCGACGTCG ACGTCGTCAC CGACGTCCTC       1020

GCCTTCGTGG AGCACTTCGA GACCGCGACC GCCTCCTTCG GGGCCAAGCA GCGCCACGAC       1080

ATCGAGCCGC TGCGCGCCCG GATCGCGGAG TTCCTGGCCG ACCCGGAGAC CTACGAGGAC       1140

GGCATGCGCG TCCACCAGGT CATCGACTCC ATGAACACCG TCATGGAGGA GGCCGCCGAG       1200

CCCGGCGAGG GCACGATCGT CTCCGACATC GGCTTCTTCC GTCACTACGG TGTGCTCTTC       1260

GCCCGCGCCG ACCAGCCCTT CGGCTTCCTC ACCTCGGCGG GCTGCTCCAG CTTCGGCTAC       1320

GGCATCCCCG CCGCCATCGG CGCCCAGATG GCCCGCCCGG ACCAGCCGAC CTTCCTCATC       1380

GCGGGTGACG GCGGCTTCCA CTCCAACAGC TCCGACCTGG AGACCATCGC CCGGCTCAAC       1440

CTGCCGATCG TGACCGTCGT CGTCAACAAC GACACCAACG GCCTGATCGA GCTGTACCAG       1500

AACATCGGTC ACCACCGCAG CCACGACCCG GCGGTCAAGT TCGGCGGCGT CGACTTCGTC       1560

GCGCTCGCCG AGGCCAACGG TGTCGACGCC ACCCGCGCCA CCAACCGCGA GGAGCTGCTC       1620

GCGGCCCTGC GCAAGGGTGC CGAGCTGGGT CGTCCGTTCC TCATCGAGGT CCCGGTCAAC       1680

TACGACTTCC AGCCGGGCGG CTTCGGCGCC CTGAGCATCT GA                         1722

(2) INFORMATION FOR SEQ ID NO: 16:

(i) SEQUENCE CHARACTERISTICS:
        (A) LENGTH: 1542 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

ATGGGGGCAC CGGTTCTTCC GGCTGCCTTC GGGTTCCTGG CCTCCGCCCG AACGGGCGGG         60

GGCCGGGCCC CCGGCCCGGT CTTCGCGACC CGGGGCAGCC ACACCGACAT CGACACGCCC        120

CAGGGGGAGC GCTCGCTCGC GGCGACCCTG GTGCACGCCC CCTCGGTCGC GCCCGACCGC        180

GCGGTGGCGC GCTCCCTCAC CGGCGCGCCC ACCACCGCGG TGCTCGCCGG TGAGATCTAC        240

AACCGGGACG AACTCCTCTC CGTGCTGCCC GCCGGACCCG CGCCGGAGGG GGACGCGGAG        300

CTGGTCCTGC GGCTGCTGGA ACGCTATGAC CTGCATGCCT TCCGGCTGGT GAACGGGCGC        360

TTCGCGACCG TGGTGCGGAC CGGGGACCGG GTCCTGCTCG CCACCGACCA CGCCGGTTCG        420

GTGCCGCTGT ACACCTGTGT GGCGCCGGGC GAGGTCCGGG CGTCCACCGA GGCCAAGGCG        480

CTCGCCGCGC ACCGCGACCC GAAGGGCTTC CCGCTCGCGG ACGCCCGCCG GGTCGCCGGT        540

CTGACCGGTG TCTACCAGGT GCCCGCGGGC GCCGTGATGG ACATCGACCT CGGCTCGGGC        600

ACCGCCGTCA CCCACCGCAC CTGGACCCCG GGCCTCTCCC GCCGCATCCT GCCGGAGGGC        660

GAGGCCGTCG CGGCCGTGCG GGCCGCGCTG GAGAAGGCCG TCGCCCAGCG GGTCACCCCC        720

GGCGACACCC CGTTGGTGGT GCTCTCCGGC GGAATCGACT CCTCCGGGGT CGCGGCCTGT        780

GCGCACCGGG CGGCCGGGGA ACTGGACACG GTGTCCATGG CACCGACAC GTCCAACGAG        840

TTCCGCGAGG CCCGGGCGGT CGTCGACCAT CTGCGCACCC GGCACCGGGA GATCACCATC        900

CCGACCACCG AGCTGCTGGC GCAGCTCCCG TACGCGGTGT GGGCCTCCGA GTCGGTGGAC        960
```

```
CCGGACATCA TCGAGTACCT GCTCCCCCTG ACAGCGCTCT ACCGGGCGCT CGACGGGCCG     1020

GAGCGCCGCA TCCTCACCGG GTACGGCGCG GACATCCCCC TCGGGGGCAT GCACCGCGAG     1080

GACCGGCTGC CCGCGCTGGA CACCGTTCTC GCGCACGACA TGGCCACCTT CGACGGGCTG     1140

AACGAGATGT CCCCGGTGCT GTCCACGCTG GCGGGGCACT GGACCACCCA CCCGTACTGG     1200

GACCGGGAGG TCCTCGATCT GCTGGTCTCG CTGGAGGCCG GGCTCAAGCG GCGGCACGGC     1260

CGGGACAAGT GGGTGCTGCG CGCCGCGATG GCCGACGCCC TCCCGGCGGA GACCGTCAAC     1320

CGGCCCAAGC TGGGCGTCCA CGAGGGCTCG GGCACCACGT CCTCGTTCTC CCGGCTGCTG     1380

CTGGACCACG GTGTCGCCGA GGACCGCGTC CACGAGGCGA AGCGGCAGGT GGTGCGCGAG     1440

CTGTTCGATC TCACGGTCGG GGGCGGACGG CACCCCTCCG AGGTGGACAC CGACGATGTG     1500

GTGCGCTCCG TGGCCGACCG GACCGCGCGG GGGGCGGCCT AG                       1542

(2) INFORMATION FOR SEQ ID NO: 17:

(i) SEQUENCE CHARACTERISTICS:
        (A) LENGTH: 942 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GTGGAGCGCA TCGACTCGCA CGTTTCACCC CGCTACGCAC AGATCCCCAC CTTCATGCGC       60

CTGCCGCACG ATCCCCAGCC CGCGGCTAT GACGTGGTGG TCATCGGAGC CCCCTACGAC       120

GGGGGCACCA GCTACCGTCC CGGCGCCCGG TTCGGCCCCC AGGCCATCCG CAGTGAGTCG      180

GGCCTCATCC ACGGTGTCGG CATCGACCGG GGCCCCGGCA CGTTCGACCT GATCAACTGT      240

GTCGACGCCG GGGACATCAA TCTGACGCCG TTCGACATGA ACATCGCGAT CGACACGGCG      300

CAGAGCCATC TGTCGGGCCT GCTGAAGGCC AACGCCGCCT TTCTGATGAT CGGCGGCGAC      360

CACTCGCTGA CGGTGGCCGC CCTGCGCGCG GTCGCGGAGC AGCACGGCCC GCTCGCCGTG      420

GTGCACCTGG ACGCGCACTC CGACACCAAC CCGGCCTTCT ACGGGGCCG GTACCACCAC       480

GGCACCCCCT TCCGGCACGG GATCGACGAG AAGCTGATCG ACCCGGCGGC GATGGTCCAG      540

ATCGGCATCC GGGGCCACAA CCCGAAGCCG GACTCGCTCG ACTACGCCCG GGGCCACGGC      600

GTCCGGGTGG TCACGGCGGA CGAGTTCGGC GAGCTGGGGG TGGGCGGGAC CGCCGACCTC      660

ATCCGCGAGA AGGTCGGCCA GCGGCCCGTG TACGTCTCGG TCGACATCGA CGTGGTCGAC      720

CCCGCCTTCG CCCCCGGTAC GGGCACGCCC GCGCCGGGCG GCTCCTCTC GCGCGAGGTG       780

CTGGCGCTGC TGCGCTGCGT GGGTGACCTG AAGCCGGTCG GCTTCGACGT GATGGAGGTG      840

TCACCCCTCT ACGACCACGG CGGGATCACT TCGATCCTGG CCACGGAGAT CGGTGCGGAA     900

CTGCTCTACC AGTACGCCCG AGCCCACAGA ACCCAGTTGT GA                        942

(2) INFORMATION FOR SEQ ID NO: 18:

(i) SEQUENCE CHARACTERISTICS:
        (A) LENGTH: 978 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

ATGGCCTCTC CGATAGTTGA CTGCACCCCG TACCGCGACG AGCTGCTCGC GCTCGCCTCC       60
```

-continued

```
GAGCTTCCCG AGGTGCCGCG CGCGGACCTC CATGGCTTCC TCGACGAGGC GAAGACGCTG      120

GCCGCCCGTC TCCCGGAGGG GCTGGCCGCC GCTCTCGACA CCTTCAACGC CGTGGGCAGC      180

GAGGACGGTT ATCTGCTGCT GCGCGGGCTG CCCGTCGACG ACAGCGAGCT GCCCGAGACG      240

CCGACCTCCA CCCCGGCCCC GCTGGACCGC AAGCGGCTGG TGATGGAGGC CATGCTCGCG      300

CTGGCCGGCC GCCGGCTCGG TCTGCACACG GGGTACCAGG AGCTGCGCTC GGGCACGGTC      360

TACCACGACG TGTACCCGTC GCCCGGCGCG CACTACCTGT CCTCGGAGAC CTCCGAGACG      420

CTGCTGGAGT TCCACACGGA GATGGCGTAC CACATCCTCC AGCCGAACTA CGTCATGCTG      480

GCCTGCTCCC GCGCGGACCA CGAGAACCGG GCGGAGACGC TGGTCGGCTC GGTCCGCAAG      540

GCGCTGCCCC TGCTGGACGA GAAGACCCGG GCCCGTCTCT TCGACCGCAA GGTGCCCTGC      600

TGCGTGGACG TGGCCTTCCG CGGCGGGGTC GACGACCCGG GCGCGATCGC CAACGTCAAG      660

CCGCTCTACG GGGACGCGAA CGACCCGTTC CTCGGGTACG ACCGCGAGCT GCTGGCGCCG      720

GAGGACCCCG CGGACAAGGA GGCCGTCGCC CATCTGTCCC AGGCGCTCGA CGATGTGACC      780

GTCGGGGTGA AGCTCGTCCC CGGTGACGTC CTCATCATCG ACAACTTCCG CACCACGCAC      840

GCGCGGACGC CGTTCTCGCC CCGCTGGGAC GGGAAGGACC GCTGGCTGCA CCGCGTCTAC      900

ATCCGCACCG ACCGCAATGG ACAGCTCTCC GGCGGCGAGC GCGCGGGCGA CACCATCTCG      960

TTCTCGCCGC GCCGCTGA                                                    978
```

(2) INFORMATION FOR SEQ ID NO: 19:

(i) SEQUENCE CHARACTERISTICS:
        (A) LENGTH: 1182 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
ATGTCCGACA GCACACCGAA GACGCCCCGG GGATTCGTGG TGCACACGGC GCCGGTGGGC       60

CTGGCCGACG ACGGCCGCGA CGACTTCACC GTCCTCGCCT CCACCGCCCC GGCCACCGTG      120

AGCGCCGTCT TCACCCGCTC CCGCTTCGCC GGGCCGAGCG TCGTGCTGTG CCGGGAGGCG      180

GTGGCCGACG GGCAGGCGCG CGGTGTGGTG GTGCTGGCCC GCAACGCGAA TGTCGCGACC      240

GGCCTGGAGG GCGAGGAGAA CGCGCGCGAG GTGCGCGAGG CCGTCGCCCG GGCCCTCGGG      300

CTGCCGGAGG GCGAGATGCT GATCGCCTCC ACCGGGGTGA TCGGCCGGCA GTACCCGATG      360

GAGAGCATCC GGGAGCACCT CAAGACGCTG GAGTGGCCCG CCGGGGAGGG CGGCTTCGAC      420

CGCGCGGCCC GCGCCATCAT GACGACCGAC ACCCGGCCCA AGGAGGTCCG GGTCAGCGTC      480

GGCGGGGCGA CCCTCGTGGG CATCGCCAAG GGCGTCGGCA TGCTGGAGCC CGACATGGCG      540

ACGCTGCTGA CCTTCTTCGC CACGGACGCC CGGCTGGACC CGGCCGAGCA GGACCGCCTC      600

TTCCGCCGGG TCATGGACCG CACCTTCAAC GCGGTCAGCA TCGACACCGA CACCTCCACC      660

AGCGACACGG CGGTGCTGTT CGCCAACGGC CTGGCGGGCG AGGTCGACGC CGGGGAGTTC      720

GAGGAGGCGC TGCACACGGC GGCGCTGGCC CTGGTCAAGG ACATCGCGAG CGACGGCGAG      780

GGCGCGGCCA AGCTGATCGA GGTCCAGGTC ACCGGCGCCC GCGACGACGC CCAGGCCAAG      840

CGGGTCGGCA AGACCGTCGT CAACTCCCCG TTGGTGAAGA CCGCCGTGCA CGGCTGCGAC      900

CCCAACTGGG GCCGGGTCGC CATGGCGATC GGCAAGTGCT CGGACGACAC CGACATCGAC      960

CAGGAGCGGG TGACGATCCG CTTCGGCGAG GTCGAGGTCT ATCCGCCGAA GGCCCGGGGC     1020
```

```
GACCAGGCCG ACGACGCGCT GCGGGCCGCC GTCGCGGAGC ATCTGCGGGG CGACGAGGTG    1080

GTCATCGGGA TCGACCTCGC CATCGCGGAC GGGGCCTTCA CCGTCTACGG CTGCGACCTC    1140

ACCGAGGGCT ATGTCCGGCT GAACTCGGAG TACACCACCT GA                      1182
```

(2) INFORMATION FOR SEQ ID NO: 20:

(i) SEQUENCE CHARACTERISTICS:
        (A) LENGTH: 1668 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
ATGGAGACCA CTCGGTCGAC GACCGCGGAC GAGGGCTTCG ACGCCGGGGT ACGGGGAGTG      60

GTCGCGCCGA CCGACGCCCC GGGCGGGACG CTGCGGCTGG TCCGCACGGA CGACTTCGAC     120

TCGCTCGACC CCGGCAACAC GTACTACGCC TACACCTGGA ACTTCCTCCG GCTCATCGGC     180

CGGACGCTGG TCACCTTCGA CACCGCGCCG GGCAAGGCGG CCAGCGGCT CGTGCCCGAC      240

CTCGCCGAGT CGCTGGGCGA GTCCTCCGAG GACGGCCGGG TCTGGACCTA CCGGCTGCGC     300

GAGGGCCTGC GCTACGAGGA CGGCACGCCG GTCGTCTCGG CCGACATCAA GCACGCCATC     360

GCCCGCAGCA ACTACGGCAC CGATGTCCTG GGCGCCGGTC CGACCTACTT CCGCCACCTC     420

CTGGGCACCG AGTACGGCGG CCCCTGGCGG GAGCCGGACG CCGACGGACC GGTGACGCTG     480

GAGACCCCGG ACGAGCGGAC GCTGGTCTTC CGGCTGCGGG AGCCGTTCGC GGGGATGGAT     540

CTGCTGGCGA CCATGCCGTC CACCACCCCC GTGCCGCGCG ACCGGGACAC CGGCGCCGAG     600

TACCGGCTGC GGCCCGTGGC GACCGGCCCG TACCGGATCG TCTCGTACAC CCGGGGCGAG     660

CTGGCCGTCC TGGAGCCCAA TCCGCACTGG GACCCCGAGA CCGACCCGGT GCGCGTCCAG     720

CGCGCCTCCC GGATCGAGGT GCACCTCGGC AAGGACCCGC ACGAGGTGGA CCGCATGCTG     780

CTGGCGGGCG AGGCCCATGT GGACCTCGCG GGCTTCGGTG TGCAGCCCGC GGCCCAGGAG     840

CGCATCCTCG CCGAGCCGGA GCTGCGCGCG CACGCGGACA ACCCGCTGAC CGGCTTCACC     900

TGGATCTACT GCCTGTCGAG CCGGATCGCC CCGTTCGACA ATGTGCACTG CCGGCGGGCC     960

GTGCAGTTCG CCACCGACAA AGCGGCCATG CAGGAGGCGT ACGGCGGCGC GGTGGGCGGC    1020

GACATCGCGA CCACCCTGCT GCCCCCGACC CTCGACGGCT ACAAGCACTT CGACCGCTAC    1080

CCGGTCGGCC CCGAGGGCAC CGGCGACCTG GAGGCCGCCC GCGCCGAGCT GAAGCTGGCC    1140

GGGATGCCCG ACGGCTTCCG CACCAGGATC GCCGCCCGCA AGGACCGGCT CAAGGAGTAC    1200

CGGGCCGCCG AGGCGCTGGC CGCCGGGCTC GCCCGGGTCG GCATCGAGGC GGAGGTGCTG    1260

GACTTCCCGT CGGGCGACTA CTTCGACCGC TACGGCGGCT GCCCGGAGTA TCTGCGCGAG    1320

CACGGGATCG GATCATCAT GTTCGGCTGG GGCGCCGACT TCCCCGACGG ATACGGCTTC    1380

CTCCAGCAGA TCACCGACGG GCGCGCGATC AAGGAGCGCG GCAACCAGAA CATGGGCGAG    1440

CTGGACGACC CGGAGATCAA CGCGCTGCTG GACGAGGGGG CGCAGTGCGC CGACCCGGCG    1500

CGGCGCGCGG AGATCTGGCA CCGCATCGAC CAGCTCACGA TGGACCACGC GGTCATCGTT    1560

CCGTATCTGT ACCCGCGGTC CCTGCTCTAC CGGCACCCGG ACACCCGCAA CGCCTTCGTC    1620

ACCGGCTCCT TCGGGATGTA CGACTACGTG GCGCTCGGCG CGAAGTGA                1668
```

(2) INFORMATION FOR SEQ ID NO: 21:

(i) SEQUENCE CHARACTERISTICS:
        (A) LENGTH: 1299 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
TCAGCCGGAC ATCCGGGCCC CGGCCGCGAC CCCGCGCCGG ATCGGCCAGT GGCCCTGCGC      60

CAGGGGCCGT TCCACGCTGC GGCAGGCGAG AGCGGCCTCG CGGAACTCCG CCTCGTACAG     120

CGCGAGCTGG CGCAGGAACT GCCGGGTCGG GCCGGTCAGG CTGGTCCCCC GCGGGCTGCG     180

CAGCAGCAGC CGGGCGCCGA GGGACTGCTC CAGCCGGTGA ATCCGGCGGG TGAGCGCCGA     240

CTGGCTGATC GACAGCACCG CCGCGGCCCG GTTGATGCTG CCGTGCCGGG CCACGGCCTG     300

GAGCAGATGG AGATCGTCCA CATCCAGTTT GCGGCCCTCG GCCTGGCCGG GCACGGAGCC     360

CTGGTCGGGT CCCGCCCCGA AGCGGCGGGC GTCCGCGCCG GTGCGCTCCG CGTACCACTG     420

CGCCCACCAG GGCTCGTCCA GCAGGTCGCG GTGGTGTTCG GCGAAGCGCC GGAGCTGGAC     480

CTCGGCGATC AGCGCGGCCA GCCGTCCCGC CAGCGCCCGG GGCACGATGG TGGGGTCGAC     540

GAGCAGACTC GTGGTGCGGC GCGGGCGCTC CGCCAGGGAG CGGCGCACCA GCGAGGGGTC     600

CTGCACCGCC GGGTGGGTGG GCGAGCCGAG ACCTATCGCG TCCCCGCGGC GCAGGATGCC     660

CCGGGCAACC GATGCCCCCG TGATGTGGAG CCGGGTGGGC GCGGTGAGCC CGGCCAGCTG     720

GAAGACACGT GTCACCAGGA TCTCCGAGCC GGGTCCCGTC TCGGACACCC AGGTCTCGTC     780

CCGCAGATCG GCGAGCGAGA CCTCCCGCCG GGCGGCCAGC GGATGGTCCC GGGGCAGGAT     840

CACCCACAGC GGGTCGTCCA GCACCTCACA GGTGCGCACG GACCGCTCCA GGCTGTGCCG     900

GGGGGACTGG AGGCTCCAGG TGTAGGCCGC GTCCACCTGG TAGCCCGCCA GTTGGGCGGC     960

GACCTGGTGC GGGGCCTCGT GCCGGACCGA CAGCAGCAGG TCCAGCGAGG CCGCCGCGTC    1020

CTCCACCACC TCGTCGAGCA GGGGTTCCGT GGAGACCAGC GACAGCACCT CCGGGGCGTC    1080

CACGGCCTCG GAGCCATGGC CGAAGATATG CGTCCGCGCG GCCAGGTCGA CCTGGTGGAA    1140

GAACCGCCGC CCGGCGACGA GGATGCGGGA GCCCGCGGTG GTCAGCCGGG CCGTGTGGCG    1200

GCTGCGCAGG GTCAGCGGGA GGCCGACGAT CCGGTCCAGC CGGTCGAGTC TGCGCTCCAC    1260

GGTGCCGTGC CGGACACCCG TCCGCCGGGC CACTTCCAT                           1299
```

(2) INFORMATION FOR SEQ ID NO: 22:

(i) SEQUENCE CHARACTERISTICS:
        (A) LENGTH: 744 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
TCAGACCTGG TCGGTGGGGC GTATGAAGAT CTCGTGGACG GTCGCGTGGT GCGGCGCGGT      60

CACGGCGTAG CGGACCGCCT CCGCGATGTC CTGGGCCTGG AGCTTGCGGA TCTGGCTGAT     120

CCGCTGCTCG TACATCTCCT TGGTGGCGGT GTGGGTGATG TGGCCGCGCA GCTCCGTGTC     180

GGTGGTGCCC GGCTCGATGA CGACGACCCG CACCCCGCGC TCGGTGACCT CCTGGCGCAG     240

CGTCTCGCTG AACGCGTTCA CACCGAACTT CGTGGCCTGG TAGACGGCCG CGTTGCGGAC     300
```

```
GTTCACCCGG CCCGCGATCG AGGACATCTG CACCACGGTG CCCTTGCTGC GCAGCAGATG    360

GGGAAGGGCC GCCCGGGTCA TGTACATCAG GCCCAGGAGA TTGGTGTCGA TCATCCGGGT    420

CCAGTCGGTG GTGTCGGCGT CCTCCACCGG GCCGAGCAGC ATGATCCCGG CGTTGTTGAC    480

GAGGATGTCG AGGCCGCCCA GCGCCTCGAC GGTGGAGGCG ACGGCGGCGT CCACCCCCTG    540

CCGGTCGGCG ACGTCGAGTT CGAGGACATG GACCTTCGCC CCGGCGGCGG TCAGCTCGTC    600

ACCCAGGGCG CGCAGCTTCT CGACCCGGCG CGCGGCGATG GCCACGGCGG CGCCCTCGGC    660

GGCCAGGGCG CGGGCCGTGG CCTCGCCGAT GCCCGAGCTC GCGCCCGTGA TGAGCGCGAC    720

TTTCCCCTGG AGTGCGGATG GCAT                                          744

(2) INFORMATION FOR SEQ ID NO: 23:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

ATGATGAACG AGGCAGCGCC TCAGTCCGAC CAGGTGGCAC CGGCGTATCC GATGCACCGG     60

GTCTGCCCGG TCGACCCGCC GCCGCAACTG GCCGGGCTGC GGTCCCAGAA GGCCGCGAGC    120

CGGGTGACGC TGTGGGACGG CAGCCAGGTG TGGCTGGTGA CCTCGCACGC CGGGGCCCGG    180

GCCGTCCTGG GCGACCGCCG CTTCACCGCG GTGACGAGCG CGCCCGGCTT CCCGATGCTG    240

ACCCGCACCT CCCAACTGGT GCGCGCCAAC CCGGAGTCGG CGTCGTTCAT CCGCATGGAC    300

GACCCGCAGC ACTCCCGGCT GCGCTCGATG CTCACCCGGG ACTTCCTGGC CCGCCGCGCC    360

GAGGCGCTGC GCCCCGCGGT GCGGGAGCTG CTGGACGAGA TCCTGGGCGG GCTGGTGAAG    420

GGGGAGCGGC CGGTCGACCT GGTCGCCGGA CTGACGATCC CGGTGCCCTC GCGGGTCATC    480

ACCCTGCTCT TCGGCGCCGG TGACGACCGC CGGGAGTTCA TCGAGGACCG CAGCGCGGTC    540

CTCATCGACC GCGGCTACAC CCCGGAGCAG GTCGCCAAGG CCCGGGACGA ACTCGACGGC    600

TATCTGCGGG AGCTGGTCGA GGAGCGGATC GAGAACCCGG GCACCGACCT GATCAGCCGG    660

CTCGTCATCG ACCAGGTGCG GCCGGGGCAT CTGCGGGTCG AGGAGATGGT CCCGATGTGC    720

CGGCTGCTGC TGGTGGCCGG TCACGGCACC ACCACCAGCC AGGCGAGCCT GAGCCTGCTC    780

AGCCTGCTCA CCGACCCGGA GCTGGCCGGG CGCCTCACCG AGGACCCGGC CCTGCTGCCC    840

AAGGCGGTCG AGGAGCTGCT GCGCTTCCAC TCCATCGTGC AGAACGGGCT GGCCCGTGCC    900

GCGGTGGAGG ACGTCCAGCT CGACGATGTG CTCATCCGGG CGGGCGAGGG CGTGGTGCTG    960

TCGCTGTCGG CGGGCAACCG GGACGAGACG GTCTTCCCCG ACCCGGACCG GGTGGACGTG   1020

GACCGCGACG CCCGCCGCCA TCTCGCCTTC GGCCACGGCA TGCACCAGTG CCTGGGCCAG   1080

TGGCTGGCCC GGGTGGAGCT GGAGGAGATC CTCGCCGCGG TGCTGCGCTG GATGCCCGGT   1140

GCCCGGCTCG CGGTGCCCTT CGAGGAGCTG GACTTCCGTC ATGAGGTGTC CAGTTACGGC   1200

CTCGGCGCCC TCCCGGTGAC CTGGTGA                                     1227

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

-continued (ii) MOLECULE TYPE: other nucleic acid
        (A) DESCRIPTION:   /desc = "hypothetical sequence"

(xi) SEQUENCE DESCRIPTION: SEQ ID NO: 24:

TAYGCNCARA THCCNACNTT YATG                                              24

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "DNA probe"

(xi) SEQUENCE DESCRIPTION: SEQ ID NO: 25:

TACGCSCAGA TCCCSACSTT CATG                                              24

US 6,514,735 B1

DNA SEQUENCE ENCODING ENZYMES OF CLAVULANIC ACID BIOSYNTHESIS

This is a continuation of application Ser. No. 09/385,028, filed Aug. 30, 1999, now U.S. Pat. No. 6,232,106 which is a divisional application of application Ser. No. 08/790,462, filed Jan. 29, 1997, now abandoned, which is a continuation-in-part of application Ser. No. 08/567,801, filed Dec. 6, 1995, now abandoned, which is a continuation of application Ser. No. 08/134,018, filed Oct. 8, 1993, now abandoned.

This invention relates to methods for the production of the antibiotic, clavulanic acid.

BACKGROUND OF THE INVENTION

Clavulanic acid is a broad spectrum beta-lactamase inhibitor and is an important antibiotic for the treatment of infectious diseases. It is produced commercially by the gram-positive mycelial prokaryote *Streptomyces clavuligerus*, which also produces the β-lactam antibiotics penicillin N, desacetoxy cephalosphorin C and cephamycin C. Until recently, however, the pathway employed for clavulanic acid biosynthesis was much less well understood than the pathways leading to these other antibiotics.

Without knowledge of the pathway for clavulanic acid biosynthesis, it was not possible to isolate the genes coding for the key enzymes and to manipulate these genes to increase antibiotic yield or permit production of the antibiotic in heterologous systems.

One of the earliest enzymes of the pathway to be purified and characterised was clavaminic acid synthase. Two isozymes have now been identified and characterised (Marsh et al., (1992), Biochem., vol. 31, pp. 12648–657).

European Patent Application 0349121 describes a 6.8 kb Bgl II restriction fragment isolated from *S. clavuligerus* that encodes a portion of the genetic information involved in clavulanic acid synthesis. No further characterization of this fragment was performed nor was the utility of this fragment determined.

Marsh et al (1992, Biochem. vol 31, pp. 12648–657) cloned and sequenced two isozymes of clavaminate synthase cs1 and cs2 separated by 28 kb, however their location relative to the cephamycin and penicillin biosynthetic clusters was not determined. Ward and Hodgson (1993, FEMS Microbiol. Lett. vol 110, pp. 239–242) reported on the occurrence of a biosynthetic gene cluster for clavulanic acid. Aidoo et al (1994, Gene vol 147, pp. 41–46) cloned and sequenced cla the gene encoding a protein (possibly proclavaminic acid amidinohydrolase) involved in clavulanic acid production. They reported that this gene was upstream from and adjacent to an ORF with the identical sequence of cs2. Paradkar and Jensen (1995, J Bacteriol, vol 177, pp. 1307–1314) further analyzed a 6.6 kb Bgl II fragment from *S. clavuligerus* comprising cs2 and through gene disruption experiments demonstrated its role in clavulanic acid synthesis.

Until the work of the present inventors, the complete complement of genes required for clavulanic acid synthesis had not been identified.

The present inventors have now isolated, cloned and sequenced a 15 kb DNA fragment from *S. clavuligerus* which encodes 10 ORFs. Within this 15 kb of DNA lies an 11.6 kb Eco RI fragment which codes for eight proteins and enables the production of clavulanic acid by transformants of non-clavulanic-producing organisms. This 11.6 kb fragment includes 8 complete ORFs (ORFs 2 to 9), two of which have been previously characterized (Marsh et al 1992, Paradkar and Jensen 1995). ORF1, which is incomplete, is not involved in clavulanic acid synthesis, ORF4 encodes the CLA protein and ORF5 is cs2, encoding one of the isozymes of clavaminate synthase. The function of the other remaining ORFs within this 11.6 kb fragment or their role in clavulanic acid synthesis is unknown.

SUMMARY OF THE INVENTION

An isolated genomic DNA molecule of 15 kb is provided comprising the nucleotide sequence set out in FIG. 2. This DNA molecule comprises 10 ORFs, eight of which are involved in clavulanic acid synthesis. A process is provided for producing clavulanic acid in a transformant of a non-clavulanate-producing host.

The present invention provides isolated DNA molecules having the nucleotide sequence of SEQ ID NOS: 15, 16, 19, 20, 21, 22 and 23.

Furthermore, the present invention is directed to DNA molecules comprising the nucleotide sequences that encode the amino acid sequence found in FIGS. 11, 12, 15, 16, 17, 18 and 19 which corresponds to SEQ ID NOS: 4, 5, 8, 9, 10, 11 and 12.

This invention also embraces DNA molecules comprising the nucleotide sequences encoding the amino acid sequences of FIGS. 11, 12, 15, 16, 17 and 18. These amino acid sequences correspond to the expression products of ORFs 2, 3, 6, 7, 8 and 9.

This invention is directed to isolated proteins having the amino acid sequence of FIGS. 11, 12, 15, 16, 17, 18 and 19. These amino acid sequences correspond to the expression products of the ORFs 2, 3, 6, 9 and 10 as defined in SEQ ID NOS: 4, 5, 8, 9, 10 and 11.

This invention is also directed to recombinant vectors that comprise DNA molecules as defined above where hosts that have been transformed with these recombinant vectors.

This invention is also directed to the process for producing clavulanic acid in a non-clavulantic acid producing host that comprises transforming the host with a DNA molecule as defined above and culturing the host under suitable conditions to produce clavulanic acid.

Furthermore, this invention is directed to processes for enhancing clavulanic acid production in a clavulanic acid producing host comprising transforming the host with a DNA molecule as defined above.

DESCRIPTION OF DRAWINGS

The invention, as exemplified by a preferred embodiment, is described with reference to the accompanying drawings in which:

FIG. 1 shows the N terminal amino acid sequence of CLA (amino acid residues 1–25 of SEQ ID NO: 6), the potential codons corresponding with this sequence (SEQ ID NO: 24), and the nucleotide sequence of a probe (Sequence ID NO: 25) directed to the underlined region of the sequence. The nucleotide sequence of the actual DNA sequence is defined in SEQ ID NO: 1, specifically nucleotides 5687–5710 of SEQ ID NO: 1, 3665–3678 of SEQ ID NO: 13, or 34–57 of SEQ ID NO: 17.

FIGS. 2A–2J shows the nucleotide sequence (Sequence ID No.:1) of a 15 kb genomic DNA fragment from *S. clavuligerus*. The sequences of the ten ORFs within the fragment are shown in upper case letters and the intergenic regions are shown in lower case letters. The locations of the beginning and end of each ORF are also indicated directly above the nucleotide sequence. Asterisks above the sequence indicate the EcoRI sites which mark the beginning and end of the portion of the DNA sequence which contains all the genetic information for clavulanic acid synthesis.

FIG. 9 shows the deduced amino acid sequence (Sequence ID No.:3) of ORF1 of FIG. 2.

FIG. 10 shows the deduced amino acid sequence (Sequence ID No.:4) of ORF2 of FIG. 2.

FIG. 11 shows the deduced amino acid sequence (Sequence ID No.:5) of ORF3 of FIG. 2.

FIG. 12 shows the deduced amino acid sequence (Sequence ID No.:6) of ORF4 of FIG. 2.

FIG. 13 shows the deduced amino acid sequence (Sequence ID No. :7) of ORF5 of FIG. 2.

FIG. 14 shows the deduced amino acid sequence (Sequence ID No .: 8) of ORF6 of FIG. 2.

FIG. 15 shows the deduced amino acid sequence (Sequence ID No. :9) of ORF7 of FIG. 2.

FIG. 16 shows the deduced amino acid sequence (Sequence ID No.:10) of ORF8 of FIG. 2.

FIG. 17 shows the deduced amino acid sequence (Sequence ID No.:11) of ORF9 of FIG. 2.

FIG. 18 shows the deduced amino acid sequence (Sequence ID No.:12) of ORF10 of Fiqure 2.

FIGS. 19–23. The upper panel shows the results of Southern hybridizations using the probes and gene fragments as set forth in the restriction maps of the lower panel.

FIG. 19 shows the construction of the orf-2 mutant.

FIG. 20 shows the construction of the orf-3 mutant.

FIG. 21 shows the construction of the orf-6 mutant.

FIG. 22 shows the construction of the orf-8 mutant.

FIG. 23 shows the construction of the orf-9 mutant.

DETAILED DESCRIPTION OF THE INVENTION

Figure 3:
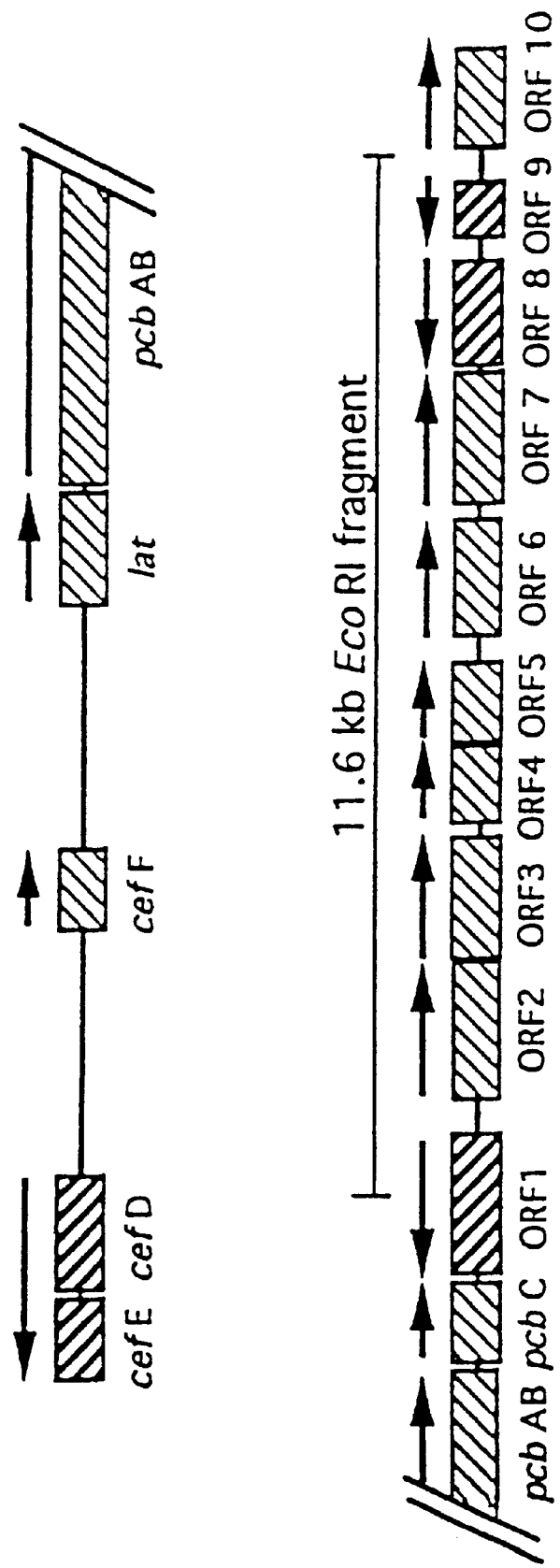
FIG. 3 shows the location of the open reading frames downstream from pcbC.
Figure 4:
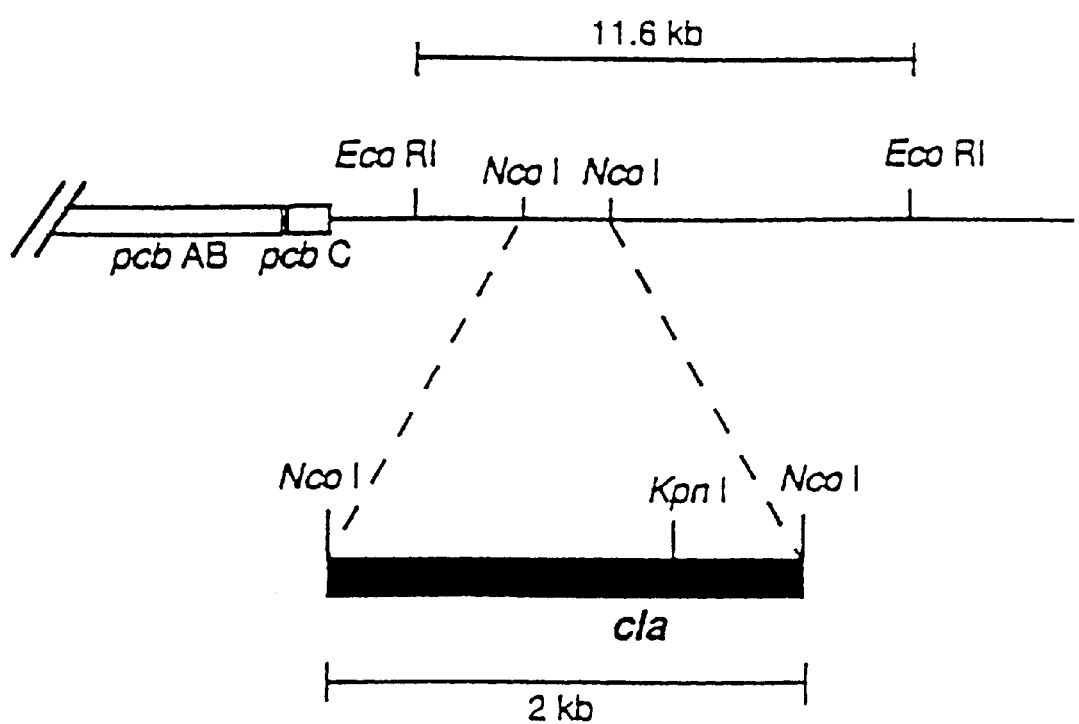
FIG. 4 shows a partial restriction map of the DNA sequence of FIG. 2 in the region surrounding cla (ORF4).
Figure 5:
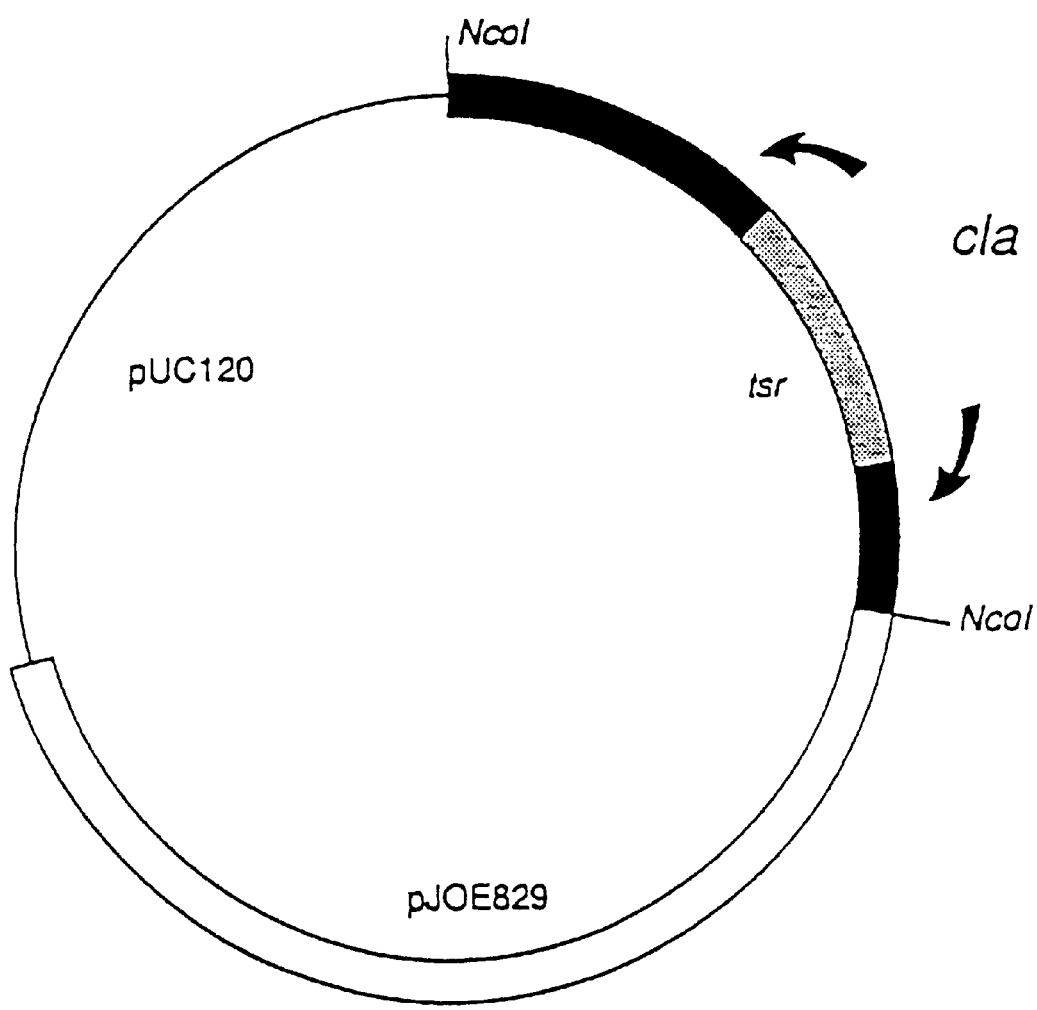
FIG. 5 shows a shuttle vector used for disruption of the cla gene.

Production of penicillin and cephamycin antibiotics in S. clavuligerus starts with the conversion of lysine to α-aminoadipic acid (Madduri et al., (1989), J. Bacteriol., v. 171, pp. 299–302; (1991), J. Bacteriol., v. 173, pp. 985–988). α-Aminoadipic acid then condenses with cysteine and valine to give δ-(L-α-aminoadipyl)-L cysteinyl-D-valine (ACV) by the action of aminoadipyl cysteinyl-valine synthetase (ACVS). ACV is converted by isopenicillin N synthase (IPNS) to isopenicillin N, and, through a series of reactions, to desacetoxycephalosporin C and ultimately to cephamycin C (Jensen et al., (1984), Appl. Microbiol. Biotechnol., v. 20, pp 155–160).

The ACVS of S. clavuligerus has been purified and partially characterized by three separate groups, and estimates of its molecular weight vary from 350,000 to 500,000 Da (Jensen et al., (1990) J. Bacteriol., v. 172, pp. 7269–7271; Schwecke et al., (1992), Eur. J. Biochem., v. 205, pp. 687–694; Zhang and Demain, (1990), Biotech Lett., v. 12, pp. 649–654). During their purification, Jensen et al. observed a 32,000 Da protein which co-purified with ACVS despite procedures which should remove small molecular weight components. It has now been found that this protein is not related to ACVS but rather to clavulanic acid biosynthesis. It has been designated CLA.

In accordance with one embodiment of the invention, the present inventors have identified, cloned and sequenced the gene (cla) encoding this protein.

In accordance with a further embodiment of the invention, the inventors have cloned and sequenced a 15 kb stretch of genomic DNA from S. clavuligerus which includes the cla gene. Within this 15 kb sequence, the inventors have identified an 11.6 kb DNA fragment which, when introduced into the non-clavulanate producer S. lividans as described in Example 4, enabled that species to produce clavulanic acid. This indicates that the 11.6 kb fragment contains all the genetic information required for clavulanate production.

As will be understood by those skilled in the art, the identification of the DNA sequence encoding the enzymes required for clavulanate synthesis will permit genetic manipulations to modify or enhance clavulanate production. For example, clavulanate production by S. clavuligerus may be modified by introduction of extra copies of the gene or genes for rate limiting enzymes or by alteration of the regulatory components controlling expression of the genes for the clavulanate pathway.

Heterologous organisms which do not normally produce clavulanate may also be enabled to produce clavulanate by introduction, for example, of the 11.6 kb DNA sequence of the invention by techniques which are well known in the art, as exemplified herein by the production of S. lividans strains capable of clavulanate synthesis. Such heterologous production of clavulanic acid provides a means of producing clavulanic acid free of other contaminating clavams which are produced by S. clavuligerus.

Suitable vectors and hosts will be known to those skilled in the art; suitable vectors include pIJ702, pJOE829 and pIJ922 and suitable hosts include S. lividans, S. parvulus, S. griseofulvus, S. antibioticus and S. lipmanii.

Additionally, the DNA sequences of the invention enable the production of one or more of the enzymes of the clavulanate pathway by expression of the relevant gene or genes in a heterologous expression system.

The DNA sequences coding for one or more of the pathway enzymes may be introduced into suitable vectors and hosts by conventional techniques known to those skilled in the art. Suitable vectors include pUC118/119 and pET-11 and suitable hosts include many organisms, including *E. coli* strains such as MV1193 and BL21(DE3).

An oligonucleotide probe (SEQ ID NO:25) based on the N-terminal amino acid sequence of CLA (amino acid residues 1–25 of SEQ ID NO: 6) was constructed as shown in FIG. 1 and was used to isolate the gene coding for the protein from *S. clavuligerus*, as described in Example 1.

The gene was found to be located in the S. clavuligerus chromosome about 5.7 kb downstream of pcbC, the gene which encodes isopenicillin N synthase. The gene contains a 933 bp open reading frame (ORF), encoding a protein of molecular weight 33,368. The deduced amino acid sequence was compared to database sequences and showed greatest similarity to enzymes associated with arginine metabolism, notably agmatine, ureohydrolase and arginases.

When an internal fragment of the cla gene was labelled and used to probe restriction endonuclease digests of genomic DNA from a variety of other Streptomyces and related species, evidence of homologous sequences was seen only in other clavulanic acid or clavam metabolite producers, including *Streptomyces jumonijinensis, Streptomyces lipmanii* and *Streptomyces antibioticus*. No cross reactivity was seen to the β-lactam producing species *Nocardia lactamdurans, Steptomyces griseus* or *Streptomyces cattleya*, nor to any of a variety of other Streptomyces species which do not produce β-lactam compounds, including *S. fradiae* ATCC 19609, *S. venezuelae* 13s and *S. griseofulvus* NRRL B-5429.

Disruption of the cla gene, as described in Example 3, led to loss of the ability to synthesise clavulanic acid.

A 15 kb DNA sequence extending downstream from pcbC was cloned and sequenced as described in Example 5. The nucleotide sequence is shown in FIG. 2. When this SEQ ID No.: 1 sequence information was analysed for percent G+C as a function of codon position (Bibb et al., (1984), Gene, v. 30, pp. 157–166), ten complete ORFs were evident, as shown in FIG. 3. ORF 4 corresponds to cla. ORF 1,7 & 8 are oriented in the opposite direction pcbC. ORFs 2–6 and ORF 10 are all oriented in the same direction as pcbC. ORFs 2 and 3, and ORFs 4 and 5 are separated by very short intergenic regions suggesting the possibility of transcriptional and translational coupling. Table 1 summarises the nucleotide sequences and lengths of ORFs 1–10.

TABLE 1

| ORF # | Start Location (bp) | End Location (bp) | Length (bp) | Size of ORF (aa residues) | SEQ ID NO. |
|---|---|---|---|---|---|
| 1* | 1764 | 109 | 1656 | 552 | 14 |
| 2 | 2216 | 3937 | 1722 | 574 | 15 |
| 3 | 3940 | 5481 | 1542 | 514 | 16 |
| 4 | 5654 | 6595 | 942 | 314 | 17 |
| 5 | 6611 | 7588 | 978 | 326 | 18 |
| 6 | 7895 | 9076 | 1182 | 394 | 19 |
| 7 | 9241 | 10908 | 1668 | 556 | 20 |
| 8* | 12296 | 10998 | 1299 | 433 | 21 |
| 9* | 13365 | 12622 | 744 | 248 | 22 |
| 10 | 13769 | 14995 | 1227 | 409 | 23 |

*ORFs which are oriented in the opposition direction.

When the predicted amino acid sequences of proteins encoded by ORFs 1–10 were compared to protein sequence databases, some similarities were noted in addition to the already mentioned similarity between CLA and enzymes of arginine metabolism. ORF 1 (SEQ ID No.: 14) showed a low level of similarity to penicillin binding proteins from several different microorganisms which are notable for their resistance to β-lactam compounds.

An EcoRI fragment of the 15 kb DNA sequence, containing 11.6 kb DNA, was cloned into a high copy number shuttle vector and introduced into *S. lividans*, as described in Example 4. Of seventeen transformants examined, two were able to produce clavulanic acid, indicating that the 11.6 kb fragment contains all the necessary genetic information for clavulanic acid production.

This 11.6 kb fragment encompasses ORF 2 to ORF 9 of the 15 kb DNA sequence.

ORF 2 (SEQ ID No.: 15) shows a high degree of similarity to acetohydroxyacid synthase (AHAS) enzymes from various sources. AHAS catalyses an essential step in the biosynthesis of branched chain amino acids. Since valine is a precursor of penicillin and cephamycin antibiotics, and valine production is often subject to feedback regulation, it is possible that a deregulated form of AHAS is produced to provide valine during the antibiotic production phase. Alternatively, an AHAS-like activity may be involved in clavulanic acid production. While the presently recognized intermediates in the clavulanic acid biosynthetic pathway do not indicate a role for AHAS, the final step in the biosynthetic pathway, conversion of clavaminic acid to clavulanic acid, requires NADPH, and either pyruvate or α-ketobutyrate as well as other cofactors (Elson et al., (1987), J. Chem. Soc. Chem. Commun., pp. 1739–1740). It is striking that these same substrates and cofactors are required for AHAS activity. Perhaps the conversion of clavaminate to clavulanate actually involves several steps, one of which is catalyzed by an AHAS-like activity. ORFs 3 (SEQ ID No.: 16) does not show a significant similarity to any proteins in the data bases. ORF 6 (SEQ ID No.: 19) shows similarity to ornithine acetyltransferase. Ornithine has been suggested to be the immediate precursor of a 5-C fragment of the clavulanic acid skeleton, but the details of the reaction required for the incorporation of ornithine are unknown. ORF 7 (SEQ ID No.: 20) shows weak similarity to protein XP55 from *S. lividans*, and a lower level of similarity to oligopeptide binding proteins from various other species. Similarly, ORF 8 (SEQ ID No. 21) shows weak similarity to several transcription activator proteins, and ORF 9 (SEQ ID No.: 22) shows weak similarity to ribitol 5 $PO_4$ dehydrogenase-type enzymes. ORF 10 (SEQ ID NO: 23) shows a high similarity to cytochrome P450 type enzymes from other Strepomyces species.

ORF5 has now been identified as the gene for clavaminate synthase II (Marsh (1993) supra).

Figure 6:
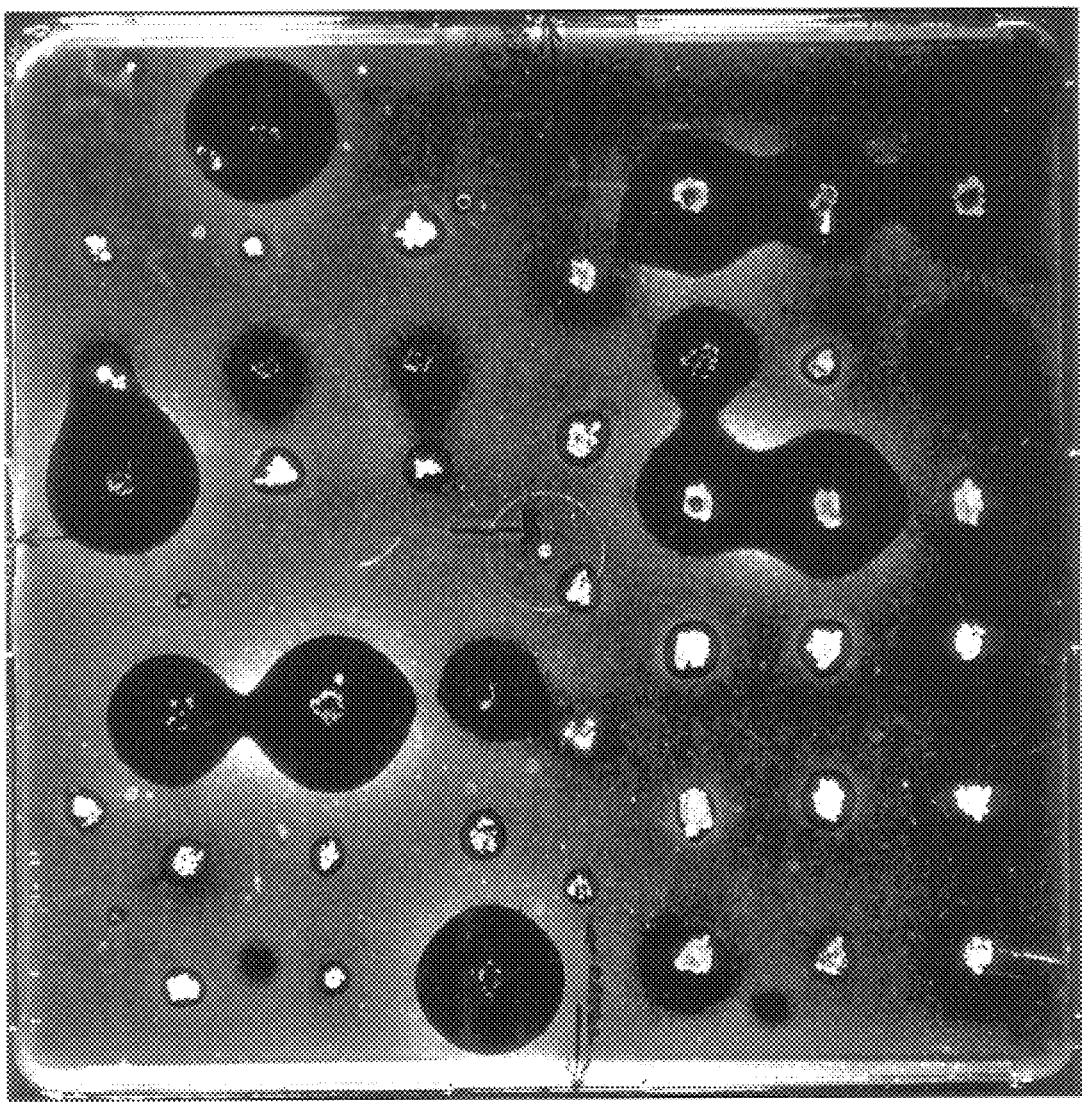
FIG. 6 shows a photograph of an agar plate bearing cultures of S. lividans transformants.

When a plasmid isolated from one of the two clavulanic acid-producing transformants was retransformed into *S. lividans*, about 40–45% of the resulting colonies were able to produce clavulanic acid, as shown in FIG. 6.

EXAMPLES

Example 1

Bacterial Strains, Vectors and Growth Conditions

*Streptomyces clavuligerus* NRRL 3585, *Stretomyces jumonjinenisis* NRRL 5741, *Streptomyces lipmanii* NRRL 3584, *Streptomyces griseus* NRRL 3851, *Nocardia lactamdurans* NRRL 3802 and *Steptomyces cattleya* NRRL 3841 were provided by the Northern Regional Research Laboratories, Peoria, Ill. *Streptomyces antibioticus* ATCC 8663 and *Streptomyces fradiae* ATCC 19609 were obtained from the American Type Culture Collection, Manassas, Va. *Streptomyces lividans* strains 1326 and TK24 were provided by D. A. Hopwood (John Innes Institute, Norwich, U.K.), *Streptomyces venezuelae* 13s and *Streptomyces griseofuscus* NRRL B-5429 were obtained from L. C. Vining (Department of Biology, Dalhousie University, Halifax, N. S.). Cultures were maintained on either MYM (Stuttard (1982) J. Gen. Microbiol., v. 128, pp. 115–121) or on a modified RS medium (Hopwood et al. (1985) in "Genetic Manipulation of Streptomyces: a laboratory manual", John Innes Foundation, U.K.) containing maltose instead of glucose and lacking sucrose (R5-S). *Escherichia coli* MV1193 (Zoller and Smith (1987) Methods in Enzymology, v. 154, pp. 329–349), used as recipient for all of the cloning and subcloning experiments, was grown in Luria Broth (LB; Sambrook et al. (1989) in "Molecular Cloning: a laboratory manual", Cold Spring Harbour, N.Y.) or on LB agar (1.5%) plates containing ampicillin (50 µg/mL) or tetracycline (10 µg/mL). The cloning vectors pUC118 and pUC119. (Vieira and Messing (1987) Methods in Enzymology, v. 153, pp. 3–11) were provided by J. Vieira (Waksman Institute of Microbiology, Rutgers University, Piscataway, N.J.). The plasmid vector pJOE829 was generously provided by J. Altenbuchner (University of Stuttgart, Stuttgart, Germany). The plasmid pIJ702 was obtained from the American Type Culture Collection, Manassas, Va. Restriction enzymes were purchased from Boehringer Mannheim, and used according to the manufacturers' specifications.

Separation of CLA from ACVS

CLA was previously characterized as a 32,000 Da molecular weight protein present in preparations of highly purified ACVS (Jensen et al. (1990), supra). The small size of CLA suggested that its co-purification with ACVS resulted from a physical association between the two proteins.

ACVS and CLA were resolved by applying a 0.2 ml sample of purified ACVS containing CLA onto a Superose 6 HR 10/30 (Pharmacia), which was equilibrated and eluted in 0.1 M MOPS buffer, pH 7.5 containing 0.05 M KCl, 1 mM dithiothreitol, and 20% glycerol, at a flow rate of 0.25 ml/min.

Comparison of the CLA retention time with those of molecular weight standards indicated that the native molecular weight of CLA was in excess of 270 kDa. The difference in molecular weight between native and denatured forms of CLA suggests that the native protein exists as an oligomer of eight identical subunits.

Isolation of Gene (cla) for CLA

N-terminal amino acid sequence information for CLA was obtained by electrophoretically transferring the protein from SDS polyacrylamide gels onto Immobilon membranes (Millipore Ltd.,) and submitting the material to the Protein Microsequencing Laboratory (University of Victoria,) for analysis. Information obtained for 25 amino acids at the N-terminus (amino acid residues 1–25 of SEQ ID NO: 6) was used to prepare a 24 mer oligonucleotide probe (SEQ ID NO: 25) with 8-fold degeneracy to the amino acid sequence underlined in FIG. 1. The amino acids in brackets indicate ambiguities in the N terminal sequence. The actual DNA sequence from the cloned fragment is indicated in FIG. 2 and SEQ ID No: 1.

The probe was designed as an 8-fold degenerate mixture of oligonucleotides to take into consideration the biased codon usage of streptomyces Wright and Bibb (1992), Gene, v. 113, pp. 55–65).). End-labelled probe was then used to screen a cosmid library of *S. clavuligerus* genomic DNA fragments.

A library of *S. clavuligerus* genomic DNA fragments (15–22 kb size fractionated fragments) was constructed as previously described (Doran et al. (1990), J. Bacteriol, v. 172, pp. 4909–4918). Using the cosmid vector pLAFR3. A collection of 1084 isolated *E. coli* colonies contained recombinant cosmids was screened for the presence of cla using the 24-mer mixed oligonucleotide probe (FIG. 1) which had been end-labelled with [γ-$^{32}$P]dATP and polynucleotide kinase (Boehringer Mannheim). Colony hybridization and subsequent washing was performed as described by Sambrook et al., (1989), at 55° C. with a final wash in 0.2×SSC (I×SSC, 0.15M NaCl and 0.015M sodium citrate) and 0.1% SDS.

Five colonies which gave strong hybridization signals were isolated from the panel of 1084 clones, and restriction analysis showed that the positive clones contained overlapping fragments of DNA. Two clones, K6L2 and K8L2, with sequences that spanned about 40 kb of the *S. clavuligerus* genome, were chosen for further analysis. Clone K8L2 contained about 22 kb of *S. clavuligerus* genomic DNA and included a portion of cla and all of the pcbC gene which encodes IPNS in the penicillin/cephamycin biosynthetic pathway. A restriction map of K6L2 is shown in FIG. 9. Within the approximately 27 kb of DNA contained in K6L2, the oligonucleotide probe hybridized to a 2.0 kb NcoI fragment which was subsequently found to contain the entire cla gene. Hybridization studies, restriction mapping and DNA sequence analysis revealed that cla was situated 5.67 kb downstream of the pcbC gene of *S. clavuligerus* (FIG. 9).

DNA Sequencing and Analysis

Ordered sets of deletions were generated (Henikoff, 1984) extending across the cla region of the 2.0 kb NcoI fragment (FIG. 9C). The deletion generated fragments were sequenced in both orientations by the dideoxynucleotide chain termination method of (Sanger et al. (1977), P.N.A.S., v. 74, pp. 5463–5467) using Sequenase (version 2.0) DNA polymerase (United States Biochemical Corporation). Areas of compression in the sequence band pattern were relieved by carrying out reactions using 7-deaza-dGTP in place of dGTP. The nested deletion fragments resided either in pUC118 or pUC119, and were sequenced using the commercially available universal primers.

The nucleotide sequence data were analyzed for the presence of restriction sites, open reading frames (ORFs) and codon usage by the PC-Gene programme (Intelligenetics Corp.). Similarly searches were accomplished with the FASTA program searching the GenPept database (release number 71) available through GenBank (Pearson and Lipman (1988), P.N.A.S., v. 85, pp. 2444–2448).

Figure 7:
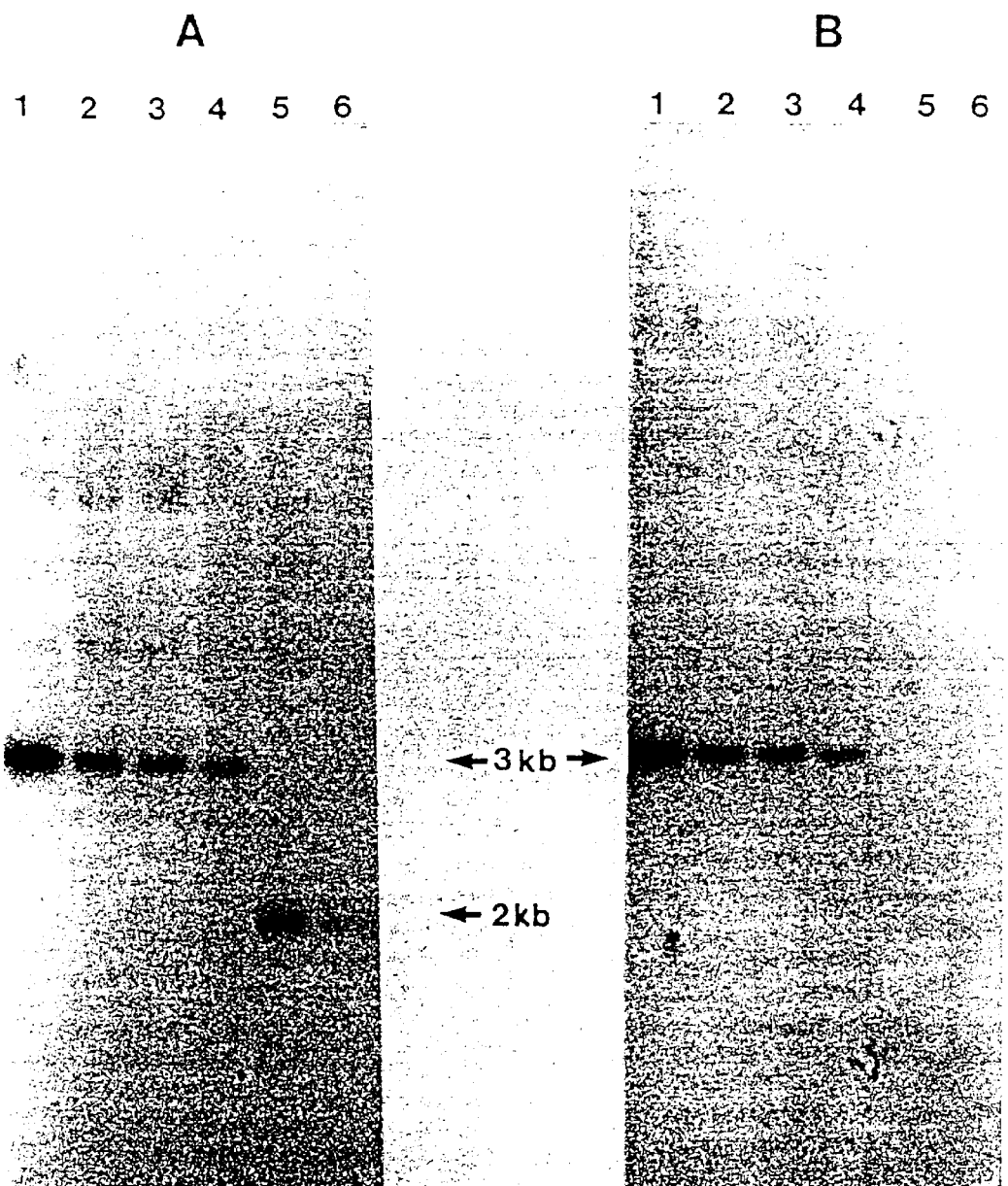
FIG. 7 shows a Southern blot of NcoI digests of genomic DNA from five presumptive mutants (lanes 1–5) and from wild-type S. clavuligerus (lane 6). Panel A: membranes probed with cla-specific probe. Panel B: membranes probed with tsr-specific probe.
Figure 8:
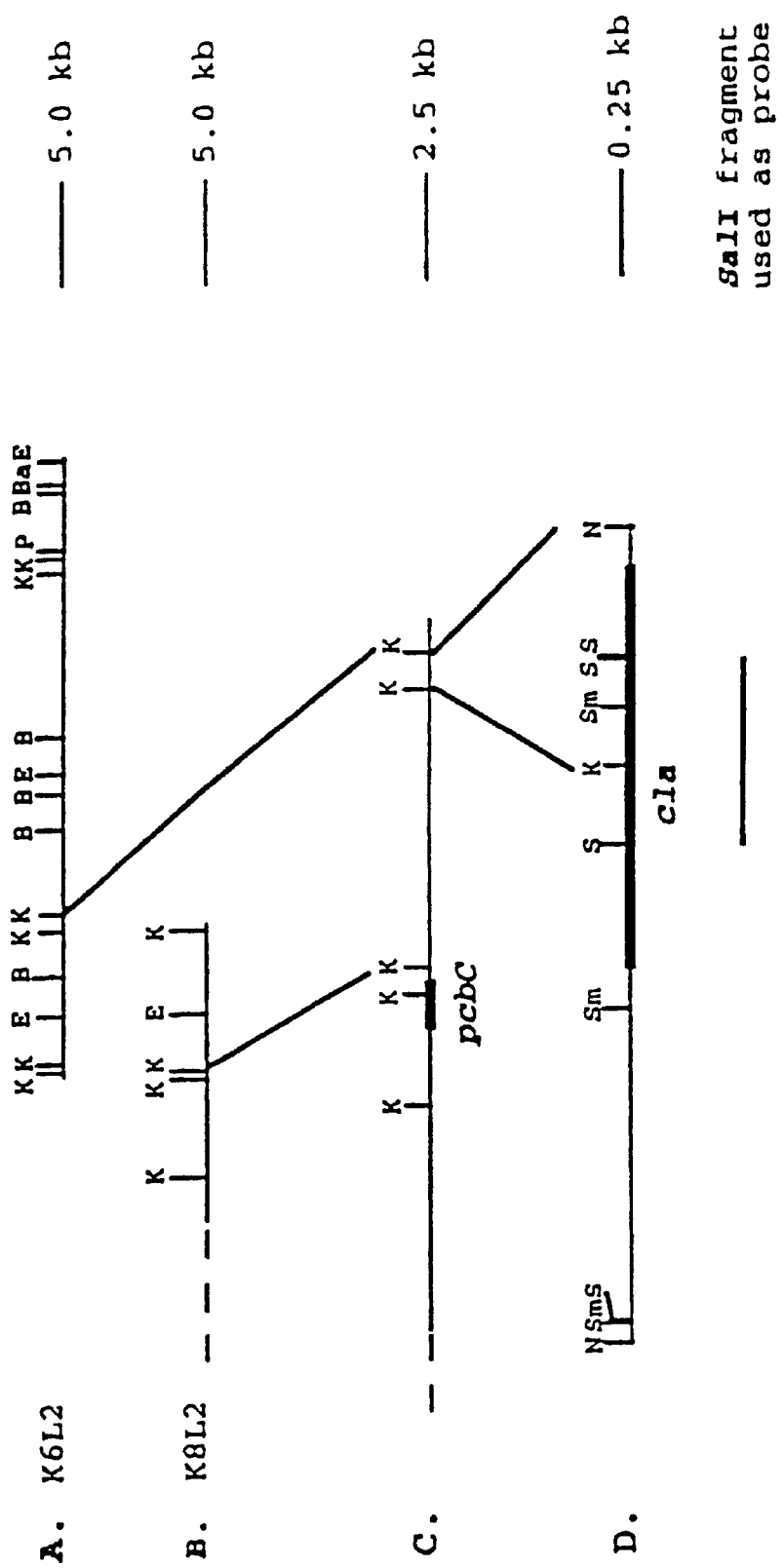
FIG. 8 shows restriction enzyme maps of S. clavuligerus DNA inserts in cosmids. A. Restriction enzyme map of cosmid K6L2. B. Partial restriction enzyme map of cosmid K8L2. C. Restriction map of cosmids K6L2 and K8L2 indicating location of pcbC gene in relation to cla. D. The 2.0 kb NcoI fragment encompassing the cla gene used in generating nested deletions for sequencing. Abbreviations: Ba, BamHI; B,BglII; E,EcoRI; K,KpnI; N, NcoI; S,SalI; and Sm,SmaI.

An ORF at 939 bp with a potential ribosome site 9 bp from the GTG start codon was found which encoded a putative protein with a molecular weight of 33,368 Da. This value is in close agreement to the molecular weight estimated for CLA by SDS-PAGE (Jensen et al., 1990). The analysis of percent G+C as a function of codon position (FRAME analysis), using the algorithm of Bibb et al., (1984), indicated the presence of a typical streptomycete ORF (data not shown) with a G+C content of 70%. Computer aided data base searches for sequences similar to cla revealed a high degree of similarity to agmatine ureohydrolase (40.5% identity over 291 amino acids) and somewhat lower similarity to arginases (29.6% identity over 135 amino acids to arginases from yeast and rat) as shown in FIG. 7. The *S. clavuligerus* CLA sequence was aligned with the *E. coli* AUH sequence by the FASTA program described above. The AUH sequence had previously been aligned with the three ARG sequences (Szumanski & Boyle (1990), J. Bacteriol., v. 172, pp. 538–547). Identical matches in two or more sequences are indicated with upper case letters.

Example 2

DNA Hybridization

Genomic DNA preparations from various Streptomyces species were isolated as described by Hopwood et al. (1985). For interspecies DNA hybridization analysis, 2.0 μg amounts of genomic DNA preparations were digested with NcoI for 16 h, and electrophoresed in 1.0% agarose gels. The separated DNA fragments were then transferred onto nylon membranes (Hybond-N, Amersham) and hybridized with a cla specific probe prepared by labelling an internal 459 bp SalI fragment (FIG. 1) with $[\alpha^{32}P]DAPT$ by nick translation. Hybridization was done as decribed by Sambrook et al., (1989). Hybridization membranes were washed twice for 30 min in 2×SSC; 0.1% SDS and once for 30 min in 0.1×SSC; 0.1% SDS at 65° C.

Sequences Homologous to cla in Other Streptomycetes

Three of six producers of β-lactam antibiotics, *S. clavuligerus*, *s. lipmanii* and *S. jumonjinesis* showed positive hybridization signals whereas *S. cattleya*, *S. griseus*, and *N. lactamdurans* did not (data not shown). None of the nonproducing strains examined, *S. venezuelae*, *S. lividans*, *S. fradiae*, *S. antibioticus* and *S. griseofuscus* gave any signal. All of the streptomycetes that gave positive signals were producers of clam-type metabolites (Elson et al., 1987).

Example 3

Disruption of the Genomic cla Gene

A 2.0 kb NcoI fragment that contained the entire cla gene was digested at its unique KpnI site and the ends made blunt by treatment with the Klenow fragment of *E. coli* DNA polymerase I. A thiostrepton resistance gene (tsr), isolated as a 1085 bp BclI fragment from pIJ702 and cloned into the BamHI site of pUC118 was excised as a SmaI/XbaI fragment and the ends made blunt as above and ligated into the KpnI site of cla. The ligation mixture was introduced into *E.coli* MV1193 and the transformants screened for the presence of the tsr gene by colony hybridization (Sambrook et al., 1989).

Replacement of the chromosomal cla gene by a copy disrupted by the insertion of tsr, at an internal KpnI site, was achieved by double recombination. Successful gene replacement was apparent when the 2.0 kb NcoI fragment which carries cla in the wild type organism was replaced by a 3.0 kb NcoI fragment due to the insertion of the 1.0 kb tsr gene in the mutants. Four of the five mutants tested showed the expected increase in the size of the NcoI fragments, and the larger NcoI fragments also hybridized with a tsr specific probe. The five mutant was apparently a spontaneous theostrepton resistant mutant.

Antibiotic Assay

The agar diffusion assay was used for determining both penicillin/cephamycin and clavulanic acid production. *S. clavuligerus* strains to be assayed were grown in 10 ml. amounts of Trypticase Soy Broth (TSB; Baltimore Biological Laboratories) medium with 1.0% starch for 48 h. The cultures were washed twice with 10.3% sucrose and once with MM (Jensen et al. (1982), J. Antibiot., v. 35, pp. 483–490) and the mycelium resuspended in 10.0 mL of MM. Two milliliters of washed cell suspension was inoculated into 100 mL of MM and incubated at 28° C. for 48 h. The cultures were harvested by centrifugation, and the supernatants were assayed for both penicillin/cephamycin and clavulanic acid using bioassay procedures described previously (Jensen et al. (1982), supra).

All of the resulting colonies with disrupted cla genes grew equally well on minimal medium and complex media and produced as much penicillin and cephamycin as did the wild-type, but produced no clavulanic acid (data not shown). HPLC analysis of cell supernatants confirmed the inability of the disrupted cla mutants to synthesize any clavulanic acid (data not shown).

Example 4

Protoplast Formation and Transformation

*E. coli* competent cell preparation and transformation were as described by Sambrook et al., (1989). Protoplasts of *S. clavuligerus* were, prepared, transformed and regenerated as described by Bailey et al. (1984), Bio/Technology, v. 2, pp. 808–811, with the following modifications. Dextrin and arginine in the regeneration medium were replaced by starch and sodium glutamate respectively. Protoplasts were heat shocked at 43° C. for 5 min prior to the addition of DNA. Standard procedures were used for protoplasting and transformation of *S. lividans* (Hopwood et al. (1985)).

The 11.6 kb EcoR1 fragment from K6L2 (FIG. 9) was cloned into the EcoR1 site of pCAT-119. pCAT-119 is derivative of pUC119 which was prepared by insertionally inactivating the ampicillin resistance gene of pUC119 by the insertion of a chloramphenicol acetyltransferase gene (Jensen et al. (1989), Genetics & Molec. Biol. of Ind. Microorg., pp. 239–245 Ed. Hershberger, Amer. Soc. Microbiol). The PCAT-119 plasmid carrying the 11.6 kb fragment was then digested with PstI and ligated to the Streptomyces phasmid pIJ702, which had also been digested with PstI. The resulting bifunctional plasmid carrying the 11.6 kb insert was capable of replicating in either *E. coli* (with selection for chloramphenicol resistance) or in *S. lividans* (with selection for thiostrepton resistance). The ligation mixture was transformed to *E. coli*. Plasmid DNA was isolated from several of the chloramphenicol resistant transformants and analyzed by agarose gel electrophoresis to ensure that the proper plasmid construct was obtained. This isolated plasmid material from *E. coli* was then transformed into *S. lividans* as described by Hopwood and transformants were selected by plating onto R2YE medium containing thiostrepton at a concentration of 50 μg/ml.

Thiostrepton resistant *S. lividans* transformants carrying the bifunctional plasmid with the 11.6 kb insert were patched onto MYM agar plates and allowed to incubate for 48 h at 28° C. before they were overlayered with molten soft nutrient agar containing penicillin G at a concentration of 1 μg/ml and inoculated with *Staphylococcus aureus* N-2 as indicator organism (Jensen, 1982). (*S. aureus* N-2 was obtained form the Department of Microbiology Culture Collection, University of Alberta. Any organism which produces a β-lactamase sensitive to clavulanic acid may be used as indicator organism.) Zones of inhibition which appeared around the *S. lividans* colonies upon incubation overnight at 30° C. were evidence of clavulanic acid production. Clavulanic acid-producing colonies were found amongst these initial *S. lividans* transformants at a frequency of about 12%. When plasmid DNA was isolated from one of these clavulanic acid-producing transformants and re-introduced into *S. lividans*, the frequency of clavulanic acid production in these 2nd round transformants was about 40–45%. FIG. 6 shows a photograph of an agar plate bearing 2nd. round transformants. Zones of inhibition are seen as clear areas in the agar; these appear on the photograph as dark circular areas.

Example 5
Sequencing of 15 kb DNA Fragment

Ordered sets of deletions were generated as described in Example 1 using fragments of the DNA insert from the cosmid clone K6L2 (FIG. 9) and subcloned into the E. coli plasmids pUC118 and pUC119. Overlapping fragments were chosen which extended from the end of the pcbC gene downstream for a distance of about 15 kb ending at the BglII site. The deletion generated fragments were sequenced in both orientations as described in Example 1. The sequence is shown in FIG. 2 and SEQ ID NO:1.

Example 6
Gene Disruption of the 12kb Fragment

Gene disruption experiments were conducted on the various open reading frames (ORF) to determine if a particular ORF was involved in clavulanic acid production or not. In order to determine the role of the various ORFs in clavulanic acid biosynthesis, mutants disrupted in one of the ORFs were constructed by a gene replacement procedure based on that described in Paradkar and Jensen (*Journal of Bacteriology*, March 1995, Vol. 177, no. 5, pages 1307 to 1314).

In all cases, the apramycin-resistance gene cassette (apr) was used to disrupt the genes encoded within the 12-kb DNA fragment. Before use, unless otherwise indicated, the apr-cassette was modified by adding NcoI restriction sites to both ends. This modification of the apr-cassette has been described in Paradkar and Jensen (*Journal of Bacteriology*, March 1995, Vol. 177, no. 5, pages 1307 to 1314). Since four NcoI sites are present within the 12 kb fragment and present within ORFs 3, 5, 6, and 8, respectively, insertion of the apr-cassette within the NcoI sites created a series of plasmids (called pCATL2) with disruptions in ORFs 3, 5, 6, or 8. The plasmids containing these fragments are referred to as pCATL2orf3, pCATL2orf5, pCATL2orf6, and pCATL2orf8, respectively. The construction of pCATL2orf5 has been previously disclosed (Paradkar and Jensen, *Journal of Bacteriology*, March 1995, Vol. 177, no. 5, pages 1307 to 1314). From each of these plasmids, a smaller fragment carrying only the disrupted gene and some flanking sequence (see details below) was subcloned and finally inserted into the Streptomyces vector pIJ486 (obtained from David A Hopwood, John Innes Institute) for transformation into *S. clavuligerus*. All routine manipulations involved in subcloning were done in *Escherichia coli* using standard cloning vectors, such as pUC119, pBluescript SK+etc. Since ORF2 and ORF9 do not contain NcoI sites, the disruptions of these ORFs were done in a slightly different manner. The preparation of ORF2, ORF3, ORF6, ORF8 and ORF9 are described in more detail below.

Construction of the Insertional Mutants

1. ORF2 Mutant

NotI-NcoI linker oligonucleotides were added to both ends of the apr gene cassette, and then this modified apr gene fragment was inserted into the NotI site within ORF2 carried on a 2.1-kb EcoRI-BglII fragment. Subsequently, the EcoRI-BglII fragment carrying the disrupted ORF2 was inserted into pIJ486.

Genomic DNA isolated from the wild type (wt) and from an ORF2 mutant was digested with EcoRI and NcoI, and then probed with a 2.1-kb EcoRI-BglII fragment (FIG. 20). The 2.7 kb hybridizing fragment present in the wild type has been replaced with a 1.8 kb fragment in the mutant. A 0.85 kb fragment is also expected to hybridize to the probe in the mutant, but owing to the conditions of electrophoresis under which the gel was that smaller fragment was not retained on the gel. The sizes of the remaining hybridizing fragments are consistent with the replacement of the wild type ORF2 with the apr-disrupted ORF2.

2. ORF3 Mutant

The apr cassette (with NcoI sites on each end) was inserted into the NcoI site within ORF3 carried on a 4 kb EcoRI-KpnI fragment. The fragment carrying the disrupted ORF3 was then subcloned into pIJ486.

Figure 21:
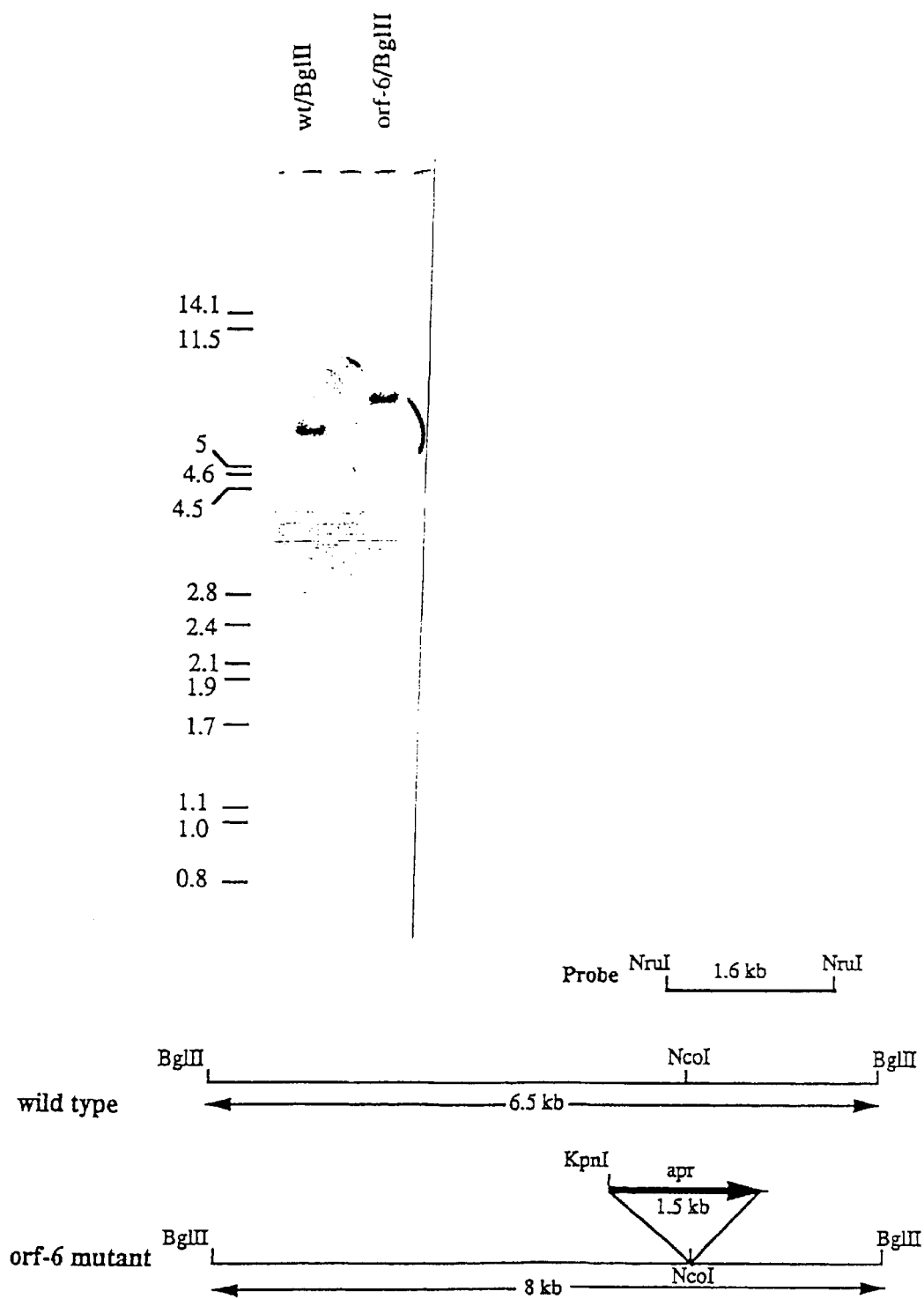

Genomic DNA from the wild type (wt) and from an ORF3 mutant was digested separately with BglII, and with KpnI, and probed with a 0.6-kb BglII-NcoI fragment (FIG. 21). In the BglII digests, the 6.5 kb hybridizing fragment present in the wild type has been replaced with 8 kb fragment in the mutant, while in the KpnI digests, the 5.8 kb fragment has been replaced with a 4.5 kb fragment. The sizes of these hybridizing fragments are consistent with the replacement of the wild type ORF3 with the apr-disrupted ORF3.

3. ORF6 Mutant

An 8-kb BglII fragment carrying the disrupted ORF6 was subcloned from pCATL2orf6 into pIJ486.

Figure 22:
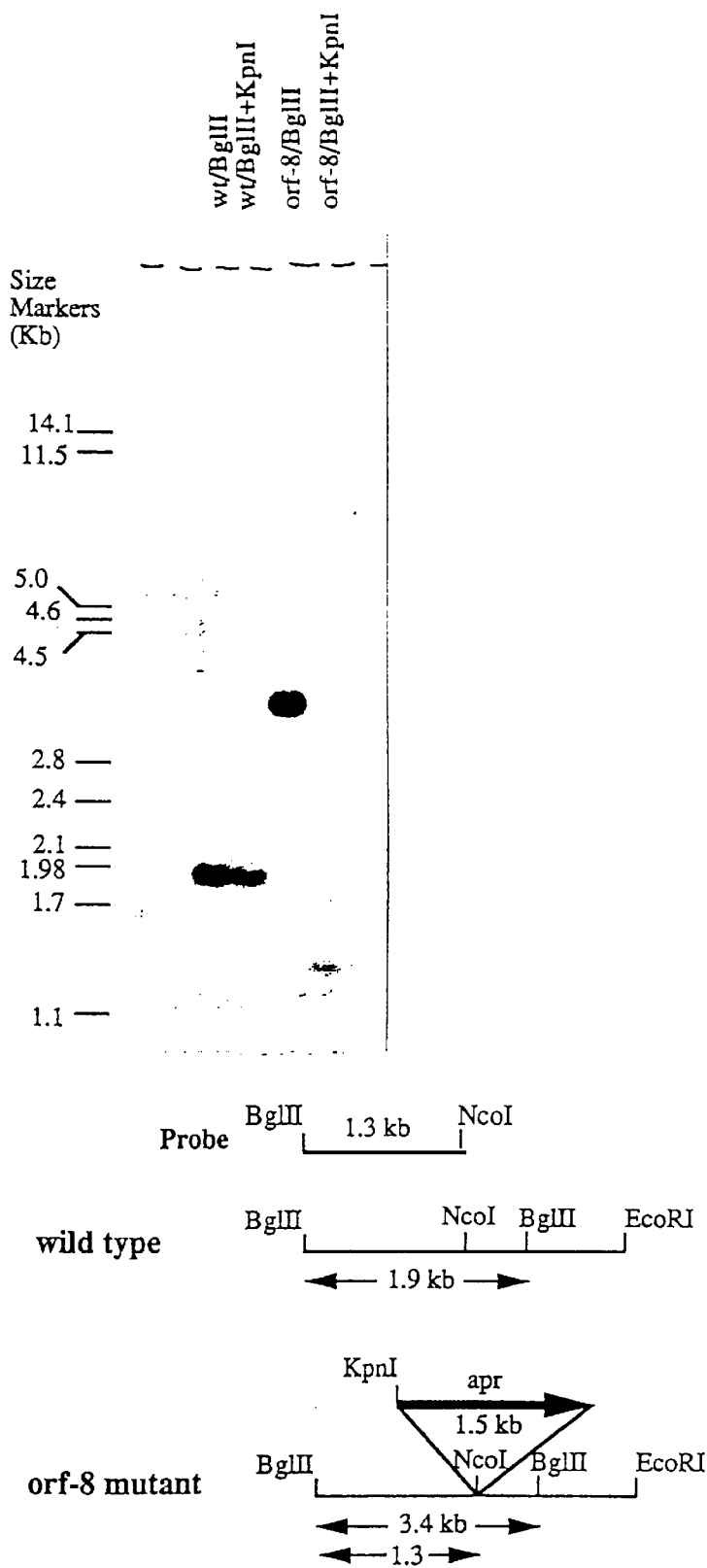

Genomic DNA from the wild type (wt) and from an ORF6 mutant was digested with BglII, and probed with a 1.6-kb NruI fragment (FIG. 22). The 6.5 kb hybridizing fragment present in the wild type has been replaced with an 8 kb fragment in the mutant. The sizes of these hybridizing fragments are consistent with the replacement of the wild type ORF6 with the apr-disrupted ORF6.

4. ORF8 Mutant

A 2.9 kb BglII-EcoRI fragment carrying the disrupted ORF8 was subcloned from pCATL2orf8 into pIJ486.

Figure 23:
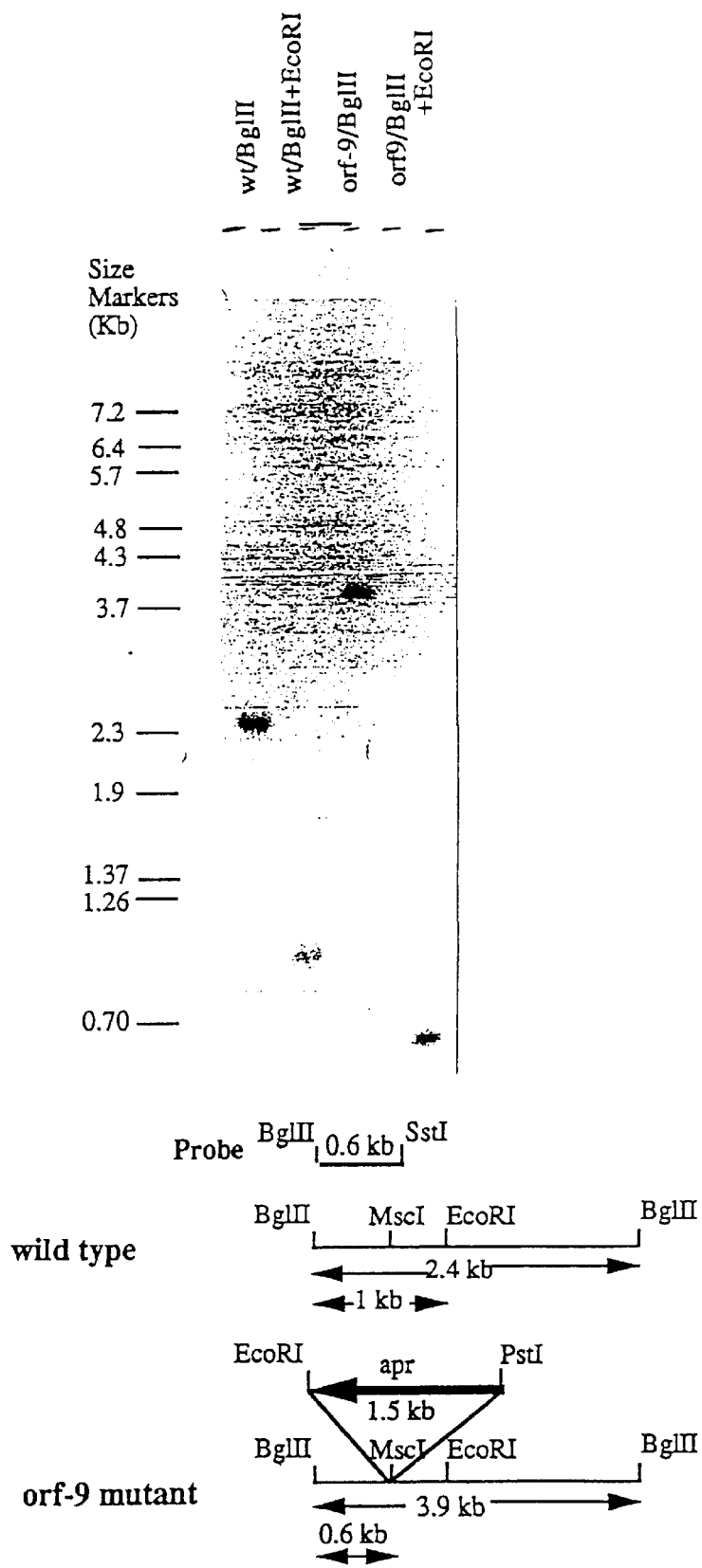

Genomic DNA from the wild type (wt) and from an ORF8 mutant was digested with BglII, and also with both BglII and KpnI, and probed with a 1.3 kb BglII-NcoI fragment (FIG. 23). In the BglII digests, the 1.9 kb hybridizing fragment present in the wild type has been replaced with a 3.4 kb fragment in the mutant, while in the BglII/KpnI digests, the 1.9-kb fragment has been replaced with a 1.3 kb fragment. The sizes of these hybridizing fragments are consistent with the replacement of the wild type ORF8 with the apr-disrupted ORF8.

5. ORF9 Mutant

The apr gene cassette was first cloned as an EcoRI-PstI fragment into the *E. coli* vector Pbluescript, and re-isolated as an EcoRV-SmaI fragment. This fragment was then inserted into the MscI site present in ORF9 contained within a 2.4 kb BglII fragment. Subsequently, the 4 kb fragment carrying the disrupted ORF9 was inserted into pIJ486.

Figure 24B:
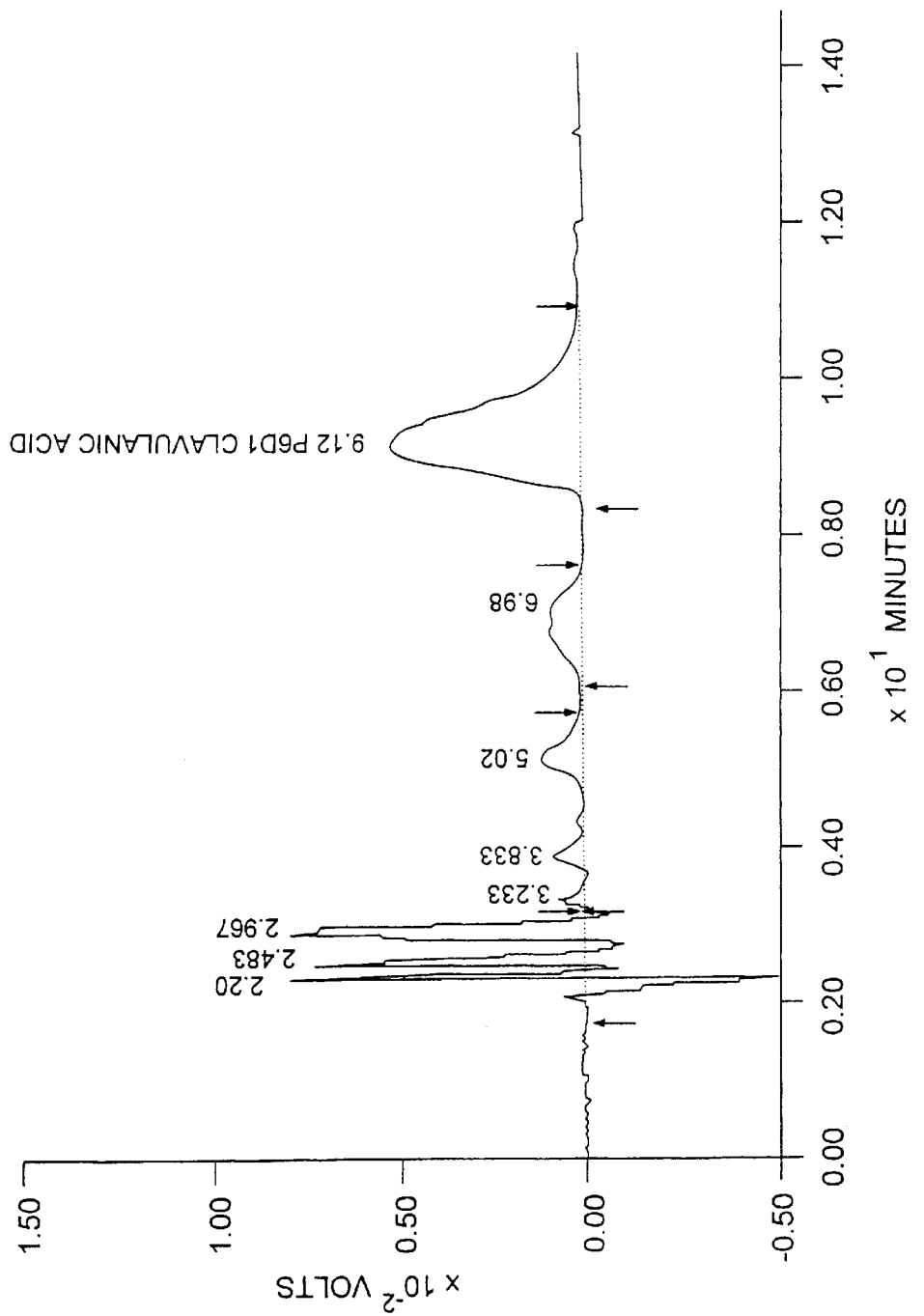
FIGS. 24(A), (B) and (C) high pressure liquid chromatography (HPLC) analysis of clavulanic acid in culture supernatants. Culture supernatants from 96 hour Starch-Asparagine medium-grown cultures of either wild type S. clavuligerus, or one of the gene disruption mutants were analyzed by HPLC. (A)Retention time of a clavulanic acids standard; (B) Wild type culture supernatant showing a peak due to clavulanic acid eluting with a retention time of 6.5 min. (C) Gene disruption mutant culture supernatant (ORF8 mutant). The same HPLC profile was seen for all of the other disruption mutants, including ORF2, ORF3, or ORF9, indicating that none of the mutants produced clavulanic acid under these culture conditions.
Figure 24C:
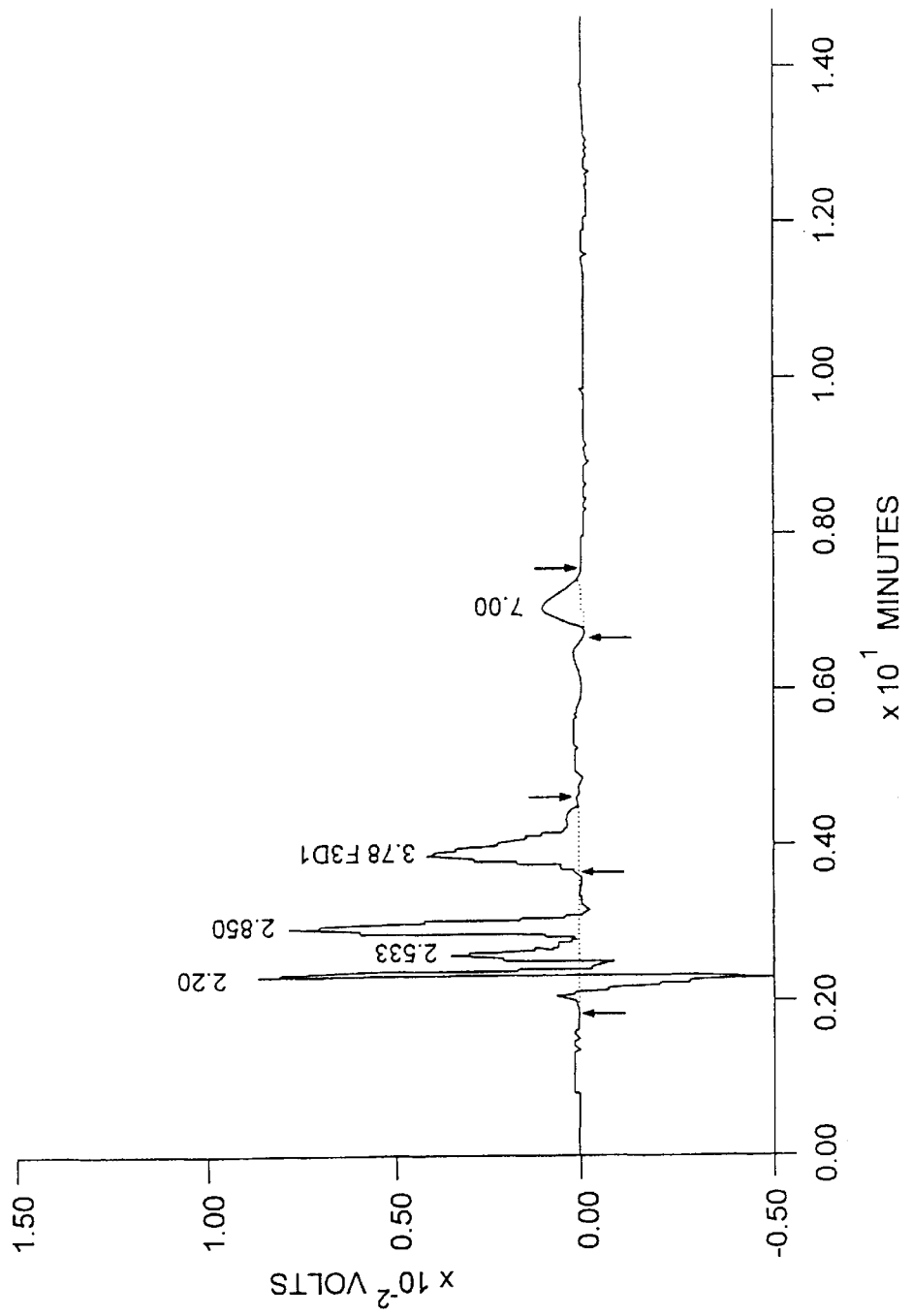

Genomic DNA from the wild type (wt) and an ORF9 mutant was digested with BglII, and with both BglII and EcoRI, and probed with a 0.6-kb BglII-SstI fragment (FIG. 24). In the BglII digests, the 2.4 kb hybridizing fragment present in the wild type has been replaced with a 3.9 kb fragment in the mutant, while in the BglII-EcoRI digests, the 1-kb fragment has been replaced with a 0.6 kb fragment. In BglII-EcoRI digests of the ORF9 mutant genomic DNA another 3.3-kb EcoRI-BglII fragment might have been expected to hybridize to the probe, but failure to see this fragment can be attributed to the fact that the probe has only approximately 50 bp of sequence homologous to the expected fragment. Since the post-hybridization washes were carried out under stringent conditions this small amount of homology might not be sufficient to give a hybridizing band. Nevertheless, the sizes of other hybridizing fragments are consistent with the replacement of the wild type ORF9 with the apr disrupted ORF9.

The Effect of Mutations Within the ORF's of the 12 kb Fragment on Clavulanic Acid Synthesis 1. Bioassay Clavulanic acid production in *S. lividans* transformants was bioassayed by the method of Jensen et al., (industrial Microorganisms: Basic and Applied Molecular Genetics, 1993, Chapter 22, Edited by R. H. Baltz, G. D. Hegemam, P. L. Skatrud, Published by The American Society for Microbiology, Washington, D.C.). Basically the method involves patching select transformants onto agriplates, and after a 48 hours incubation period at 28° C., overlayering these organisms with a β-lactamase-producing indicator organism, together with penicillin G, at a concentration of 1 µ/ml. The results are summarized below:

TABLE II

| Strain | No Penicillin | Penicillin G (1µ/ml) |
|---|---|---|
| wild type | 0 mm | 28 mm |
| ORF2 | 0 mm | 0 mm |
| ORF3 | 0 mm | 0 mm |
| ORF6 | 0 mm | 0 mm |
| ORF8 | 0 mm | 0 mm |
| ORF9 | 0 mm | 0 mm |

If a zone of inhibition is obtained in the presence of penicillin but not in the absence thereof or if the size of the zones in the presence of penicillin is greater than the zones without penicillin, it is indicative of a β-lactamase inhibitory activity of clavulanic acid. The bioassay thus showed that transformants containing mutants with insertion in any one of the ORF2, ORF3, ORF6, ORF8 or ORF9 failed to produce β-lactamase inhibitory activity of clavulanic acid, thus indicating that each of these ORFs are involved in the production of clavulanic acid.

2. HPLC Analysis

The amount of clavulanic acid produced by each transformant was also quantitated in each sample by HPLC. This assay was done to confirm the presence or absence of clavulanic acid production, within the cultured supernatants produced from each gene disruption mutant.

Culture Conditions for the Growth of Wild Type and the Mutants for Clavulanic Acid Production Spores of transformants containing insertional mutations within either ORF2, ORF3, ORF6, ORF8 or ORF9 were first inoculated into 20 mL Trypticase Soy Broth containing 1% starch, and the culture was grown shaking for 48 hours at 28° C. which served as a seed culture. The seed culture was then used at 1% inoculum to inoculate 20 ml Starch Asparagine medium the composition of which has been described earlier (Paradkar and Jensen (1995), J Bacteriol Vol. 177, pp. 1307–1314), and the culture was grown in the same conditions as the seed culture. Supernatants (0.1 mL) were obtained from 96 hour cultures, and derivatized with 25 µL of imidazole reagent. Subsequently, a 50 µL aliquot of the derivatized sample was analyzed by HPLC.

The high pressure liquid chromatography assay was conducted as described in Foulstone and Reading (1982, Antimicrob. Agents Chemother. 22:753–762).

Analysis was performed with a model M-45 pump, model 712 WISP automated sample injector, and model 480 variable-wavelength UV detector, all from Millipore Waters (Mississauga, Ontario, Canada). Samples (1001 µl) were mixed with imidazole reagent (25 µl) and incubated at room temperature for 15 min to form imidazole-derivatized clavulanic acid. Derivatized samples (50 µl) were analyzed on a reverse-phase column (µBondapak-C18) with an isocratic buffer system consisting of 0.1 M $KH_2PO_4$-6% methanol, PH 3.2 (adjusted with $H_3PO_4$). Under these conditions, authentic clavulanic acid has a retention time of 6.5 min.

The HPLC chromatograms of culture supernatants from transformants containing an insertional mutation within ORF2, ORF3, ORF6, ORF8 or ORF9 and of the wild type were obtained. An example of these results is illustrated in FIG. 25, which represents the HPLC profile of wild type (B) or the ORF8 insertion mutant (C). As can be seen from FIG. 25, clavulanic acid was detected in the supernatant of the wild type as a peak, at a retention time of 9.1 minutes. An authentic sample of clavulanic acid also gave a retention time of approximately 9.1 minutes (FIG. 25 (A). The amount of clavulanic acid produced by the wild type was determined by integrating the clavulanic acid peak in the wild type supernatant.

The present invention is not limited to the features of the embodiments described herein, but includes all variations and modifications within the scope of the claims.

We claim:
1. An isolated protein having the amino acid sequence of SEQ ID NO: 12.

\* \* \* \* \*